United States Patent
Froidevaux et al.

(10) Patent No.: US 11,685,729 B2
(45) Date of Patent: Jun. 27, 2023

(54) C5A RECEPTOR MODULATORS

(71) Applicant: IDORSIA PHARMACEUTICALS LTD., Allschwil (SE)

(72) Inventors: Sylvie Froidevaux, Allschwil (SE); Francis Hubler, Allschwil (SE); Mark Murphy, Allschwil (SE); Dorte Renneberg, Allschwil (SE); Simon Stamm, Allschwil (SE)

(73) Assignee: IDORSIA PHARMACEUTICALS LTD., Allschwil (CH)

( * ) Notice: Subject to any disclaimer, the term of this patent is extended or adjusted under 35 U.S.C. 154(b) by 359 days.

(21) Appl. No.: 16/963,143

(22) PCT Filed: Jan. 18, 2019

(86) PCT No.: PCT/EP2019/051245
§ 371 (c)(1),
(2) Date: Jul. 17, 2020

(87) PCT Pub. No.: WO2019/141808
PCT Pub. Date: Jul. 25, 2019

(65) Prior Publication Data
US 2021/0122736 A1    Apr. 29, 2021

(30) Foreign Application Priority Data
Jan. 19, 2018   (WO) ................ PCT/EP2018/051283

(51) Int. Cl.
C07D 401/04    (2006.01)
C07D 403/04    (2006.01)
C07D 401/14    (2006.01)
C07D 417/14    (2006.01)
C07D 487/04    (2006.01)

(52) U.S. Cl.
CPC ......... C07D 403/04 (2013.01); C07D 401/04 (2013.01); C07D 401/14 (2013.01); C07D 417/14 (2013.01); C07D 487/04 (2013.01)

(58) Field of Classification Search
CPC .. C07D 403/04; C07D 401/04; C07D 401/14; C07D 417/14; C07D 487/04
See application file for complete search history.

(56) References Cited

U.S. PATENT DOCUMENTS

| | | | |
|---|---|---|---|
| 5,658,917 A | 8/1997 | Fujiwara et al. | |
| 6,645,971 B1 | 11/2003 | Muraoka et al. | |
| 9,126,939 B2* | 8/2015 | Fan et al. ............ | A61K 31/445 |
| | | | 514/235.6 |
| 17,625,522 | 1/2022 | Ambuehl | |
| 2012/0143725 A1 | 6/2012 | Hutchinson et al. | |
| 2013/0172347 A1* | 7/2013 | Fan ........................... | A61P 9/08 |
| 2020/0347029 A1 | 11/2020 | Froidevaux et al. | |

FOREIGN PATENT DOCUMENTS

| | | |
|---|---|---|
| EP | 1122253 A1 | 8/2001 |
| EP | 1122253 A4 | 5/2003 |
| WO | 9419342 A1 | 9/1994 |
| WO | 0023436 A1 | 4/2000 |
| WO | 0024744 A1 | 5/2000 |
| WO | 2005063209 A1 | 7/2005 |
| WO | 2008011032 A1 | 1/2008 |
| WO | 2012143725 A1 | 10/2012 |
| WO | 2015033299 A1 | 3/2015 |
| WO | 2015034820 A1 | 3/2015 |
| WO | 2015044900 A1 | 4/2015 |
| WO | 2019137927 A1 | 7/2019 |
| WO | 2019141803 A1 | 7/2019 |
| WO | 2019141808 A1 | 7/2019 |

OTHER PUBLICATIONS

Ethan P. Grant; Essential Role for the C5a Receptor in Regulating the Effector Phase of Synovial Infiltration and Joint Destruction in Experimental Arthritis; J Exp Med (2002) 196 (11): 1461-1471. (Year: 2002).*
Corrales L, Ajona D, Rafail S, Lasarte JJ, Riezu-Boj JI, Lambris JD, Rouzaut A, Pajares MJ, Montuenga LM, Pio R. Anaphylatoxin C5a creates a favorable microenvironment for lung cancer progression. J Immunol. Nov. 1, 2012;189(9):4674-83. (Year: 2012).*
Jain U, Woodruff TM, Stadnyk AW. The C5a receptor antagonist PMX205 ameliorates experimentally induced colitis associated with increased IL-4 and IL-10. Br J Pharmacol. Jan. 2013;168(2):488-501. doi: 10.1111/j.1476-5381.2012.02183.x. PMID: 22924972; PMCID: PMC3572573. (Year: 2013).*
Vadrevu SK, Chintala NK, Sharma SK, Sharma P, Cleveland C, Riediger L, Manne S, Fairlie DP, Gorczyca W, Almanza O, Karbowniczek M, Markiewski MM. Complement c5a receptor facilitates cancer metastasis by altering T-cell responses in the metastatic niche. Cancer Res. Jul. 1, 2014;74(13):3454-65. (Year: 2014).*

(Continued)

Primary Examiner — Scarlett Y Goon
Assistant Examiner — Michael Kirberger
(74) Attorney, Agent, or Firm — Jeff B. Vockrodt; Culhane Meadows PLLC

(57) ABSTRACT

The present invention relates to derivatives of formula (I)

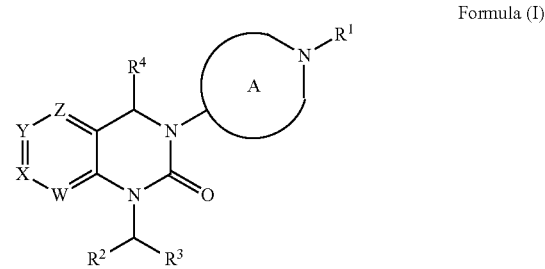

Formula (I)

wherein Ring A, W, X, Y, Z, $R^1$, $R^2$, $R^3$ and $R^4$ are as described in the description, to their preparation, to pharmaceutically acceptable salts thereof, and to their use as pharmaceuticals, to pharmaceutical compositions containing one or more compounds of formula (I), and especially to their use as C5a receptor modulators.

18 Claims, No Drawings

(56) References Cited

OTHER PUBLICATIONS

Darling VR, Hauke RJ, Tarantolo S, Agrawal DK. Immunological effects and therapeutic role of C5a in cancer. Expert Rev Clin Immunol. Feb. 2015;11(2):255-63. (Year: 2015).*
Wang Y, Sun SN, Liu Q, Yu YY, Guo J, Wang K, Xing BC, Zheng QF, Campa MJ, Patz EF Jr, Li SY, He YW. Autocrine Complement Inhibits IL10-Dependent T-cell-Mediated Antitumor Immunity to Promote Tumor Progression. Cancer Discov. Sep. 2016;6(9):1022-35. doi: 10.1158/2159-8290.CD-15-1412. (Year: 2016).*
Bekker P, et al. (2016) Characterization of Pharmacologic and Pharmacokinetic Properties of CCX168, a Potent and Selective Orally Administered Complement 5a Receptor Inhibitor, Based on Preclinical Evaluation and Randomized Phase 1 Clinical Study. PLOS ONE 11(10): e0164646. (Year: 2016).*
International Search Report received in Application No. PCT/EP2019/051245 dated Apr. 4, 2019, 2 pages.
Written Opinion of the International Searching Authority received in Application No. PCT/EP2019/051245.
Zhang et al., Clin J Am Soc Nephrol (2014) 9: 1876-1882.
Zwirner, J., et al. (1999) Mol Immunol 36(13-14): 877-884.
"Handbook of Pharmaceutical Salts. Properties, Selection and Use. ", P. Heinrich Stahl, Camille G. Wermuth (Eds.), Wiley-VCH, 2008.
"Pharmaceutical Salts and Co-crystals", Johan Wouters and Luc Quéré (Eds.), RSC Publishing, 2012.
"Protective Groups in Organic Synthesis", T.W. Greene, P.G.M. Wuts, Wiley-Interscience, 1999.
Ager, R. R., et al. (2010) J Neurochem 113(2): 389-401.
Amsterdam, E. A., et al. (1995) Am J Physiol 268(1 Pt 2): H448-457.
Bao, L., et al. (2005) Eur J Immunol 35(8): 2496-2506.
Basta, M. and D. R. Branch (2014) Clin Exp Immunol 178 Suppl 1: 87-88.
Baumann, U., et al. (2000) J Immunol 164(2): 1065-1070.
Bless, N. M., et al. (1999) Am J Physiol 276(1 Pt 1): L57-63.
Bozic, C. R., et al. (1996) Science 273(5282): 1722-1725.
Cao, Q., et al. (2012) Am J Physiol Cell Physiol 302(12): pp. 1731-1740.
Cheng, L., et al. (2013). Invest Ophthalmol Vis Sci 54(13): 8191-8198.
Craddock, P. R., et al. (1977) J Clin Invest 60(1): 260-264.
Craddock, P. R., et al. (1977) N Engl J Med 296(14): 769-774.
Czermak, B. J., et al. (1998) J Leukoc Biol 64(1): 40-18.
Czermak, B. J., et al. (1999) Nat Med 5(7): 788-792.
Dang, L., et al. (2015) Mol Med Rep 11(6): 4183-4189.
Davin, J. C., N. C. van de Kar (2015) Ther Adv Hematol 6(4): 171-185.
De Hoog, V. C., et al. (2014) Cardiovasc Res 103(4): 521-529.
Diani, M., G. Altomare and E. Reali (2015) Autoimmun Rev 14(4): 286-292.
Distelmaier, K., et al. (2009) Thromb Haemost 102(3): 564-572.
Farrar, C. A. and S. H. Sacks (2014) Curr Opin Organ Transplant 19(1): 8-13.
Fiebiger, E., et al. (1998) J Clin Invest 101(1): 243-251.
Fonseca, M. I., et al. (2013) J Neuroinflammation 10: 25.
Gammon, W. R. (1989) Immunol Ser 46: 509-525.
Gasque, P., et al. (1997) Am J Pathol 150(1): 31-41.
Grant, E. P., et al. (2002) J Exp Med 196(11): 1461-1471.
Guo, R. F. and P. A. Ward (2005) Annu Rev Immunol 23: 821-852.
Guo, R. F., et al. (2000) J Clin Invest 106(10): 1271-1280.
Halstead, S. K., et al. (2008) Brain 131 (Pt 5): 1197-1208.
Hammerschmidt, D. E., et al. (1980) Lancet 1(8175): 947-949.
Hartung, H. P., et al. (1987) Neurology 37(6): 1006-1009.
Heideman, M. and T. E. Hugli (1984) J Trauma 24(12): 1038-1043.
Heimbach, L., et al. (2011) J Biol Chem 286(17): 15003-15009.
Hoesel, L. M., et al. (2007) J Immunol 178(12): 7902-7910.
Hopken, U., et al. (1996) Eur J Immunol 26(5): 1103-1109.
Howard, R. J., et al. (1988) Arch Surg 123(12): 1496-1501.
Howell et al. (2011), J. Clin. Invest. 121(4): 1429-1444.
Huang, Y. M., et al. (2015) Arthritis Rheumatol 67(10): 2780-2790.
Huber-Lang, M., et al. (2001) J Immunol 166(2): 1193-1199.
Humayun, S., et al. (2009) J Neuroimmunol 210(1-2): 52-62.
Jacob, A., B. Hack, et al. (2010) J Neuroimmunol 221(1-2): 46-52.
Jain, U., et al. (2013) Br J Pharmacol 168(2): 488-501.
Johswich, K., et al. (2009) Inflamm Bowel Dis 15(12): 1812-1823.
Jose, P. J., et al. (1990) Ann Rheum Dis 49(10): 747-752.
Kallenberg, C. G. and P. Heeringa (2015) Mol Immunol 68(1): 53-56).
Kaplan, A. P. (2004) J Allergy Clin Immunol 114(3): 465-174.
Karsten, C. M. and J. Kohl (2012) Immunobiology 217(11): 1067-1079.
Amsterdam, E. A., et al. (1995) Am J Physiol 268(1 Pt 2): 448-457.
Bless, N. M., et al. (1999) Am J Physiol 276(1 Pt 1): 57-63.
C.W. Pouton, Eur. J. Pharm. Sci. 11 (2000) S93-S98.
Cao, Q., et al. (2012) Am J Physiol Cell Physiol 302(12): C1731-1740.
Cuiné J. et al. 2008 . . . J. Pharm. Sci. 97 (2), 995-1012.
E.T. Cole, "Liquid Filled Hard Gelatin Capsules", Pharm. Technol. Int.,Sep./Oct. 1989.
European Pharmacopeia Technical Guide (1999, p. 86).
Feeney et al.; Advanced Drug Delivery Reviews 101 (2016) 167-194.
H. Seager, Soft Gelatin Capsules, Pharm. Tech. 1985, 9(9), 84-104.
Janeway's Immunobiology, 8th edition (2012), Kenneth Murphy, GarlandScience, p. 48-72.
Perry's Chemical Engineers' Handbook, 7th edition, Perry, R.H.; Green, D.W. McGraw-Hill 1997.
Polymorphism in the Pharmaceutical Industry (Ed. R. Hilfiker, VCH, 2006),Chapter 8: U.J. Griesser: The Importance of Solvates.
R.C. Rowe, P.J. Seskey, S.C. Owen, Handbook of Pharmaceutical Excipients,5th edition, Pharmaceutical Press 2006.
Search Report received in Application No. PCT/EP2020/069230 dated Sep. 21, 2020, 2 pages.
The United States Pharmacopeia (USP) 23, General Information,Pharmaceutical Dosage Forms 1151: 1942-1943 (1995).
Umesh S. Kestur, Lynne S. Taylor; CrystEngComm, Dec. 2010, 2390-2397.
Written Opinion received in Application No. PCT/EP2020/069230 dated Sep. 21, 2020, 5 pages.
Kirklin, J. K., et al. (1983) J Thorac Cardiovasc Surg 86(6): 845-857.
Kohl, J. and J. E. Gessner (1999) Mol Immunol 36(13-14): 893-903.
Lawley, T. J., et al. (1979) J Immunol 123(3): 1382-1387.
Li, L., et al. (2015) Metabolism 64(5): 597-610.
Liu, L., et al. (2014) J Clin Immunol 34(2): 224-232.
Ma, R., et al. (2013) J Clin Immunol 33(1): 172-178.
Mantovani, S., et al. (2014) J Neuroimmunol 276(1-2): 213-218.
Marc, M. M., et al. (2004) Am J Respir Cell Mol Biol 31(2): 216-219.
Mavroidis, M., et al. (2015) Basic Res Cardiol 110(3): 27.
Mrowietz, U., et al. (2001) Exp Dermatol 10(4): 238-245.
Mueller, M., et al. (2013) Immunobiology 218(9): 1131-1138.
Mulligan, M. S., et al. (1996) J Clin Invest 98(2): 503-512.
N.S. Merle et al. (2015), Front Immunol 6: 257.
Nataf, S., et al. (1999) J Immunol 162(7): 4018-4023.
Neuber, K., R. et al. (1991) Immunology 73(1): 83-87.
O'Barr, S. A., et al. (2001) J Immunol 166(6): 4154-4162.
Pandey et al. (2017) Nature 543: 108-112.
Pandey, M. K. (2013) Curr Allergy Asthma Rep 13(6): 596-606.
Pawaria, S., et al. (2014) J Immunol 193(7): 3288-3295.
Porcel, J. M., et al. (1995) Clin Immunol Immunopathol 74(3): 283-288.
Remington, The Science and Practice of Pharmacy, 21st Edition (2005), Part 5, "Pharmaceutical Manufacturing" [published by Lippincott Williams & Wilkins]).
Ricklin, D., et al. (2010), Nat Immunol 11(9): 785-797.
Riley, R. D., et al. (2000) J Thorac Cardiovasc Surg 120(2): 350-358.
Sarma, J. V. and P. A. Ward (2012) Cell Health Cytoskelet 4: 73-82.
Singhrao et al. (1999) Experimental Neurology 159, 362-376.
Smedegard, G., et al. (1989) Am J Pathol 135(3): 489-197.
Song, D., et al. (2015) Am J Reprod Immunol 74(4): 345-356.
Sprott, H., et al. (2000) J Rheumatol 27(2): 402-104.
Staab, E. B., et al. (2014) Int Immunopharmacol 21(2): 293-300.

(56) References Cited

OTHER PUBLICATIONS

Stevens, J. H., et al. (1986) J Clin Invest 77(6): 1812-1816.
Strachan, A. J., et al. (2000) J Immunol 164(12): 6560-6565.
Tofukuji, M., et al. (1998) J Thorac Cardiovasc Surg 116(6): 1060-1068.
Tsuji, R. F., et al. (2000) J Immunol 165(3): 1588-1598.
Unnewehr, H., et al. (2013) J Immunol 190(8): 4215-4225.
Volanikis, J.; Vasculitis, 2nd Edition (2008), Edited by Ball and Bridges, Oxford University Press, pp. 47-53.
Wakerley, B. R. and N. Yuki (2015) Expert Rev Neurother 15(8): 847-849.
Wang Y., et al., (2016) Cancer Discovery 6(9) 1022-1035.
Wang, X. J., et al. (2007) Neurochem Int 50(1): 39-50.
Weisman, H. F., T. et al. (1990) Science 249(4965): 146-151.
Werfel, T., et al. (1997) Arch Dermatol Res 289(2): 83-86.
Wong EK, Kavanagh D, Transl Res. (2015) 165(2):306-20.
Woodruff, T. M., et al. (2003) J Immunol 171(10): 5514-5520.
Woodruff, T. M., et al. (2008) J Immunol 181(12): 8727-8734.
Xiao, H. et al. (2014) J Am Soc Nephrol 25(2): 225-231.
Yan, S., et al. (2014) J Dermatol Sci 76(3): 240-245.
Yuan, G., et al. (2003) Chin Med J (Engl) 116(9): 1408-1412.
Zecher, D., et al. (2014) Arterioscler Thromb Vasc Biol 34(2): 313-320.
Zha H., et al. (2017) Oncoimmunology 6(10): e1349587.

\* cited by examiner

C5A RECEPTOR MODULATORS

CROSS REFERENCE TO REPLATED APPLICATIONS

This application is filing under 35 U.S.C. § 371 of international application number PCT/EP2019/051245, filed Jan. 18, 2019, which claims priority to application number PCT/EP2018/051283 filed on Jan. 19, 2018, the entire disclosures of each of which are hereby incorporated by reference.

The present invention relates to novel C5a receptor modulators of formula (I) and their use as pharmaceuticals. The invention also concerns related aspects including processes for the preparation of the compounds, pharmaceutical compositions containing one or more compounds of formula (I), and their use as C5a receptor modulators, especially in the treatment of vasculitic diseases or disorders, inflammatory diseases or disorders involving intravascular microvesicle release, immune complex (IC) diseases or disorders, neurodegenerative diseases or disorders, complement related inflammatory diseases or disorders, bullous diseases or disorders, diseases or disorders related to ischemia and/or ischemic reperfusion injury, inflammatory bowel diseases or disorders, and autoimmune diseases or disorders; as well as in contact sensitivity or an inflammation caused by contact with artificial surfaces; increased leukocyte and platelet activation (and infiltration to tissues thereof); pathologic sequelae associated to an intoxication or an injury such as a trauma, an hemorrhage, a shock, or surgery including transplantation, such sequelae including multiple organ failure (MOF), septic shock, shock due to intoxication, or acute lung inflammatory injury; pathologic sequelae associated with insulin-dependent diabetes mellitus; myocardial infarction or thrombosis; edema or an increased capillary permeability; reduction of coronary endothelial dysfunction induced by cardiopulmonary bypass and/or cardioplegia; or cancer.

C5aR1 (CD88) is a seven transmembrane bound G protein coupled receptor (GPCR) belonging to the rhodopsin like family, the gene of which is located on chromosome 19. It couples to pertussis toxin sensitive Gialpha2, Gialpha3 or pertussis toxin insensitive Galpha16 and initiates several downstream signaling pathways. C5aR1 is expressed on a number of immune cell types including monocytes, neutrophils, mast cells, basophils and eosinophils. In addition, it is expressed on many other cell types including hepatocytes, pulmonary and endothelial cells, microglia, neurons and renal glomerular cells. There are a number of ligands described which bind to the C5aR. These include C5a, C5adesArg and C5a +1 kDa. C5a is a central effector molecule of the complement system which itself is a complex enzymatic cascade evolved to crucially complement the immune system against invading pathogens, however, a significant body of evidence shows that inadvertent complement activation leads to many acute inflammatory disorders and autoimmune diseases (Ricklin, D., et al. (2010) "Complement: a key system for immune surveillance and homeostasis." Nat Immunol 11(9): 785-797) and specifically C5a has been shown to be elevated in a number of these inflammatory and autoimmune disorders. The complement system is activated through four pathways: The classical pathway, and the mannose binding lectin (MBL) pathway which is similar to the classical pathway except for the initial recognition and activation steps which recognize pathogens or antibody complexes. The alternative pathway is activated by binding of spontaneously activated complement C3 protein (C3b fragment) to pathogen surface. These three pathways all lead to the eventual formation of C3 convertases, which is the point where the 3 pathways converge (Guo, R. F. and P. A. Ward (2005) Annu Rev Immunol 23: 821-852). Subsequently C3 convertases lead to the formation of the anaphalatoxins C3a and C5a, together with other complement proteins required to produce the membrane attack complex. A fourth pathway, the extrinsic pathway involves plasma proteases (eg. elastase, thrombin) which act directly on C3 or C5 leading to the subsequent production of C3a and C5a. The anaphylatoxin C5a leads to the recruitment and activation of inflammatory cells of the innate and adaptive system, partly through the enhancement of cell adhesion molecule expression, the release of granule-based enzymes, delayed or enhanced apoptosis, phagocytosis, oxidative burst, histamine secretion and release and chemotaxis. In addition, it elicits the release of other pro inflammatory mediators, such as TNF-a, IL-1, IL-6, IL-8, prostaglandins, and leukotrienes) (N. S. Merle et al. (2015) "Complement System Part II: Role in Immunity." Front Immunol 6: 257), activation of endothelial cells and vascular permeability which may lead to events in which at the end thrombotic microangiopathy can occur. Therefore, C5a represents one of the most potent inflammatory molecules produced during immune responses and because of its fundamental biology it is potentially implicated in a very wide range of pathologies (Janeway's Immunobiology, 8th edition (2012), Kenneth Murphy, Garland Science, p. 48-72).

C5a is central to the immune system and as such is important in key aspects of inflammation and tissue injury. In addition, there is considerable experimental evidence in the literature that implicates increased levels of C5a with a number of diseases and disorders, in particular in autoimmune and inflammatory diseases and disorders (Ricklin, D., et al. (2010) Nat Immunol 11(9): 785-797).

There is a large body of evidence about C5a and its receptor C5aR in contributing to vasculitic diseases, which demonstrate that C5a levels are elevated and give rise to leukocyte migration and subsequent inflammation which then leads to the eventual destruction of vessel walls (Charles J., et al (2013) Semin Nephrol 33(6): 557-564; Vasculitis, $2^{nd}$ Edition (2008), Edited by Ball and Bridges, Oxford University Press, pp 47-53; Huang, Y. M., et al. (2015) Arthritis Rheumatol 67(10): 2780-2790; Kallenberg, C. G. and P. Heeringa (2015) Mol Immunol 68(1): 53-56). Inhibition of the C5aR with a C5aR antagonist was effective at ameliorated anti-myeloperoxidase (MPO)-induced NCGN in mice expressing the human C5a receptor (Xiao, H. et al (2014) J Am Soc Nephrol 25(2): 225-231) and was confirmed to be effective in a phase II trial of patients with anti-neutrophil cytoplasmic antibody (ANCA) associated vasculitis (ClinicalTrials.gov Identifier NCT02222155). Therefore, a C5a antagonist may be useful to treat vasculitic diseases such as ANCA associated vasculitis, leukoclastic vasculitis, Wegener's granulomatosis, microscopic polyangiitis, Churg-Strauss syndrome, Henoch-Schönlein purpura, polyateritis nodosa, rapidly progressive glomerulonephritis (RPGN), cryoglobulinaemia, giant cell arteritis (GCA), Behcet's disease and Takayasu's arteritis (TAK).

C5a is generated when human blood makes contact with artificial surfaces, such as in cardiopulmonary bypass and hemodialysis procedures for instance on the artificial surface of the heart—lung machine in association with vascular surgery such as coronary artery bypass grafting or heart valve replacement or on surfaces of a kidney dialysis machine (Howard, R. J., et al. (1988) Arch Surg 123(12): 1496-1501; Kirklin, J. K., et al. (1983) J Thorac Cardiovasc Surg 86(6): 845-857; Craddock, P. R., et al. (1977) J Clin Invest 60(1): 260-264; Craddock, P. R., et al. (1977) N Engl J Med 296(14): 769-774) or in association with contact with other artificial vessels or container surfaces (e.g. ventricular assist devices, artificial heart machines, transfusion tubing, blood storage bags, plasmapheresis, plateletpheresis, and the like). As such C5aR antagonists could prove useful in preventing deleterious consequences of contact sensitivity and/or inflammation caused by contact with artificial surfaces. In addition, it may be useful in treating inflammatory disorders involving intravascular microvesicle release such as for example thrombotic microangiopathy and sickle cell disease (Zecher, D., et al. (2014) Arterioscler Thromb Vasc Biol 34(2): 313-320). A C5aR antagonist could also prove useful in certain hemotological diseases which are associated with activation of coagulation and fibrinolytic systems, disseminated intravascular coagulation (DIC), pernicious anemia, warm and cold autoimmune hemolytic anemia (AIHA), anti-phospholipid syndrome and its associated complications, arterial and venous thrombosis, pregnancy complications such as recurrent miscarriage and fetal death, preeclampsia, placental insufficiency, fetal growth restriction, cervical remodeling and preterm birth, idiopathic thrombocytopenic purpura (ITP), atypical hemolytic uremic syndrome (aHUS), paroxysmal nocturnal hemoglobinuria (PNH) and allergic transfusion reactions. The C5-specific humanized antibody, eculizumab is approved for paroxysmal nocturnal hemoglobinuria and atypical haemolytic uraemic syndrome (aHUS) (Wong E K, Kavanagh D, Transl Res. (2015) 165(2):306-20) and has been shown to be efficacious in renal transplant such as acute antibody-mediated kidney allograft rejection and cold agglutinin disease further supporting a potential role for C5aR antagonists in these diseases.

In myocardial ischemia-reperfusion injury C5a has been described to have an important function. Complement depletion reduced myocardial infarct size in mice (Weisman, H. F., T. et al. (1990) Science 249(4965): 146-151; De Hoog, V. C., et al. (2014) Cardiovasc Res 103(4): 521-529) and treatment with anti-C5a antibodies reduced injury in a rat model of hindlimb ischemia-reperfusion (Bless, N. M., et al. (1999) Am J Physiol 276 (1 Pt 1): L57-63). Reperfusion injury during myocardial infarction was also markedly reduced in pigs that were re-treated with a monoclonal anti-C5a IgG (Amsterdam, E. A., et al. (1995) Am J Physiol 268 (1 Pt 2): H448-457). A recombinant human C5aR antagonist reduces infarct size in a porcine model of surgical revascularization (Riley, R. D., et al. (2000) J Thorac Cardiovasc Surg 120(2): 350-358) providing evidence for the utility of a C5aR antagonist in these diseases. In addition, diseases related to ischemia/reperfusion injury, such as those resulting from transplants, including solid organ transplant, where C5a has been shown to play an important role (Farrar, C. A. and S. H. Sacks (2014) Curr Opin Organ Transplant 19(1): 8-13), could benefit from a C5aR antagonist as could related syndromes such as ischemic reperfusion injury, ischemic colitis and cardiac ischemia (Mueller, M., et al. (2013) Immunobiology 218(9): 1131-1138).

Furthermore, diseases where complement plays a role such as coronary thrombosis (Distelmaier, K., et al. (2009) Thromb Haemost 102(3): 564-572), vascular occlusion, post-surgical vascular reocclusion, atherosclerosis, traumatic central nervous system injury, arrhythmogenic cardiomyopathy (Mavroidis, M., et al. (2015) Basic Res Cardiol 110(3): 27) and Gaucher disease (Pandey et al. (2017) Nature 543: 108-112) could also benefit from a C5aR antagonist. Thus, C5aR modulators may be used preventatively in a patient at risk for myocardial infarction or thrombosis (i.e. a patient who has one or more recognized risk factors for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

C5a causes increased capillary permeability and edema, leukocyte and platelet activation and infiltration to tissues, as well as bronchoconstriction (Sarma, J. V. and P. A. Ward (2012) Cell Health Cytoskelet 4: 73-82; Czermak, B. J., et al. (1998) J Leukoc Biol 64(1): 40-48). Administration of an anti-C5a monoclonal antibody was shown to reduce cardiopulmonary bypass and cardioplegia-induced coronary endothelial dysfunction (Tofukuji, M., et al. (1998) J Thorac Cardiovasc Surg 116(6): 1060-1068).

C5a and its receptor are also involved in the pathogenesis of acute respiratory distress syndrome (ARDS) (Hammerschmidt, D. E., et al. (1980) Lancet 1(8175): 947-949), Chronic Obstructive Pulmonary Disorder (COPD) (Marc, M. M., et al. (2004) Am J Respir Cell Mol Biol 31(2): 216-219), and multiple organ failure (MOF) (Huber-Lang, M., et al. (2001) "Role of C5a in multiorgan failure during sepsis." J Immunol 166(2): 1193-1199; Heideman, M. and T. E. Hugli (1984) J Trauma 24(12): 1038-1043). C5a increases monocyte production of two important proinflammatory cytokines TNF-α and IL-I which contribute to pathology in these diseases. C5a has also been shown to play an important role in the development of tissue injury, and particularly pulmonary injury, in animal models of septic shock (Smedegard, G., et al. (1989) Am J Pathol 135(3): 489-497; Unnewehr, H., et al. (2013) J Immunol 190(8): 4215-4225). In sepsis models using rats, pigs and non-human primates, anti-C5a antibodies administered to the animals before treatment with endotoxin or E. coli resulted in decreased tissue injury, as well as decreased production of IL-6 (Hopken, U., et al. (1996) Eur J Immunol 26(5): 1103-1109; Stevens, J. H., et al. (1986) J Clin Invest 77(6): 1812-1816). Inhibition of C5a with anti-C5a polyclonal antibodies has been shown to significantly improve survival rates in a caecal ligation/puncture model of sepsis in rats (Czermak, B. J., et al. (1999) Nat Med 5(7): 788-792). In the same sepsis model, anti-C5a antibodies were shown to inhibit apoptosis of thymocytes (Guo, R. F., et al. (2000) J Clin Invest 106(10): 1271-1280). Anti-C5a antibodies were also protective in a cobra venom factor model of lung injury in rats, and in immune complex-induced lung injury (Mulligan, M. S., et al. (1996) J Clin Invest 98(2): 503-512). The importance of C5a in immune complex-mediated lung injury was also shown in mouse (Bozic, C. R., et al. (1996) Science 273(5282): 1722-1725). Therefore, a C5aR antagonist could be of benefit in many inflammatory disorders and related conditions including neutropenia, sepsis, septic shock, stroke, inflammation associated with severe burns (Hoesel, L. M., et al. (2007) J Immunol 178(12): 7902-7910), osteoarthritis (Yuan, G., et al. (2003) Chin Med J (Eng)) 116(9): 1408-1412), as well as acute (adult) respiratory distress syndrome (ARDS), chronic pulmonary obstructive disorder (COPD), bronchial asthma (Pandey, M. K. (2013) Curr Allergy Asthma Rep 13(6): 596-606), systemic inflammatory response syndrome (SIRS), tissue graft rejection, hyperacute rejection of transplanted organs, and the like, and multiple organ dysfunction syndrome (MODS). In addition, C5aR antagonists may be beneficial in treating pathologic sequelae associated with insulin-dependent diabetes mellitus such as diabetic kidney disease (Li, L., et al. (2015) Metabolism 64(5): 597-610), diabetic retinopathy (Cheng, L., et al. (2013). Invest Ophthalmol Vis Sci 54(13): 8191-8198), lupus nephropathy (Bao, L., et al. (2005) Eur J Immunol 35(8): 2496-2506), Heyman nephritis, membranous nephritis, and other forms of glomerulonephritis such as C3 glomerulopathy including dense deposit disease (DDD) (Zhang et al., Clin J Am Soc Nephrol (2014) 9: 1876-1882). Furthermore, the compound eculizumab has been shown to have potential utility for the treatment of neuromyelitis optica.

C5aR antagonists substantially reduced ovalbumin (OVA)-induced total cell (60%), neutrophil (66%) and eosinophil (65%) influxes in lavage fluid sampling suggesting that C5aR blockage might represent a novel therapeutic agent for reducing asthmatic outcomes (Staab, E. B., et al. (2014) Int Immunopharmacol 21(2): 293-300).

The complement system and in particular C5a contribute to the development of many bullous diseases among other things through activation of innate cells including mast cells and neutrophils (e.g. bullous pemphigoid, bullous acquisita, pemphigus foliaceus and pemphigus vulgaris). The detachment of epidermal basal keratinocytes from the underlying basement membrane is thought to be caused by autoantibodies to keratinocytes at the cutaneous basement membrane leading to blisters and a high influx of neutrophils in both the upper dermal layers and within the blister cavities. In experimental models a reduction of neutrophils or absence of complement (total or C5-selective) can inhibit formation of sub-epidermal blisters (Heimbach, L., et al. (2011) J Biol Chem 286(17): 15003-15009; Gammon, W. R. (1989) Immunol Ser 46: 509-525). Recent evidence has emerged to suggest that inhibition of C5a may prove beneficial in the treatment of the skin disorder hidradenitis suppurativa where an antibody against human C5a was shown to improve patient outcome in an open label phase II clinical trial. A C5a receptor antagonist may therefore be useful in bullous diseases.

Complement is believed to be important in inflammatory bowel disease (IBD) pathology and the C5aR is found to be expressed in the epithelial cells of the colon. (Cao, Q., et al. (2012) Am J Physiol Cell Physiol 302(12): C1731-1740). In addition, pharmacological inhibition of C5a activity by PMX205 a peptidic C5aR antagonist is efficacious in preventing DSS-induced colitis, providing further evidence that targeting CD88 in patients with IBD irritable bowel syndrome, ulcerative colitis, Crohn's disease, inflammatory bowel disease (IBD) (Johswich, K., et al. (2009) Inflamm Bowel Dis 15(12): 1812-1823) could be of therapeutic benefit (Woodruff, T. M., et al. (2003) J Immunol 171(10): 5514-5520; Jain, U., et al. (2013) Br J Pharmacol 168(2): 488-501).

There is a body of evidence suggesting a role for C5a and its receptor in pathologies of the CNS. C5aR expression is upregulated on reactive astrocytes, microglia, and endothelial cells in an inflamed human central nervous system (O'Barr, S. A., et al. (2001) J Immunol 166(6): 4154-4162; Gasque, P., et al. (1997) Am J Pathol 150(1): 31-41) and C5a has been reported to be involved in the pathogenesis of many neurodegenerative diseases, such as amyotrophic lateral sclerosis (ALS) (Mantovani, S., et al. (2014) J Neuroimmunol 276(1-2): 213-218; Humayun, S., et al. (2009) J Neuroimmunol 210(1-2): 52-62; Woodruff, T. M., et al. (2008) J Immunol 181(12): 8727-8734), Alzheimer disease (Fonseca, M. I., et al. (2013) J Neuroinflammation 10: 25; Ager, R. R., et al. (2010) J Neurochem 113(2): 389-401), Parkinson's disease (Wang, X. J., et al. (2007) Neurochem Int 50(1): 39-50) and Huntington's disease (Singhrao et al. (1999) Experimental Neurology 159, 362-376). Furthermore C5a is found to be elevated in the CSF of Guillain-Barre syndrome patients (Hartung, H. P., et al. (1987) Neurology 37(6): 1006-1009; Wakerley, B. R. and N. Yuki (2015) Expert Rev Neurother 15(8): 847-849) and an anti C5 antibody was found to be effective in reducing neuropathy in the mouse (Halstead, S. K., et al. (2008) Brain 131 (Pt 5): 1197-1208; Basta, M. and D. R. Branch (2014) Clin Exp Immunol 178 Suppl 1: 87-88). Also, inhibition of the C5a receptor alleviates experimental CNS lupus (Zwirner, J., et al. (1999) Mol Immunol 36(13-14): 877-884; Jacob, A., B. Hack, et al. (2010) J Neuroimmunol 221(1-2): 46-52). Therefore, C5aR antagonists provided herein may be to treat ALS, Alzheimer's disease, multiple sclerosis, Guillain-Barre syndrome, Parkinson's disease, Huntington's disease and also cognitive function decline associated with cardiopulmonary bypass surgery and related procedures in addition to central nervous system involvement in diseases such as SLE, Sjögren's syndrome and associated immunological profiles.

In many autoimmune diseases Immunoglobulin G-containing immune complex (IC) depositions are found. These contribute to the pathophysiology of the diseases which frequently manifest in different organs of the body including the kidneys, heart, lungs, liver, blood vessels, the nervous system and the skin. There are numerous such IC diseases and examples are systemic lupus erthyematosus (SLE), cryoglobulinemia, rheumatoid arthritis, Sjögren's syndrome (Lawley, T. J., et al. (1979) J Immunol 123(3): 1382-1387), Goodpasture syndrome (antiglomerular basement antibody disease), and hypersensitivity. Immune complexes are known to induce C5 convertases leading to C5a production which subsequently contributes to these diseases (Karsten, C. M. and J. Kohl (2012) Immunobiology 217(11): 1067-1079). In animal models reproducing the mechanisms of IC activation of complement, C5aR has been shown to play an important role. Studies show that C5aR deficient mice and the use of a peptidic C5aR antagonist result in protection from tissue injury induced by ICs. (Strachan, A. J., et al. (2000) J Immunol 164(12): 6560-6565; Kohl, J. and J. E. Gessner (1999) Mol Immunol 36(13-14): 893-903; Baumann, U., et al. (2000) J Immunol 164(2): 1065-1070). Therefore, inhibitors of C5aR could be useful to treat IC diseases including the autoimmune diseases rheumatoid arthritis (Jose, P. J., et al. (1990) Ann Rheum Dis 49(10): 747-752; Grant, E. P., et al. (2002) J Exp Med 196(11): 1461-1471; Yuan, G., et al. (2003) Chin Med J (Engl) 116(9): 1408-1412)), osteoarthritis, systemic lupus erythematosus (Porcel, J. M., et al. (1995) Clin Immunol Immunopathol 74(3): 283-288; Pawaria, S., et al. (2014) J Immunol 193(7): 3288-3295), lupus nephritis (Bao, L., et al. (2005) Eur J Immunol 35(8): 2496-2506), lupus glomerulonephritis and IgA nephropathy (Liu, L., et al. (2014) J Clin Immunol 34(2): 224-232), Heyman nephritis, membranous nephritis and other forms of glomerulonephritis, vasculitis, dermatomyositis (Fiebiger, E., et al. (1998) J Clin Invest 101(1): 243-251), pemphigus, systemic sclerosis (scleroderma) (Sprott, H., et al. (2000) J Rheumatol 27(2): 402-404), bronchial asthma, autoimmune hemolytic and thrombocytopenic states, Goodpasture's syndrome (and associated glomerulonephritis and pulmonary hemorrhage) (Ma, R., et al. (2013) J Clin Immunol 33(1): 172-178), immunovasculitis, and complement mediated thrombotic microangiopathies including atypical haemolytic uremic syndrome (Song, D., et al. (2015) Am J Reprod Immunol 74(4): 345-356; Davin, J. C., N. C. van de Kar (2015) Ther Adv Hematol 6(4): 171-185), mixed cryoglubulinemia, atopic dermatitis (Neuber, K., R. et al. (1991) Immunology 73(1): 83-87; Dang, L., et al. (2015) Mol Med Rep 11(6):

4183-4189), and chronic urticaria (Kaplan, A. P. (2004) J Allergy Clin Immunol 114(3): 465-474; Yan, S., et al. (2014) J Dermatol Sci 76(3): 240-245). Furthermore, the compound eculizumab has been shown to have potential utility for the treatment of myasthenia gravis, and anti-phospholipid syndrome.

C5a is present in psoriatic plaques and C5aR expression has also been reported in psoriasis where T cells, neutrophils mast cells and dendritic cells are involved in pathogenesis of the disease and are chemotactic to C5a (Diani, M., G. Altomare and E. Reali (2015) Autoimmun Rev 14(4): 286-292). Neutrophil accumulation under the stratum corneum is observed in the highly inflamed areas of psoriatic plaques, and psoriatic lesion (scale) extracts contain highly elevated levels of C5a and exhibit potent chemotactic activity towards neutrophils, an effect that can be inhibited by addition of a C5a antibody. Furthermore, T cells and neutrophils are chemo-attracted by C5a under certain conditions (Nataf, S., et al. (1999) J Immunol 162(7): 4018-4023; Tsuji, R. F., et al. (2000) J Immunol 165(3): 1588-1598; Werfel, T., et al. (1997) Arch Dermatol Res 289(2): 83-86; Mrowietz, U., et al. (2001) Exp Dermatol 10(4): 238-245) meaning C5aR antagonists may be of benefit in treating psoriasis. Furthermore, complement has been implicated in the pathogenesis of glaucoma (Howell et al. (2011), J. Clin. Invest. 121(4): 1429-1444). In addition, there is experimental evidence to suggest a beneficial role of C5aR antagonists in treating cancer with checkpoint blockers. For example, an antibody against the C5aR receptor (IPH5401) has been reported to be efficacious in muring models of cancer (web page Innate Pharma—IPH5401, 2018; https://www.innate-pharma.com/en/pipeline/iph5401-first-class-anti-c5ar-mab; Zah H., et al. (2017) Oncoimmunology 6(10): e1349587; Wang Y., et al., (2016) Cancer Discovery 6(9) 1022-1035).

Thus, C5a and C5aR are believed to be clinically implicated in vasculitic diseases or disorders, inflammatory diseases or disorders involving intravascular microvesicle release, immune complex (IC) diseases or disorders, neurodegenerative diseases or disorders, complement related inflammatory diseases or disorders, bullous diseases or disorders, diseases or disorders related to ischemia and/or ischemic reperfusion injury, inflammatory bowel diseases or disorders, and autoimmune diseases or disorders; as well as in contact sensitivity or an inflammation caused by contact with artificial surfaces; increased leukocyte and platelet activation (and infiltration to tissues thereof); pathologic sequelae associated to an intoxication or an injury such as a trauma, an hemorrhage, a shock, or surgery including transplantation, including multiple organ failure (MOF), septic shock, shock due to intoxication, or acute lung inflammatory injury; pathologic sequelae associated with insulin-dependent diabetes mellitus; myocardial infarction or thrombosis; edema or an increased capillary permeability; reduction of coronary endothelial dysfunction induced by cardiopulmonary bypass and/or cardioplegia, or cancer.

There is therefore a requirement for new small organic molecule modulators of the C5a receptor (C5aR), especially antagonists of the C5aR, that could be useful for inhibiting pathogenic events associated with elevated levels of C5a and/or with C5aR activation.

Certain PDE4 mediators are disclosed in WO2008/084223. Antiviral quinazolones are disclosed in WO2007/028789. Gonadotropin releasing hormone antagonists are disclosed in WO2005/019188. Certain amino-substituted dihydropyrimido[4,5-d]pyrimidones are disclosed in WO2000/024744. 3,4-Dihydro-quinazoline derivatives that are substituted in position 4 are disclosed as anticholinergic medicaments in WO2000/023436/EP1122253. Certain tert-butyl 4-[1-benzyl-2-oxo-1,4-dihydropyridopyrimidin-3-yl] piperidine-1-carboxylate derivatives are disclosed as synthetic intermediates e.g. in WO2004/092166, WO2005/013894, WO2007/146349, WO2009/020470.

The present invention provides cyclic urea derivatives of formula (I) which are modulators of the C5a receptor, and are useful for the prevention or treatment of diseases which respond to the C5a receptor.

1) A first aspect of the invention relates to compounds of the formula (I)

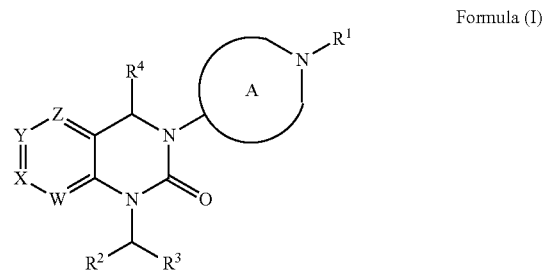

Formula (I)

wherein

W represents N, or $CR^5$ wherein $R^5$ represents hydrogen or $(C_{1-3})$alkoxy (especially methoxy); and X, Y and Z independently represent CH or N [notably W represents $CR^5$; and X, Y and Z independently represent CH];

ring A represents an unsubstituted, saturated 4- to 7-membered mono-cyclic carbocyclic ring containing the ring nitrogen atom to which $R^1$ is attached [especially such ring A is azetidin-1,3-diyl, pyrrolidin-1,3-diyl, piperidin-1,4-diyl, azepan-1,4-diyl];

$R^1$ represents phenyl; 5-membered heteroaryl (which is pyrazolyl); or 6-membered heteroaryl (which is pyridinyl);
wherein said phenyl, 5-membered heteroaryl or 6-membered heteroaryl independently is mono-, di- or tri-substituted (especially mono-, or di-substituted, in particular mono- or di-substituted in ortho position with regard to the point of attachment of the rest of the molecule), wherein the substituents are independently selected from
$(C_{1-4})$alkyl (especially methyl, isopropyl);
$(C_{1-4})$alkoxy (especially methoxy);
$(C_{1-3})$fluoroalkyl (especially trifluoromethyl);
$(C_{1-3})$fluoroalkoxy (especially trifluoromethoxy);
halogen (especially fluoro and chloro);
cyano;
$(C_{3-6})$cycloalkyl (especially cyclopropyl);

$R^2$ represents phenyl; 5-membered heteroaryl (which is thiazolyl); or 6-membered heteroaryl (in particular pyridinyl, pyrimidinyl, pyrazinyl, pyridazinyl);
wherein said phenyl, 5-membered heteroaryl, or 6-membered heteroaryl independently is mono-, or di-substituted (especially mono-substituted, in particular mono-substituted in ortho position with regard to the point of attachment of the rest of the molecule), wherein the substituents are independently selected from
$(C_{1-4})$alkyl (especially methyl, isopropyl);
$(C_{1-4})$alkoxy (especially methoxy, ethoxy, isopropoxy);
$(C_{1-3})$fluoroalkyl (especially trifluoromethyl);
$(C_{1-3})$fluoroalkoxy (especially trifluoromethoxy);
halogen (especially chloro, fluoro);
hydroxy-$(C_{2-3})$alkoxy (especially 2-hydroxy-ethoxy);

($C_{1-3}$)alkyl-carbonyl-oxy-($C_{2-3}$)alkoxy (especially 2-(acetoxy)-ethoxy);

cyano-($C_{1-2}$)alkoxy (especially cyano-methoxy);

($C_{3-6}$)cycloalkyl-$X^{21}$—, wherein $X^{21}$ represents a direct bond, —O—, or —($C_{1-3}$)alkylene-O—, and wherein the ($C_{3-6}$)cycloalkyl independently contains one optional ring oxygen atom; [especially such group ($C_{3-6}$)cycloalkyl-$X^{21}$— is cyclopropyl, cyclopropyl-oxy, cyclobutyl-oxy, oxetan-3-yl-oxy, cyclopropyl-methoxy, tetrahydropyran-4-yl-oxy]; or $R^{21a}R^{21b}N$—($C_{2-3}$)alkylene-O—, wherein $R^{21}$ and $R^{21b}$ independently represent hydrogen or ($C_{1-4}$)alkyl (especially methyl); [especially such group $R^{21a}R^{21b}N$—($C_{2-3}$)alkylene-O— is dimethylamino-ethoxy];

$R^3$ represents hydrogen, ($C_{1-3}$)alkyl (especially methyl), or ($C_{1-3}$)alkoxy-carbonyl (especially methoxycarbonyl); and $R^4$ represents hydrogen, or ($C_{1-4}$)alkyl (especially methyl).

The compounds of formula (I) may contain one or more further stereogenic or asymmetric centers, such as one or more additional asymmetric carbon atoms. The compounds of formula (I) may thus be present as mixtures of stereoisomers or preferably as pure stereoisomers. Mixtures of stereoisomers may be separated in a manner known to a person skilled in the art.

In case a particular compound (or generic structure) is designated as (R)- or (S)-enantiomer/as having an absolute (R)- or (S)-configuration, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center. In analogy, cis- or trans-designations (or (R*,R*) designations) are to be understood as referring to the respective stereoisomer of the respective relative configuration in enriched form, especially in essentially pure form.

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

In some instances, the compounds of formula (I) may contain tautomeric forms. Such tautomeric forms are encompassed in the scope of the present invention. For example, in case the present compounds may contain heteroaromatic aromatic rings containing unsubstituted ring nitrogen atoms having a free valency such as pyrazolyl, such rings may be present in tautomeric forms. For example, the group pyrazol-3-yl represents the tautomeric forms 1H-pyrazol-3-yl and 2H-pyrazol-3-yl.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life and/or reduced dosage requirements, and/or may lead to a modified metabolism pathway, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

In this patent application, a bond drawn as a dotted line shows the point of attachment of the radical drawn. For example, the radical drawn below

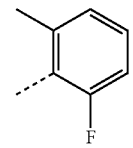

is a 2-fluoro-6-methyl-phenyl group.

Where the plural form is used for compounds, salts, pharmaceutical compositions, diseases and the like, this is intended to mean also a single compound, salt, or the like.

Any reference to compounds of formula (I) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of formula (I), as defined in any one of embodiments 1) to 17), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein. If not explicitly defined otherwise in the respective embodiment or claim, groups defined herein are unsubstituted.

The term "halogen" means fluorine, chlorine, bromine, or iodine, preferably fluorine or chlorine.

The term "alkyl", used alone or in combination, refers to a saturated straight or branched chain hydrocarbon group containing one to six carbon atoms. The term "$(C_{x-y})$alkyl" (x and y each being an integer), refers to an alkyl group as defined before, containing x to y carbon atoms. For example a $(C_{1-6})$alkyl group contains from one to six carbon atoms. Examples of alkyl groups are methyl, ethyl, propyl, isopropyl, butyl, isobutyl, tert.-butyl, 3-methyl-butyl, 2,2-dimethyl-propyl and 3,3-dimethyl-butyl. Examples of $C_{(1-4)}$ alkyl are methyl, ethyl, propyl, isopropyl, butyl, isobutyl, sec.-butyl and tert.-butyl. For avoidance of any doubt, in case a group is referred to as e.g. propyl or butyl, it is meant to be n-propyl, respectively n-butyl. Further, in case a group is referred to as $(C_{0-y})$alkyl group, such group is absent and any free valency of the point of attachment is filled with hydrogen, or it contains up to y carbon as set out before. Preferred are methyl, ethyl and isopropyl. Most preferred is methyl and isopropyl. Examples of $(C_{1-4})$alkyl as used for $R^1$ being attached to phenyl, 5- or 6-membered heteroaryl is methyl. Examples of $(C_{1-4})$alkyl as used for $R^2$ being attached to phenyl, 5- or 6-membered heteroaryl are methyl and isopropyl. Examples of $(C_{1-4})$alkyl as used for $R^3$ is methyl. Examples of $(C_{1-4})$alkyl as used for $R^4$ is methyl.

The term "—$(C_{x-y})$alkylene-", used alone or in combination, refers to bivalently bound alkyl group as defined before containing x toy carbon atoms. Preferably, the points of attachment of a —$(C_{1-y})$alkylene group are in 1,1-diyl, in 1,2-diyl, or in 1,3-diyl arrangement. Preferably, the points of attachment of a —$(C_{2-y})$alkylene group are in 1,2-diyl or in 1,3-diyl arrangement. A —$(C_0)$alkylene- group is absent and refers to a direct bond.

Alkylene-oxy linker groups —$(C_{1-3})$alkylene-O— as used for example in the substituents $(C_{3-6})$cycloalkyl-$X^{21}$— are to be read from left to right, i.e. they refer to the respective $(C_{3-6})$cycloalkyl-$(C_{1-3})$alkylene-O— groups. An example for $(C_{3-6})$cycloalkyl-$X^{21}$— wherein $X^{21}$ is —$(C_{1-3})$alkylene-O— is cyclopropyl-methoxy. An example for $R^{21a}R^{21b}$N—$(C_{2-3})$alkylene-O— is dimethylamino-ethoxy.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are isopropoxy, ethoxy and methoxy. Examples of $(C_{1-4})$alkoxy as used for $R^1$ being attached to phenyl, 5- or 6-membered heteroaryl is methoxy. Examples of $(C_{1-4})$alkoxy as used for $R^2$ being attached to phenyl, 5- or 6-membered heteroaryl are methoxy, ethoxy, isopropoxy.

The term "fluoroalkyl", used alone or in combination, refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$fluoroalkyl groups such as trifluoromethyl. Examples of $(C_{1-4})$fluoroalkyl as used for $R^1$ being attached to phenyl, 5- or 6-membered heteroaryl is trifluoromethyl. Examples of $(C_{1-4})$fluoroalkyl as used for $R^2$ being attached to phenyl, 5- or 6-membered heteroaryl is trifluoromethyl.

The term "fluoroalkoxy", used alone or in combination, refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$ fluoroalkoxy groups such as trifluoromethoxy. Examples of $(C_{1-4})$fluoroalkoxy as used for $R^1$ being attached to phenyl, 5- or 6-membered heteroaryl is trifluoromethoxy. Examples of $(C_{1-4})$ fluoroalkoxy as used for $R^2$ being attached to phenyl, 5- or 6-membered heteroaryl is trifluoromethoxy.

The term "cyano" refers to a group —CN.

The term "cyano-$(C_{1-2})$alkoxy" is to be read from left to right, i.e. it refers to the respective cyano-$(C_{1-2})$alkylene-O— group. An example for cyano-$(C_{1-2})$alkoxy is cyano-methoxy.

The term "cycloalkyl", used alone or in combination, refers to a saturated monocyclic hydrocarbon ring containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of cycloalkyl groups are cyclopropyl, cyclobutyl, cyclopentyl, cyclohexyl, and cycloheptyl. Preferred are cyclopropyl and cyclobutyl; especially cyclopropyl. Examples of $(C_{3-6})$cycloalkyl as used for $R^1$ being attached to phenyl, 5- or 6-membered heteroaryl is cyclopropyl. Examples of $(C_{3-6})$cycloalkyl as used for $R^2$ being attached to phenyl, 5- or 6-membered heteroaryl is cycloptopyl and cyclobutyl.

The term "$(C_{3-6})$cycloalkyl-0" as used for example in the substituents $(C_{3-6})$cycloalkyl-$X^{21}$— wherein $X^{21}$ is —O— relates to $(C_{3-6})$cycloalkyl as defined above, attached via an —O— linker. Examples of $(C_{3-6})$cycloalkyl-O— as used for $R^2$ being attached to phenyl, 5- or 6-membered heteroaryl is cyclopropyl-oxy and cyclobutyl-oxy.

The term "cycloalkyl optionally containing one ring oxygen atom", used alone or in combination, refers to a cycloalkyl group as defined before. In addition, one ring carbon atom of said cycloalkyl may be replaced by an oxygen atom. Examples of such groups are especially cycloalkyl groups such as cyclopropyl, cyclobutyl, cyclopentyl, cyclohexyl, and cycloheptyl; as well as oxygen containing groups such as oxetanyl, tetrahydrofuranyl, and tetrahydro-2H-pyranyl. Examples of optionally substituted $(C_{3-6})$cycloalkyl-O— groups optionally containing one ring oxygen atom as used for the substituent $R^2$ are cyclopropyl, cyclopropyl-oxy, cyclobutyl-oxy, oxetan-3-yl-oxy, cyclopropyl-methoxy, tetrahydropyran-4-yl-oxy.

The substituent phenyl of $R^1$ independently is mono- or di-substituted, in particular (mono- or) di-substituted in ortho-position. An example for mono-substituted phenyl is 2-methoxy-phenyl. Examples for di-substituted phenyl are 2-chloro-6-methyl-phenyl, 2-fluoro-6-methyl-phenyl, 2,6-dimethyl-phenyl, 2,6-difluoro-phenyl, 2-fluoro-6-methoxy-phenyl, 2-methoxy-6-methyl-phenyl, 2-cyano-6-fluoro-phenyl, 2,6-dimethoxy-phenyl, 2-fluoro-6-trifluoromethyl-phenyl, or 2-fluoro-6-trifluoromethoxy-phenyl. The substituent phenyl of $R^2$ is especially mono-substituted, in particular mono-substituted in ortho-position. Examples for mono-substituted phenyl are 2-chloro-phenyl, 2-methoxy-phenyl, 2-cyclopropyl-phenyl, 2-isopropyl-phenyl, 2-ethoxy-phenyl, 2-trifluoro-phenyl, 2-(2-hydroxy-ethoxy)-phenyl, 2-isopropoxy-phenyl, 2-cyanomethoxy-phenyl, 2-cyclopropoxy-phenyl, 2-(oxetan-3-yloxy)-phenyl, 2-cyclopropylmethoxy-phenyl, 2-cyclobutyloxy-phenyl, 2-trifluoromethoxy-phenyl, 2-(2-dimethylamino-ethoxy)-phenyl, 2-(tetrahydro-pyran-4-yloxy)-phenyl, or 2-(2-acethoxy)-ethoxy)-phenyl.

The term "heteroaryl", used alone or in combination, means a 5- to 6-membered monocyclic aromatic ring containing one to two heteroatoms, each independently selected from oxygen, nitrogen and sulfur. Examples of such heteroaryl groups are furanyl, oxazolyl, isoxazolyl, thiophenyl, thiazolyl, isothiazolyl, pyrrolyl, imidazolyl, pyrazolyl, pyridinyl, pyrimidinyl, pyridazinyl, and pyrazinyl. The above-mentioned heteroaryl groups are unsubstituted or substituted as explicitly defined. Notably, the term refers to 5-membered heteroaryl containing at least one nitrogen atom and optionally one further heteroatom selected from nitrogen, oxygen or sulfur; such as especially pyrazolyl, or thiazolyl; or to 6-membered heteroaryl containing one or two nitrogen atoms; such as pyrimidinyl, pyrazinyl, pyridazinyl or pyridinyl. In case 5- or 6-membered heteroaryl group is substituted in ortho-position with regard to the point of attachment of the rest of the molecule, it is understood that such substituent is attached in direct neighbourhood with regard to the point of attachment of the rest of the molecule, i.e. in a relative 1,2-arrangement. For the substituent $R^1$, such 5- or 6-membered heteroaryl group is mono-,di- or tri-substituted (especially mono-, or di-substituted, in particular mono- or di-substituted in ortho-position) wherein the substituents are independently selected from $(C_{1-4})$alkyl; $(C_{1-4})$alkoxy; $(C_{1-3})$fluoroalkyl; $(C_{1-3})$fluoroalkoxy; halogen; cyano and $(C_{3-6})$cycloalkyl. In a sub-embodiment, the substituents are independently selected from methyl, methoxy, trifluoromethyl, trifluoromethoxy, fluoro, chloro, cyano and cyclopropyl. Examples for $R^1$ are 4-chloro-2,5-dimethyl-2H-pyrazol-3-yl, 2-fluoro-4-methyl-pyridin-3-yl, 2,4-dimethyl-pyridin-3-yl, 2-methoxy-4-methyl-pyridin-3-yl, 4-cyano-2,5-dimethyl-pyrazol-2-yl, or 4-chloro-5-cyclopropyl-2-methyl-pyrazol-2-yl. For the substituent $R^2$, such 5- or 6-membered heteroaryl group is mono- or di-substituted (especially mono-substituted, in particular mono-substituted in ortho-position) wherein the substituents are independently selected from $(C_{1-4})$alkyl; $(C_{1-4})$alkoxy; $(C_{1-3})$fluoroalkyl; $(C_{1-3})$fluoroalkoxy; halogen; hydroxy-$(C_{2-3})$alkoxy, $(C_{1-3})$alkyl-carbonyl-oxy-$(C_{2-3})$alkoxy, cyano-$(C_{1-2})$alkoxy, $(C_{3-6})$cycloalkyl, $(C_{3-6})$cycloalkyl-O—, or $(C_{3-6})$cycloalkyl-$CH_2$—O—. Examples for $R^2$ are 3-methoxy-pyrazin-2-yl, 3-isopropyl-pyrazin-2-yl, 4-isopropyl-pyrimidin-5-yl, 4-isopropyl-pyridin-3-yl, 3-trifluoromethyl-pyrazin-2-yl, 4-isopropoxy-pyridazin-3-yl, 3-isopropoxy-pyrazin-2-yl, 3-trifluoromethyl-pyridin-2-yl, 4-trifluoromethyl-pyridin-3-yl, 2-trifluoromethyl-pyridin-3-yl, 2-methyl-4-trifluoromethyl-thiazol-5-yl, or 3-isopropoxy-pyridin-2-yl.

Further embodiments of the invention are presented hereinafter:

2) A second embodiment relates to compounds according to embodiment 1), wherein ring A represents a saturated 4- to 7-membered mono-cyclic carbocyclic ring containing the ring nitrogen atom to which $R^1$ is attached, wherein said ring is selected from azetidin-1,3-diyl, pyrrolidin-1,3-diyl, piperidin-1,4-diyl, and azepan-1,4-diyl.

3) Another embodiment relates to compounds according to embodiment 1), wherein ring A represents pyrrolidin-1,3-diyl, or piperidin-1,4-diyl (especially piperidin-1,4-diyl).

4) Another embodiment relates to compounds according to any one of embodiments 1) to 3), wherein
W, X, Y and Z all represent CH;
W represents $CR^5$ wherein $R^5$ represents $(C_{1-3})$alkoxy (especially methoxy); and X, Y and Z all represent CH;
W represents $CR^5$ wherein $R^5$ represents hydrogen or $(C_{1-3})$alkoxy (especially methoxy); one of X, Y and Z represents N, and the remaining of X, Y and Z represent CH;
W represents N; and X, Y and Z all represent CH;
two of W, X, Y and Z represent N, and the remaining of W, X, Y and Z represent CH.

5) Another embodiment relates to compounds according to any one of embodiments 1) to 3), wherein
W, X, Y and Z all represent CH;
W represents $CR^5$ wherein $R^5$ represents $(C_{1-3})$alkoxy (especially methoxy); and X, Y and Z all represent CH;
two of W, X, Y and Z represent N, and the remaining of W, X, Y and Z represent CH (especially W and Z are N and X and Y are CH).

6) Another embodiment relates to compounds according to any one of embodiments 1) to 5), wherein
$R^1$ represents
phenyl which is mono-, or di- or tri-substituted (notably mono- or di-substituted, wherein at least one substituent is attached in ortho position with regard to the point of attachment of the rest of the molecule; especially di-substituted in ortho position), wherein the substituents are independently selected from:
$(C_{1-4})$alkyl (especially methyl, isopropyl);
$(C_{1-4})$alkoxy (especially methoxy);
$(C_{1-3})$fluoroalkyl (especially trifluoromethyl);
$(C_{1-3})$fluoroalkoxy (especially trifluoromethoxy);
halogen (especially fluoro or chloro);
cyano; and
$(C_{3-6})$cycloalkyl (especially cyclopropyl); or
pyrazolyl (especially 2H-pyrazol-3-yl) which is mono-, or di- or tri-substituted (notably tri-substituted), wherein the substituents are independently selected from:
$(C_{1-4})$alkyl (especially methyl);
halogen (especially chloro);
cyano; and
$(C_{3-6})$cycloalkyl (especially cyclopropyl); or
pyridinyl which is mono-, or di- or tri-substituted (notably mono- or di-substituted, wherein at least one substituent is attached in ortho position with regard to the point of attachment of the rest of the molecule; especially di-substituted in ortho position), wherein the substituents are independently selected from:
$(C_{1-4})$alkyl (especially methyl, isopropyl);
$(C_{1-4})$alkoxy (especially methoxy);
halogen (especially fluoro);
cyano; and
$(C_{3-6})$cycloalkyl (especially cyclopropyl).

7) Another embodiment relates to compounds according to any one of embodiments 1) to 5), wherein
$R^1$ represents
phenyl which is mono- or di-substituted, wherein at least one substituent is attached in ortho position with regard to the point of attachment of the rest of the molecule (especially di-substituted in ortho position), wherein the substituents are independently selected from:

($C_{1-4}$)alkyl (especially methyl, isopropyl);
($C_{1-4}$)alkoxy (especially methoxy);
($C_{1-3}$)fluoroalkyl (especially trifluoromethyl);
($C_{1-3}$)fluoroalkoxy (especially trifluoromethoxy);
halogen (especially fluoro or chloro);
cyano; and
($C_{3-6}$)cycloalkyl (especially cyclopropyl);
pyrazolyl (especially 2H-pyrazol-3-yl) which is tri-substituted, wherein two of said substituents are independently selected from:
($C_{1-4}$)alkyl (especially methyl); and
($C_{3-6}$)cycloalkyl (especially cyclopropyl);
and the remaining of said substituents is independently halogen (especially chloro) or cyano; or
pyridinyl which is di-substituted, wherein at least one substituent is attached in ortho position with regard to the point of attachment of the rest of the molecule (especially di-substituted in ortho position), wherein the substituents are independently selected from:
($C_{1-4}$)alkyl (especially methyl, isopropyl);
($C_{1-4}$)alkoxy (especially methoxy); and
halogen (especially fluoro).

8) Another embodiment relates to compounds according to any one of embodiments 1) to 5), wherein
$R^1$ represents
phenyl which is mono- or di-substituted, wherein at least one substituent is attached in ortho position with regard to the point of attachment of the rest of the molecule (especially di-substituted in ortho position), wherein the substituents are independently selected from:
($C_{1-4}$)alkyl (especially methyl, isopropyl);
($C_{1-4}$)alkoxy (especially methoxy);
($C_{1-3}$)fluoroalkyl (especially trifluoromethyl);
($C_{1-3}$)fluoroalkoxy (especially trifluoromethoxy);
halogen (especially fluoro or chloro);
cyano; and
($C_{3-6}$)cycloalkyl (especially cyclopropyl); or
pyridinyl which is di-substituted, wherein at least one substituent is attached in ortho position with regard to the point of attachment of the rest of the molecule (especially di-substituted in ortho position), wherein the substituents are independently selected from:
($C_{1-4}$)alkyl (especially methyl, isopropyl);
($C_{1-4}$)alkoxy (especially methoxy); and
halogen (especially fluoro).

9) Another embodiment relates to compounds according to any one of embodiments 1) to 5), wherein
$R^1$ represents
phenyl which is mono- or di-substituted, wherein at least one substituent is attached in ortho position with regard to the point of attachment of the rest of the molecule (especially di-substituted in ortho position), wherein the substituents are independently selected from:
($C_{1-4}$)alkyl (especially methyl, isopropyl);
($C_{1-4}$)alkoxy (especially methoxy);
halogen (especially fluoro or chloro); and
cyano; or
pyridinyl which is di-substituted, wherein at least one substituent is attached in ortho position with regard to the point of attachment of the rest of the molecule (especially di-substituted in ortho position), wherein the substituents are independently selected from:
($C_{1-4}$)alkyl (especially methyl, isopropyl);
($C_{1-4}$)alkoxy (especially methoxy); and
halogen (especially fluoro).

10) Another embodiment relates to compounds according to any one of embodiments 1) to 5), wherein
$R^1$ represents phenyl which is mono-, or di-substituted; wherein at least one substituent is attached in ortho position with regard to the point of attachment of the rest of the molecule;
wherein said ortho-substituent is
($C_{1-4}$)alkyl (especially methyl);
($C_{1-4}$)alkoxy (especially methoxy); or
halogen (especially fluoro);
[especially such substituent is methyl, methoxy or fluoro; in particular methyl];
and, if present, the remaining substituent is independently selected from:
methyl;
methoxy;
halogen (especially fluoro); and
cyano;
[especially such remaining substituent is methyl, methoxy or fluoro; in particular methyl];
wherein especially such remaining substituent is attached in the other ortho position with regard to the point of attachment of the rest of the molecule.

11) Another embodiment relates to compounds according to any one of embodiments 1) to 10), wherein
$R^2$ represents phenyl; wherein said phenyl is mono-, or di-substituted (especially mono-substituted, in particular mono-substituted in ortho position with regard to the point of attachment of the rest of the molecule), wherein the substituents are independently selected from
($C_{1-4}$)alkyl (especially methyl, isopropyl);
($C_{1-4}$)alkoxy (especially methoxy, ethoxy, isopropoxy);
($C_{1-3}$)fluoroalkyl (especially trifluoromethyl);
($C_{1-3}$)fluoroalkoxy (especially trifluoromethoxy);
halogen (especially chloro, fluoro);
hydroxy-($C_{2-3}$)alkoxy (especially 2-hydroxy-ethoxy);
($C_{1-3}$)alkyl-carbonyl-oxy-($C_{2-3}$)alkoxy (especially 2-(acetoxy)-ethoxy);
cyano-($C_{1-2}$)alkoxy (especially cyano-methoxy);
($C_{3-6}$)cycloalkyl-$X^{21}$—, wherein $X^{21}$ represents a direct bond, —O—, or —($C_{1-3}$)alkylene-O—, and wherein the ($C_{3-6}$)cycloalkyl independently contains one optional ring oxygen atom; [especially such group ($C_{3-6}$)cycloalkyl-$X^{21}$— is cyclopropyl, cyclopropyl-oxy, cyclobutyl-oxy, oxetan-3-yl-oxy, cyclopropyl-methoxy, tetrahydropyran-4-yl-oxy]; and
$R^{21a}R^{21b}$N—($C_{2-3}$)alkylene-O—, wherein $R^{21a}$ and $R^{21b}$ independently represent hydrogen or ($C_{1-4}$) alkyl (especially methyl); [especially such group $R^{21a}R^{21b}$N—($C_{2-3}$)alkylene-O— is dimethylamino-ethoxy];
or $R^2$ represents thiazolyl (especially thiazol-5-yl); wherein said thiazolyl is mono-, or di-substituted (especially di-substituted), wherein the substituents are independently selected from
($C_{1-4}$)alkyl (especially methyl, isopropyl);
($C_{1-3}$)fluoroalkyl (especially trifluoromethyl); and
($C_{3-6}$)cycloalkyl (especially cyclopropyl);
or $R^2$ represents 6-membered heteroaryl (in particular pyridinyl, pyrimidinyl, pyrazinyl, pyridazinyl); wherein said 6-membered heteroaryl independently is mono-, or di-substituted (especially mono-substituted, in particular mono-substituted in ortho position with regard to the point of attachment of the rest of the molecule), wherein the substituents are independently selected from
($C_{1-4}$)alkyl (especially methyl, isopropyl);

(C$_{1-4}$)alkoxy (especially methoxy, ethoxy, isopropoxy); and (C$_{1-3}$)fluoroalkyl (especially trifluoromethyl).

12) Another embodiment relates to compounds according to any one of embodiments 1) to 10), wherein R$^2$ represents phenyl; wherein said phenyl is mono-, or di-substituted (especially mono-substituted, in particular mono-substituted in ortho position with regard to the point of attachment of the rest of the molecule), wherein the substituents are independently selected from (C$_{1-4}$)alkyl (especially methyl, isopropyl);
(C$_{1-4}$)alkoxy (especially methoxy, ethoxy, isopropoxy);
(C$_{1-3}$)fluoroalkyl (especially trifluoromethyl);
(C$_{1-3}$)fluoroalkoxy (especially trifluoromethoxy);
halogen (especially chloro, fluoro);
hydroxy-(C$_{2-3}$)alkoxy (especially 2-hydroxy-ethoxy);
(C$_{1-3}$)alkyl-carbonyl-oxy-(C$_{2-3}$)alkoxy (especially 2-(acetoxy)-ethoxy);
cyano-(C$_{1-2}$)alkoxy (especially cyano-methoxy);
(C$_{3-6}$)cycloalkyl-X$^{21}$—, wherein X$^{21}$ represents a direct bond, —O—, or —(C$_{1-3}$)alkylene-O—, and wherein the (C$_{3-6}$)cycloalkyl independently contains one optional ring oxygen atom; [especially such group (C$_{3-6}$)cycloalkyl-X$^{21}$— is cyclopropyl, cyclopropyl-oxy, cyclobutyl-oxy, oxetan-3-yl-oxy, cyclopropyl-methoxy, tetrahydropyran-4-yl-oxy]; and
R$^{21a}$R$^{21b}$N—(C$_{2-3}$)alkylene-O—, wherein R$^{21a}$ and R$^{21b}$ independently represent hydrogen or (C$_{1-4}$)alkyl (especially methyl); [especially such group R$^{21a}$R$^{21b}$N—(C$_{2-3}$)alkylene-O— is dimethylamino-ethoxy];

or R$^2$ represents 6-membered heteroaryl (in particular pyridinyl, pyrimidinyl, pyrazinyl, pyridazinyl); wherein said 6-membered heteroaryl independently is mono-, or di-substituted (especially mono-substituted, in particular mono-substituted in ortho position with regard to the point of attachment of the rest of the molecule), wherein the substituents are independently selected from (C$_{1-4}$)alkyl (especially methyl, isopropyl);
(C$_{1-4}$)alkoxy (especially methoxy, ethoxy, isopropoxy); and
(C$_{1-3}$)fluoroalkyl (especially trifluoromethyl).

13) Another embodiment relates to compounds according to any one of embodiments 1) to 10), wherein R$^2$ represents phenyl, which is mono-substituted in ortho position with regard to the point of attachment of the rest of the molecule, wherein the substituent is independently selected from (C$_{1-4}$)alkyl (especially isopropyl);
(C$_{1-4}$)alkoxy (especially methoxy, ethoxy, isopropoxy);
(C$_{1-3}$)fluoroalkyl (especially trifluoromethyl);
(C$_{1-3}$)fluoroalkoxy (especially trifluoromethoxy);
halogen (especially chloro); or
cyclopropyl, cyclopropyl-oxy, tetrahydro-pyran-4-yloxy, cyclopropyl-methoxy;

or R$^2$ represents 6-membered heteroaryl (in particular pyridinyl, pyrimidinyl, pyrazinyl, pyridazinyl); wherein said 6-membered heteroaryl is mono-substituted in ortho position with regard to the point of attachment of the rest of the molecule, wherein the substituent is independently selected from (C$_{1-4}$)alkyl (especially isopropyl);
(C$_{1-4}$)alkoxy (especially methoxy, isopropoxy);
(C$_{1-3}$)fluoroalkyl (especially trifluoromethyl).

14) Another embodiment relates to compounds according to any one of embodiments 1) to 13), wherein R$^3$ represents hydrogen, or methyl (especially hydrogen).

15) Another embodiment relates to compounds according to any one of embodiments 1) to 14), wherein R$^4$ represents hydrogen or methyl (especially hydrogen).

16) The invention, thus, especially relates to compounds of the formula (I) as defined in embodiment 1), and to such compounds further limited by the characteristics of any one of embodiments 2) to 15), under consideration of their respective dependencies; to pharmaceutically acceptable salts thereof; and to the use of such compounds as medicaments especially for use in the prevention/prophylaxis or treatment of diseases and disorders related to pathogenic events associated with elevated levels of C5a and/or with C5aR activation.

For avoidance of any doubt, especially the following embodiments relating to the compounds of formula (I) are thus possible and intended and herewith specifically disclosed in individualized form:

1, 2+1, 3+1, 4+1, 4+2+1, 5+1, 5+3+1, 6+1, 6+2+1, 6+4+1, 6+4+2+1, 7+1, 7+2+1, 7+4+1, 7+4+2+1, 8+1, 8+2+1, 8+4+1, 8+4+2+1, 9+1, 9+3+1, 9+5+1, 9+5+3+1, 10+1, 10+3+1, 10+5+1, 10+5+3+1, 11+1, 11+2+1, 11+4+1, 11+4+2+1, 11+6+1, 11+6+2+1, 11+6+4+1, 11+6+4+2+1, 11+7+1, 11+7+2+1, 11+7+4+1, 11+7+4+2+1, 11+8+1, 11+8+2+1, 11+8+4+1, 11+8+4+2+1, 12+1, 12+3+1, 12+5+1, 12+5+3+1, 12+9+1, 12+9+3+1, 12+9+5+1, 12+9+5+3+1, 12+10+1, 12+10+3+1, 12+10+5+1, 12+10+5+3+1, 13+1, 13+3+1, 13+5+1, 13+5+3+1, 13+9+1, 13+9+3+1, 13+9+5+1, 13+9+5+3+1, 13+10+1, 13+10+3+1, 13+10+5+1, 13+10+5+3+1, 14+1, 14+2+1, 14+3+1, 14+4+1, 14+4+2+1, 14+5+1, 14+5+3+1, 14+6+1, 14+6+2+1, 14+6+4+1, 14+6+4+2+1, 14+7+1, 14+7+2+1, 14+7+4+1, 14+7+4+2+1, 14+8+1, 14+8+2+1, 14+8+4+1, 14+8+4+2+1, 14+9+1, 14+9+3+1, 14+9+5+1, 14+9+5+3+1, 14+10+1, 14+10+3+1, 14+10+5+1, 14+10+5+3+1, 14+11+1, 14+11+2+1, 14+11+4+1, 14+11+4+2+1, 14+11+6+1, 14+11+6+2+1, 14+11+6+4+1, 14+11+6+4+2+1, 14+11+7+1, 14+11+7+2+1, 14+11+7+4+1, 14+11+7+4+2+1, 14+11+8+1, 14+11+8+2+1, 14+11+8+4+1, 14+11+8+4+2+1, 14+12+1, 14+12+3+1, 14+12+5+1, 14+12+5+3+1, 14+12+9+1, 14+12+9+3+1, 14+12+9+5+1, 14+12+9+5+3+1, 14+12+10+1, 14+12+10+3+1, 14+12+10+5+1, 14+12+10+5+3+1, 14+13+1, 14+13+3+1, 14+13+5+1, 14+13+5+3+1, 14+13+9+1, 14+13+9+3+1, 14+13+9+5+1, 14+13+9+5+3+1, 14+13+10+1, 14+13+10+3+1, 14+13+10+5+1, 14+13+10+5+3+1, 15+1, 15+2+1, 15+3+1, 15+4+1, 15+4+2+1, 15+5+1, 15+5+3+1, 15+6+1, 15+6+2+1, 15+6+4+1, 15+6+4+2+1, 15+7+1, 15+7+2+1, 15+7+4+1, 15+7+4+2+1, 15+8+1, 15+8+2+1, 15+8+4+1, 15+8+4+2+1, 15+9+1, 15+9+3+1, 15+9+5+1, 15+9+5+3+1, 15+10+1, 15+10+3+1, 15+10+5+1, 15+10+5+3+1, 15+11+1, 15+11+2+1, 15+11+4+1, 15+11+4+2+1, 15+11+6+1, 15+11+6+2+1, 15+11+6+4+1, 15+11+6+4+2+1, 15+11+7+1, 15+11+7+2+1, 15+11+7+4+1, 15+11+7+4+2+1, 15+11+8+1, 15+11+8+2+1, 15+11+8+4+1, 15+11+8+4+2+1, 15+12+1, 15+12+3+1, 15+12+5+1, 15+12+5+3+1, 15+12+9+1, 15+12+9+3+1, 15+12+9+5+1, 15+12+9+5+3+1, 15+12+10+1, 15+12+10+3+1, 15+12+10+5+1, 15+12+10+5+3+1, 15+13+1, 15+13+3+1, 15+13+5+1, 15+13+5+3+1, 15+13+9+1, 15+13+9+3+1, 15+13+9+5+1, 15+13+9+5+3+1, 15+13+10+1, 15+13+10+3+1, 15+13+10+5+1, 15+13+10+5+3+1, 15+14+1, 15+14+2+1, 15+14+3+1, 15+14+4+1, 15+14+4+2+1, 15+14+5+1, 15+14+5+3+1, 15+14+6+1, 15+14+6+2+1, 15+14+6+4+1, 15+14+6+4+2+1, 15+14+7+1, 15+14+7+2+1, 15+14+7+4+1, 15+14+7+4+2+1, 15+14+8+1, 15+14+8+2+1, 15+14+8+4+1, 15+14+8+4+2+1, 15+14+9+1, 15+14+

9+3+1, 15+14+9+5+1, 15+14+9+5+3+1, 15+14+10+1, 15+14+10+3+1, 15+14+10+5+1, 15+14+10+5+3+1, 15+14+11+1, 15+14+11+2+1, 15+14+11+4+1, 15+14+11+4+2+1, 15+14+11+6+1, 15+14+11+6+2+1, 15+14+11+6+4+1, 15+14+11+6+4+2+1, 15+14+11+7+1, 15+14+11+7+2+1, 15+14+11+7+4+1, 15+14+11+7+4+2+1, 15+14+11+8+1, 15+14+11+8+2+1, 15+14+11+8+4+1, 15+14+11+8+4+2+1, 15+14+12+1, 15+14+12+3+1, 15+14+12+5+1, 15+14+12+5+3+1, 15+14+12+9+1, 15+14+12+9+3+1, 15+14+12+9+5+1, 15+14+12+9+5+3+1, 15+14+12+10+1, 15+14+12+10+3+1, 15+14+12+10+5+1, 15+14+12+10+5+3+1, 15+14+13+1, 15+14+13+3+1, 15+14+13+5+1, 15+14+13+5+3+1, 15+14+13+9+1, 15+14+13+9+3+1, 15+14+13+9+5+1, 15+14+13+9+5+3+1, 15+14+13+10+1, 15+14+13+10+3+1, 15+14+13+10+5+1, 15+14+13+10+5+3+1.

In the list above the numbers refer to the embodiments according to their numbering provided hereinabove whereas "+" indicates the dependency from another embodiment. The different individualized embodiments are separated by commas. In other words, "15+14+9+1" for example refers to embodiment 15) depending on embodiment 14), depending on embodiment 9), depending on embodiment 1), i.e. embodiment "15+14+9+1" corresponds to the compounds of formula (I) according to embodiment 1) further limited by all the features of the embodiments 9), 14), and 15).

17) Another embodiment relates to compounds according to embodiment 1) which are selected from the following compounds:

3-[1-(2,6-Dimethyl-phenyl)-piperidin-4-yl]-1-(2-trifluoromethyl-benzyl)-3,4-dihydro-1H-quinazolin-2-one;
3-[1-(2,6-Difluoro-phenyl)-piperidin-4-yl]-1-(2-trifluoromethyl-benzyl)-3,4-dihydro-1H-quinazolin-2-one;
3-[1-(2,6-Dimethyl-phenyl)-piperidin-4-yl]-8-methoxy-1-(2-trifluoromethyl-benzyl)-3,4-dihydro-1H-quinazolin-2-one;
8-Methoxy-3-[1-(2-methoxy-phenyl)-piperidin-4-yl]-1-(2-trifluoromethyl-benzyl)-3,4-dihydro-1H-quinazolin-2-one;
3-[1-(2-Fluoro-6-methoxy-phenyl)-piperidin-4-yl]-8-methoxy-1-(2-trifluoromethyl-benzyl)-3,4-dihydro-1H-quinazolin-2-one;
3-[1-(2-Methoxy-phenyl)-piperidin-4-yl]-1-(2-trifluoromethyl-benzyl)-3,4-dihydro-1H-quinazolin-2-one;
3-[1-(2-Fluoro-6-methoxy-phenyl)-piperidin-4-yl]-1-(2-trifluoromethyl-benzyl)-3,4-dihydro-1H-quinazolin-2-one;
3-[(R)-1-(2,6-Difluoro-phenyl)-pyrrolidin-3-yl]-8-methoxy-1-(2-trifluoromethyl-benzyl)-3,4-dihydro-1H-quinazolin-2-one;
3-[(R)-1-(2,6-Dimethyl-phenyl)-pyrrolidin-3-yl]-8-methoxy-1-(2-trifluoromethyl-benzyl)-3,4-dihydro-1H-quinazolin-2-one;
8-Methoxy-3-[(R)-1-(2-methoxy-phenyl)-pyrrolidin-3-yl]-1-(2-trifluoromethyl-benzyl)-3,4-dihydro-1H-quinazolin-2-one;
3-[(R)-1-(2-Fluoro-6-methoxy-phenyl)-pyrrolidin-3-yl]-8-methoxy-1-(2-trifluoromethyl-benzyl)-3,4-dihydro-1H-quinazolin-2-one;
3-[1-(4-Chloro-5-cyclopropyl-2-methyl-2H-pyrazol-3-yl)-piperidin-4-yl]-1-(2-trifluoromethyl-benzyl)-3,4-dihydro-1H-quinazolin-2-one;
3-[1-(2-Fluoro-6-methyl-phenyl)-piperidin-4-yl]-1-(2-trifluoromethyl-benzyl)-3,4-dihydro-1H-quinazolin-2-one;
3-[(S)-1-(2,6-Dimethyl-phenyl)-pyrrolidin-3-yl]-1-(2-trifluoromethyl-benzyl)-3,4-dihydro-1H-quinazolin-2-one;
3-[(S)-1-(2,6-Difluoro-phenyl)-pyrrolidin-3-yl]-1-(2-trifluoromethyl-benzyl)-3,4-dihydro-1H-quinazolin-2-one;
3-[(S)-1-(2-Methoxy-phenyl)-pyrrolidin-3-yl]-1-(2-trifluoromethyl-benzyl)-3,4-dihydro-1H-quinazolin-2-one;
3-[(S)-1-(2-Fluoro-6-methoxy-phenyl)-pyrrolidin-3-yl]-1-(2-trifluoromethyl-benzyl)-3,4-dihydro-1H-quinazolin-2-one;
3-[(R)-1-(2,6-Dimethyl-phenyl)-pyrrolidin-3-yl]-1-(2-trifluoromethyl-benzyl)-3,4-dihydro-1H-quinazolin-2-one;
3-[(R)-1-(2,6-Difluoro-phenyl)-pyrrolidin-3-yl]-1-(2-trifluoromethyl-benzyl)-3,4-dihydro-1H-quinazolin-2-one;
3-[(R)-1-(2-Methoxy-phenyl)-pyrrolidin-3-yl]-1-(2-trifluoromethyl-benzyl)-3,4-dihydro-1H-quinazolin-2-one;
3-[(R)-1-(2-Fluoro-6-methoxy-phenyl)-pyrrolidin-3-yl]-1-(2-trifluoromethyl-benzyl)-3,4-dihydro-1H-quinazolin-2-one;
8-Methoxy-3-[(R)-1-(2-methoxy-6-methyl-phenyl)-pyrrolidin-3-yl]-1-(2-trifluoromethyl-benzyl)-3,4-dihydro-1H-quinazolin-2-one;
3-[1-(2-Methoxy-6-methyl-phenyl)-piperidin-4-yl]-1-(2-trifluoromethyl-benzyl)-3,4-dihydro-1H-quinazolin-2-one;
3-[(R)-1-(2,6-Dimethoxy-phenyl)-pyrrolidin-3-yl]-8-methoxy-1-(2-trifluoromethyl-benzyl)-3,4-dihydro-1H-quinazolin-2-one;
8-Methoxy-3-[1-(2-methoxy-6-methyl-phenyl)-piperidin-4-yl]-1-(2-trifluoromethyl-benzyl)-3,4-dihydro-1H-quinazolin-2-one;
3-[(R)-1-(2-Fluoro-6-methyl-phenyl)-pyrrolidin-3-yl]-1-(2-trifluoromethyl-benzyl)-3,4-dihydro-1H-quinazolin-2-one;
3-[(R)-1-(2-Methoxy-6-methyl-phenyl)-pyrrolidin-3-yl]-1-(2-trifluoromethyl-benzyl)-3,4-dihydro-1H-quinazolin-2-one;
3-(2',4'-Dimethyl-3,4,5,6-tetrahydro-2H-[1,3']bipyridinyl-4-yl)-1-(2-trifluoromethyl-benzyl)-3,4-dihydro-1H-quinazolin-2-one;
3-(2'-Methoxy-4'-methyl-3,4,5,6-tetrahydro-2H-[1,3']bipyridinyl-4-yl)-1-(2-trifluoromethyl-benzyl)-3,4-dihydro-1H-quinazolin-2-one:
3-(2'-Fluoro-4'-methyl-3,4,5,6-tetrahydro-2H-[1,3']bipyridinyl-4-yl)-1-(2-trifluoromethyl-benzyl)-3,4-dihydro-1H-quinazolin-2-one;
3-[(R)-1-(2-Methoxy-4-methyl-pyridin-3-yl)-pyrrolidin-3-yl]-1-(2-trifluoromethyl-benzyl)-3,4-dihydro-1H-quinazolin-2-one;
3-[(R)-1-(2,4-Dimethyl-pyridin-3-yl)-pyrrolidin-3-yl]-1-(2-trifluoromethyl-benzyl)-3,4-dihydro-1H-quinazolin-2-one;
3-[(R)-1-(2-Fluoro-4-methyl-pyridin-3-yl)-pyrrolidin-3-yl]-1-(2-trifluoromethyl-benzyl)-3,4-dihydro-1H-quinazolin-2-one;
3-[(R)-1-(2,6-Dimethyl-phenyl)-pyrrolidin-3-yl]-1-(2-methoxy-benzyl)-3,4-dihydro-1H-quinazolin-2-one;
3-[(R)-1-(2-Fluoro-6-methyl-phenyl)-pyrrolidin-3-yl]-1-(2-methoxy-benzyl)-3,4-dihydro-1H-quinazolin-2-one;
3-[1-(2,6-Dimethyl-phenyl)-piperidin-4-yl]-1-(2-methoxy-benzyl)-3,4-dihydro-1H-quinazolin-2-one;
3-[1-(2-Fluoro-6-methyl-phenyl)-piperidin-4-yl]-1-(2-methoxy-benzyl)-3,4-dihydro-1H-quinazolin-2-one;
3-Fluoro-2-{4-[2-oxo-1-(3-trifluoromethyl-pyrazin-2-ylmethyl)-1,4-dihydro-2H-quinazolin-3-yl]-piperidin-1-yl}-benzonitrile;
3-Fluoro-2-{4-[1-(3-methoxy-pyrazin-2-ylmethyl)-2-oxo-1,4-dihydro-2H-quinazolin-3-yl]-piperidin-1-yl}-benzonitrile;
3-[1-(2-Fluoro-6-methyl-phenyl)-piperidin-4-yl]-1-[1-(2-methoxy-phenyl)-ethyl]-3,4-dihydro-1H-quinazolin-2-one;

6-[1-(2-Fluoro-6-methyl-phenyl)-piperidin-4-yl]-8-(2-trifluoromethyl-benzyl)-5,8-dihydro-6H-pyrimido[4,5-c]pyridazin-7-one;

3-[1-(2-Fluoro-6-methyl-phenyl)-piperidin-4-yl]-1-(3-trifluoromethyl-pyrazin-2-ylmethyl)-3,4-dihydro-1H-quinazolin-2-one;

3-[1-(2-Fluoro-6-methyl-phenyl)-piperidin-4-yl]-1-(3-methoxy-pyrazin-2-ylmethyl)-3,4-dihydro-1H-quinazolin-2-one;

3-[1-(2-Fluoro-6-methyl-phenyl)-piperidin-4-yl]-1-(2-isopropoxy-benzyl)-3,4-dihydro-1H-quinazolin-2-one;

3-[1-(2-Fluoro-6-methyl-phenyl)-piperidin-4-yl]-1-[1-(2-trifluoromethyl-phenyl)-ethyl]-3,4-dihydro-1H-quinazolin-2-one;

1-(2-Ethoxy-benzyl)-3-[1-(2-fluoro-6-methyl-phenyl)-piperidin-4-yl]-3,4-dihydro-1H-quinazolin-2-one;

1-[2-(2-Dimethylamino-ethoxy)-benzyl]-3-[1-(2-fluoro-6-methyl-phenyl)-piperidin-4-yl]-3,4-dihydro-1H-quinazolin-2-one;

Acetic acid 2-(2-{3-[1-(2-fluoro-6-methyl-phenyl)-piperidin-4-yl]-2-oxo-3,4-dihydro-2H-quinazolin-1-ylmethyl}-phenoxy)-ethyl ester;

{3-[1-(2-Fluoro-6-methyl-phenyl)-piperidin-4-yl]-2-oxo-3,4-dihydro-2H-quinazolin-1-yl}-(2-methoxy-phenyl)-acetic acid methyl ester;

3-[1-(2-Fluoro-6-methyl-phenyl)-piperidin-4-yl]-1-[2-(2-hydroxy-ethoxy)-benzyl]-3,4-dihydro-1H-quinazolin-2-one;

3-[1-(2-Fluoro-6-methyl-phenyl)-piperidin-4-yl]-1-[2-(oxetan-3-yloxy)-benzyl]-3,4-dihydro-1H-quinazolin-2-one;

1-(2-Cyclobutoxy-benzyl)-3-[1-(2-fluoro-6-methyl-phenyl)-piperidin-4-yl]-3,4-dihydro-1H-quinazolin-2-one;

3-[1-(2-Fluoro-6-methyl-phenyl)-piperidin-4-yl]-1-[2-(tetrahydro-pyran-4-yloxy)-benzyl]-3,4-dihydro-1H-quinazolin-2-one;

1-(2-Cyclopropylmethoxy-benzyl)-3-[1-(2-fluoro-6-methyl-phenyl)-piperidin-4-yl]-3,4-dihydro-1H-quinazolin-2-one;

(2-{3-[1-(2-Fluoro-6-methyl-phenyl)-piperidin-4-yl]-2-oxo-3,4-dihydro-2H-quinazolin-1-ylmethyl}-phenoxy)-acetonitrile;

1-(2-Cyclopropyl-benzyl)-3-[1-(2-fluoro-6-methyl-phenyl)-piperidin-4-yl]-3,4-dihydro-1H-quinazolin-2-one;

3-[1-(2-Fluoro-6-methyl-phenyl)-piperidin-4-yl]-1-(2-isopropyl-benzyl)-3,4-dihydro-1H-quinazolin-2-one;

3-[1-(2-Fluoro-6-methyl-phenyl)-piperidin-4-yl]-1-(2-trifluoromethyl-benzyl)-3,4-dihydro-1H-pteridin-2-one;

3-[1-(2-Fluoro-6-methyl-phenyl)-piperidin-4-yl]-1-(3-isopropoxy-pyrazin-2-ylmethyl)-3,4-dihydro-1H-quinazolin-2-one;

3-[1-(2-Fluoro-6-methyl-phenyl)-piperidin-4-yl]-1-(3-isopropoxy-pyridin-2-ylmethyl)-3,4-dihydro-1H-quinazolin-2-one;

3-[1-(2-Fluoro-6-methyl-phenyl)-piperidin-4-yl]-1-(4-isopropyl-pyridin-3-ylmethyl)-3,4-dihydro-1H-quinazolin-2-one;

3-[1-(2-Fluoro-6-methyl-phenyl)-piperidin-4-yl]-1-(3-isopropyl-pyrazin-2-ylmethyl)-3,4-dihydro-1H-quinazolin-2-one;

3-[1-(2-Fluoro-6-methyl-phenyl)-piperidin-4-yl]-1-(4-isopropyl-pyrimidin-5-ylmethyl)-3,4-dihydro-1H-quinazolin-2-one;

3-[1-(2-Fluoro-6-methyl-phenyl)-piperidin-4-yl]-1-(2-trifluoromethyl-benzyl)-3,4-dihydro-1H-pyrimido[4,5-d]pyrimidin-2-one;

3-[1-(2-Fluoro-6-methyl-phenyl)-piperidin-4-yl]-1-(2-trifluoromethyl-pyridin-3-ylmethyl)-3,4-dihydro-1H-quinazolin-2-one;

7-[1-(2-Fluoro-6-methyl-phenyl)-piperidin-4-yl]-5-(2-trifluoromethyl-benzyl)-7,8-dihydro-5H-pyrimido[5,4-c]pyridazin-6-one;

3-[1-(2-Fluoro-6-methyl-phenyl)-piperidin-4-yl]-1-(4-trifluoromethyl-pyridin-3-ylmethyl)-3,4-dihydro-1H-quinazolin-2-one;

1-(2-Cyclopropoxy-benzyl)-3-[1-(2-fluoro-6-methyl-phenyl)-piperidin-4-yl]-3,4-dihydro-1H-quinazolin-2-one;

3-[1-(2-Fluoro-6-methyl-phenyl)-piperidin-4-yl]-1-(3-trifluoromethyl-pyridin-2-ylmethyl)-3,4-dihydro-1H-quinazolin-2-one;

3-[1-(2-Fluoro-6-methyl-phenyl)-piperidin-4-yl]-4-methyl-1-(2-trifluoromethyl-benzyl)-3,4-dihydro-1H-quinazolin-2-one;

1,3-Dimethyl-5-{4-[2-oxo-1-(2-trifluoromethyl-benzyl)-1,4-dihydro-2H-quinazolin-3-yl]-piperidin-1-yl}-1H-pyrazole-4-carbonitrile;

3-[1-(4-Chloro-2,5-dimethyl-2H-pyrazol-3-yl)-piperidin-4-yl]-1-(2-trifluoromethyl-benzyl)-3,4-dihydro-1H-quinazolin-2-one;

3-[1-(2-Fluoro-6-methyl-phenyl)-piperidin-4-yl]-1-(2-trifluoromethoxy-benzyl)-3,4-dihydro-1H-quinazolin-2-one;

1-(2-Chloro-benzyl)-3-[1-(2-fluoro-6-methyl-phenyl)-piperidin-4-yl]-3,4-dihydro-1H-quinazolin-2-one;

3-[1-(2-Fluoro-6-trifluoromethyl-phenyl)-piperidin-4-yl]-1-(2-trifluoromethyl-benzyl)-3,4-dihydro-1H-quinazolin-2-one;

3-[1-(2-Fluoro-6-methyl-phenyl)-azepan-4-yl]-1-(2-trifluoromethyl-benzyl)-3,4-dihydro-1H-quinazolin-2-one;

3-[1-(2-Fluoro-6-trifluoromethoxy-phenyl)-piperidin-4-yl]-1-(2-trifluoromethyl-benzyl)-3,4-dihydro-1H-quinazolin-2-one;

3-[1-(2-Chloro-6-methyl-phenyl)-piperidin-4-yl]-1-(2-trifluoromethyl-benzyl)-3,4-dihydro-1H-quinazolin-2-one;

3-[1-(2-Fluoro-6-methyl-phenyl)-piperidin-4-yl]-1-(4-isopropoxy-pyridazin-3-ylmethyl)-3,4-dihydro-1H-quinazolin-2-one;

3-[1-(2-Fluoro-6-methyl-phenyl)-azetidin-3-yl]-1-(2-trifluoromethyl-benzyl)-3,4-dihydro-1H-quinazolin-2-one;

1-(6-trifluoromethyl[2-$^2$H]benzyl)-3-[1-(2-fluoro-6-methyl-phenyl)-piperidin-4-yl]-3,4-dihydro-1H-quinazolin-2-one; or 3-[1-(2-Fluoro-6-methyl-phenyl)-piperidin-4-yl]-1-(2-methyl-4-trifluoromethyl-thiazol-5-ylmethyl)-3,4-dihydro-1H-quinazolin-2-one.

The compounds of formula (I) according to embodiments 1) to 17) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or (II), or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) as defined in any one of embodiments 1) to 17).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

For avoidance of any doubt, if compounds are described as useful for the prevention or treatment of certain diseases, such compounds are likewise suitable for use in the preparation of a medicament for the prevention or treatment of said diseases.

The compounds of formula (I) as defined in any one of embodiments 1) to 17) are useful for the prevention/prophylaxis or treatment of diseases and disorders related to pathogenic events associated with elevated levels of C5a and/or with C5aR activation.

Such diseases and disorders related to pathogenic events associated with elevated levels of C5a and/or with C5aR activation are especially:
vasculitic diseases or disorders,
inflammatory diseases or disorders involving intravascular microvesicle release,
immune complex (IC) diseases or disorders,
neurodegenerative diseases or disorders,
complement related inflammatory diseases or disorders,
bullous diseases or disorders,
diseases or disorders related to ischemia and/or ischemic reperfusion injury,
inflammatory bowel diseases or disorders,
autoimmune diseases or disorders, or, in addition to the above listed,
cancer.

In addition to the above-listed diseases and disorders, further diseases and disorders related to pathogenic events associated with elevated levels of C5a and/or with C5aR activation are:
further inflammatory diseases or disorders associated with elevated levels of C5a and/or with C5aR activation such as especially neutropenia, sepsis, septic shock, stroke, inflammation associated with severe burns, osteoarthritis, acute (adult) respiratory distress syndrome (ARDS), chronic pulmonary obstructive disorder (COPD), asthma (especially bronchial asthma), systemic inflammatory response syndrome (SIRS), tissue graft rejection, hyperacute rejection of transplanted organs, multiple organ dysfunction syndrome (MODS), diabetic retinopathy, neuromyelitis optica, and glomerulonephritis including Heyman nephritis/membranous glomerulonephritis, Berger's disease (IgA nephropathy), and other forms of glomerulonephritis including C3 glomerulopathy;
as well as
hemotological diseases which are associated with activation of coagulation and fibrinolytic systems, disseminated intravascular coagulation (DIC), pernicious anemia, warm and cold autoimmune hemolytic anemia (AIHA), anti-phospholipid syndrome and its associated complications, arterial or venous thrombosis, pregnancy complications such as recurrent miscarriage and fetal death, preeclampsia, placental insufficiency, fetal growth restriction, cervical remodeling and preterm birth, idiopathic thrombocytopenic purpura (ITP), atypical hemolytic uremic syndrome (aHUS), paroxysmal nocturnal hemoglobinuria (PNH), allergic transfusion reactions, acute antibody-mediated kidney allograft rejection, cold agglutinin disease and glaucoma.

The present compounds may in addition be useful for
the prevention or treatment of deleterious consequences of contact sensitivity and inflammation caused by contact with artificial surfaces;
the prevention or treatment of increased leukocyte and platelet activation (and infiltration to tissues thereof);
the prevention or treatment of pathologic sequelae (such as especially prevention or treatment of the development of tissue injury, especially of pulmonary tissue injury) associated to an intoxication or an injury such as a trauma, an hemorrhage, a shock, or surgery including transplantation, including multiple organ failure (MOF), septic shock, shock due to intoxication (such as shock due to snake venom), or acute lung inflammatory injury;
the prevention or treatment of pathologic sequelae associated with insulin-dependent diabetes mellitus;
the prevention of/the reduction of the risk of myocardial infarction or thrombosis; prevention or treatment of edema or increased capillary permeability;
the prevention of/the reduction of coronary endothelial dysfunction induced by cardiopulmonary bypass and/or cardioplegia.

Vasculitic diseases or disorders include especially vasculitis, ANCA associated vasculitis and glomerulonephritis (GN, especially rapidly progressive GN) associated with ANCA associated vasculitis, leukoclastic vasculitis, granulomatosis with polyangiitis (GPA, also referred to as Wegener's granulomatosis), microscopic polyangiitis, Churg-Strauss syndrome, Henoch-Schönlein purpura, polyateritis nodosa, cryoglobulinaemia, giant cell arteritis (GCA), Behcet's disease, and Takayasu's arteritis (TAK).

Inflammatory diseases or disorders involving intravascular microvesicle release include especially thrombotic microangiopathy, and sickle cell disease.

Immune complex (IC) diseases or disorders include especially cryoglobulinemia, Sjögren's syndrome (and associated immunological profiles), Goodpasture syndrome (anti-glomerular basement antibody disease) and glomerulonephritis (GN, especially rapidly progressive GN) or pulmonary hemorrhage associated with Goodpasture syndrome, and hypersensitivity;

Neurodegenerative diseases and disorders include especially amyotrophic lateral sclerosis (ALS), Alzheimer's disease, Parkinson's disease, Huntington's disease, Guillain- Barre syndrome, neuropathy, and cognitive function decline associated with cardiopulmonary bypass surgery and related procedures.

Complement related inflammatory diseases or disorders include especially coronary thrombosis, vascular occlusion, post-surgical vascular reocclusion, atherosclerosis, traumatic central nervous system injury, arrhythmogenic cardiomyopathy, bronchoconstriction, acute respiratory distress syndrome (ARDS), Chronic Obstructive Pulmonary Disorder (COPD), complement mediated thrombotic microangiopathies including atypical haemolytic uremic syndrome, and Gaucher disease.

Bullous diseases or disorders include especially bullous pemphigoid, bullous acquisita, pemphigus foliaceus, pemphigus vulgaris, and sub-epidermal blisters.

Diseases or disorders related to ischemia and/or ischemic reperfusion injury include especially ischemic reperfusion injury (including myocardial ischemia-reperfusion injury, and ischemic/reperfusion injury resulting from transplantation, including solid organ transplant), ischemic colitis, and cardiac ischemia.

Inflammatory bowel diseases or disorders include especially irritable bowel syndrome, ulcerative colitis, Crohn's disease, and inflammatory bowel disease (IBD).

Autoimmune diseases or disorders include especially rheumatoid arthritis, osteoarthritis, systemic lupus erythematosus (SLE) and glomerulonephritis (GN, especially rapidly progressive GN) associated with lupus erythematosus (lupus nephritis), central nervous system (CNS) lupus, dermatomyositis, pemphigus, systemic sclerosis (scleroderma), autoimmune hemolytic and thrombocytopenic states, immunovasculitis, mixed cryoglobulinemia, atopic dermatitis, chronic urticaria, psoriasis, myasthenia gravis, and anti-phospholipid syndrome.

Further inflammatory diseases or disorders associated with elevated levels of C5a and/or with C5aR activation include especially neutropenia, sepsis, septic shock, stroke, inflammation associated with severe burns, osteoarthritis, acute (adult) respiratory distress syndrome (ARDS), chronic pulmonary obstructive disorder (COPD), asthma, especially bronchial asthma, systemic inflammatory response syndrome (SIRS), tissue graft rejection, hyperacute rejection of transplanted organs, multiple organ dysfunction syndrome (MODS), diabetic retinopathy, neuromyelitis optica, and glomerulonephritis including Heyman nephritis/membranous glomerulonephritis, Berger's disease (IgA nephropathy), and other forms of glomerulonephritis including C3 glomerulopathy.

The term "cancer" notably refers to skin cancer including melanoma including metastatic melanoma; lung cancer including non-small cell lung cancer; bladder cancer including urinary bladder cancer, urothelial cell carcinoma; renal carcinomas including renal cell carcinoma, metastatic renal cell carcinoma, metastatic renal clear cell carcinoma; gastrointestinal cancers including colorectal cancer, metastatic colorectal cancer, familial adenomatous polyposis (FAP), oesophageal cancer, gastric cancer, gallbladder cancer, cholangiocarcinoma, hepatocellular carcinoma, and pancreatic cancer such as pancreatic adenocarcinoma or pancreatic ductal carcinoma; endometrial cancer; ovarian cancer; cervical cancer; neuroblastoma; prostate cancer including castrate-resistant prostate cancer; brain tumors including brain metastases, malignant gliomas, glioblastoma multiforme, medulloblastoma, meningiomas; breast cancer including triple negative breast carcinoma; oral tumors; nasopharyngeal tumors; thoracic cancer; head and neck cancer; leukemias including acute myeloid leukemia, adult T-cell leukemia; carcinomas; adenocarcinomas; thyroid carcinoma including papillary thyroid carcinoma; choriocarcinoma; Ewing's sarcoma; osteosarcoma; rhabdomyosarcoma; Kaposi's sarcoma; lymphoma including Burkitt's lymphoma, Hodgkin's lymphoma, MALT lymphoma; multiple myelomas; or virally induced tumors.

When used for the prevention/prophylaxis or treatment of a cancer, such use includes use of the present compounds as single therapeutic agents and their use in combination with one or more chemotherapy agents and/or radiotherapy and/or targeted therapy (especially in combination with targeted therapy).

The terms "radiotherapy" or "radiation therapy" or "radiation oncology", refer to the medical use of ionizing radiation in the prevention/prophylaxis (adjuvant therapy) and/or treatment of cancer; including external and internal radiotherapy.

The term "targeted therapy" refers to the prevention/prophylaxis (adjuvant therapy) and/or treatment of cancer with one or more anti-neoplastic agents such as small molecules or antibodies which act on specific types of cancer cells or stromal cells. Some targeted therapies block the action of certain enzymes, proteins, or other molecules involved in the growth and spread of cancer cells. Other types of targeted therapies help the immune system kill cancer cells (immunotherapies); or inhibit angiogenesis, the growth and formation of new blood vessels in the tumor; or deliver toxic substances directly to cancer cells and kill them. An example of a targeted therapy which is in particular suitable to be combined with the compounds of the present invention is immunotherapy, especially immunotherapy targeting the progammed cell death receptor 1 (PD-1 receptor) or its ligand PD-L1.

When used in combination with the present compounds, the term "targeted therapy" especially refers to agents such as:
  a) Epidermal growth factor receptor (EGFR) inhibitors or blocking antibodies (for example Gefitinib, Erlotinib, Afatinib, Icotinib, Lapatinib, Panitumumab, Zalutumumab, Nimotuzumab, Matuzumab and Cetuximab);
  b) RAS/RAF/MEK pathway inhibitors (for example Vemurafenib, Sorafenib, Dabrafenib, GDC-0879, PLX-4720, LGX818, RG7304, Trametinib (GSK1120212), Cobimetinib (GDC-0973/XL518), Binimetinib (MEK162, ARRY-162), Selumetinib (AZD6244));
  c) Aromatase inhibitors (for example Exemestane, Letrozole, Anastrozole, Vorozole, Formestane, Fadrozole);
  d) Angiogenesis inhibitors, especially VEGF signalling inhibitors such as Bevacuzimab (Avastin), Ramucirumab, Sorafenib or Axitinib;
  e) Immune Checkpoint inhibitors (for example: anti-PD1 antibodies such as Pembrolizumab (Lambrolizumab, MK-3475), Nivolumab, Pidilizumab (CT-011), AMP-514/MED 10680, PDR001, SHR-1210; REGN2810, BGBA317; fusion proteins targeting PD-1 such as AMP-224; small molecule anti-PD1 agents such as for example compounds disclosed in WO2015/033299, WO2015/044900 and WO2015/034820; anti-PD1L antibodies, such as BMS-936559, atezolizumab (MPDL3280A, RG7446), MED14736, avelumab (MSB0010718C), durvalumab (MED14736); anti-PDL2 antibodies, such as AMP224; anti-CTLA-4 antibodies, such as ipilimumab, tremilmumab; anti-Lymphocyte-activation gene 3 (LAG-3) antibodies, such as BMS-986016, IMP701, MK-4280, ImmuFact IMP321; anti T cell immunoglobulin mucin-3 (TIM-3) antibodies, such as MBG453; anti-CD137/4-1BB antibodies, such as BMS-663513/urelumab, PF-05082566; anti T cell immunoreceptor with Ig and ITIM domains (TIGIT) antibodies, such as RG6058 (anti-TIGIT, MTIG7192A);

f) Vaccination approaches (for example dendritic cell vaccination, peptide or protein vaccination (for example with gp100 peptide or MAGE-A3 peptide);

g) Re-introduction of patient derived or allogenic (non-self) cancer cells genetically modified to secrete immunomodulatory factors such as granulocyte monocyte colony stimulating factor (GMCSF) gene-transfected tumor cell vaccine (GVAX) or Fms-related tyrosine kinase 3 (Flt-3) ligand gene-transfected tumor cell vaccine (FVAX), or Toll like receptor enhanced GM-CSF tumor based vaccine (TEGVAX); h) T-cell based adoptive immunotherapies, including chimeric antigen receptor (CAR) engineered T-cells (for example CTL019);

i) Cytokine or immunocytokine based therapy (for example Interferon alpha, interferon beta, interferon gamma, interleukin 2, interleukin 15);

j) Toll-like receptor (TLR) agonists (for example resiquimod, imiquimod, glucopyranosyl lipid A, CpG oligodesoxynucleotides);

k) Thalidomide analogues (for example Lenalidomide, Pomalidomide);

l) Indoleamin-2,3-Dioxgenase (IDO) and/or Tryptophane-2,3-Dioxygenase (TDO) inhibitors (for example RG6078/NLG919/GDC-0919; Indoximod/1MT (1-methyltryptophan), INCB024360/Epacadostat, PF-06840003 (EOS200271), F001287);

m) Activators of T-cell co-stimulatory receptors (for example anti-OX40/CD134 (Tumor necrosis factor receptor superfamily, member 4, such as RG7888 (MOXR0916), 9B12; MEDI6469, GSK3174998, MEDI0562), anti OX40-Ligand/CD252; anti-glucocorticoid-induced TNFR family related gene (GITR) (such as TRX518, MEDI1873, MK-4166, BMS-986156), anti-CD40 (TNF receptor superfamily member 5) antibodies (such as Dacetuzumab (SGN-40), HCD122, CP-870,893, RG7876, ADC-1013, APX005M, SEA-CD40); anti-CD40-Ligand antibodies (such as BG9588); anti-CD27 antibodies such as Varlilumab);

n) Molecules binding a tumor specific antigen as well as a T-cell surface marker such as bispecific antibodies (for example RG7802 targeting CEA and CD3) or antibody fragments, antibody mimetic proteins such as designed ankyrin repeat proteins (DARPINS), bispecific T-cell engager (BITE, for example AMG103, AMG330);

o) Antibodies or small molecular weight inhibitors targeting colony-stimulating factor-1 receptor (CSF-1R) (for example Emactuzumab (RG7155), Cabiralizumab (FPA-008), PLX3397);

p) Agents targeting immune cell check points on natural killer cells such as antibodies against Killer-cell immunoglobulin-like receptors (KIR) for example Lirilumab (IPH2102/BMS-986015);

q) Agents targeting the Adenosine receptors or the ectonucleases CD39 and CD73 that convert ATP to Adenosine, such as MEDI9447 (anti-CD73 antibody), PBF-509; CPI-444 (Adenosine A2a receptor antagonist).

When used in combination with the present compounds, immune checkpoint inhibitors, and especially those targeting the PD-1 receptor or its ligand PD-L1, are preferred.

The invention further relates to a method of modulating (especially downregulating) the consequences of the complement activation (especially by activating innate cells) in a subject in need thereof [especially in a subject having a disease or disorder related to pathogenic events associated with elevated levels of C5a and/or with C5aR activation; in particular in a subject having a vasculitic disease or disorder, an inflammatory disease or disorder involving intravascular microvesicle release, an immune complex (IC) disease or disorder, a neurodegenerative disease or disorder, a complement related inflammatory disease or disorder, a bullous disease or disorder, a disease or disorder related to ischemia and/or ischemic reperfusion injury, an inflammatory bowel disease or disorder, or an autoimmune disease or disorder; or in a subject having a contact sensitivity or an inflammation caused by contact with artificial surfaces; an increased leukocyte and platelet activation (and infiltration to tissues thereof); a pathologic sequelae associated to an intoxication or an injury such as a trauma, an hemorrhage, a shock, or surgery including transplantation, including multiple organ failure (MOF), septic shock, shock due to intoxication (such as shock due to snake venom), or acute lung inflammatory injury; a pathologic sequelae associated with insulin-dependent diabetes mellitus; a myocardial infarction or thrombosis; an edema or an increased capillary permeability; or a reduction of coronary endothelial dysfunction induced by cardiopulmonary bypass and/or cardioplegia], comprising administering to said subject a pharmaceutically active amount of a compound of formula (I) as defined in any one of embodiments 1) to 17). For avoidance of doubt, the term "modulating the complement activation" is to be understood as downregulating/reducing the amplification of the immune response and downregulating/reducing the activation of the cell-killing membrane attack complex, especially by activating innate cells.

Preparation of Compounds of Formula (I):

The compounds of formula (I) can be prepared by the methods given below, by the methods given in the experimental part below or by analogous methods. Optimum reaction conditions may vary with the particular reactants or solvents used, but such conditions can be determined by a person skilled in the art by routine optimisation procedures. In the schemes below, the generic groups Ring A, W, X, Y, Z, $R^1$, $R^2$, $R^3$ and $R^4$ are as defined for the compounds of formula (I). In some instances the generic groups Ring A, W, X, Y, Z, $R^1$, $R^2$, $R^3$ and $R^4$ may be incompatible with the assembly illustrated in the schemes, or will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases the final product may be further modified, for example, by manipulation of substituents to give a new final product. These manipulations may include, but are not limited to, reduction, oxidation, alkylation, acylation, and hydrolysis reactions which are commonly known to those skilled in the art. The compounds obtained may also be converted into salts, especially pharmaceutically acceptable salts in a manner known per se.

Compounds of formula (I) of the present invention can be prepared according to the general sequence of reactions outlined below. Compounds of structure Ia, Ib and Ic can be prepared according to the synthetic route given in scheme A below.

Compounds of structure A-1 can be prepared by reductive amination of a suitable aldehyde of structure BB-1 with amines of structure BB-2 using standard conditions such as treatment with NaBH(OAc)$_3$ in the presence of AcOH and a suitable solvent such as DCM, MeOH, THF or a mixture thereof at temperatures around RT. Alternatively, a two-step procedure can be applied (i) condensation of a suitable aldehyde of structure BB-1 with amines of structure BB-2 in the presence of a suitable solvent such as MeOH at temperatures around 60° C. and (ii) consecutive reduction of the intermediate imine by treatment with NaBH$_4$ at temperatures between 0° C. and RT (Scheme A, step a).

Diamino compounds of structure A-2 can be prepared by reduction of the nitro group in compounds of structure A-1 using standard conditions such as catalytic hydrogenation with a suitable catalyst such as Pd/C and in the presence of a suitable solvent such as EtOAc (Scheme A, step b).

Cyclic ureas of structure A-3 can be prepared by cyclisation of diamines of structure A-2 by treatment with a suitable carbonyl transfer agent such as CDI in the presence of a suitable aprotic solvent such as MeCN at temperatures between RT and 45° C. (Scheme A, step c).

Alkylation of the nitrogen atom having a free valency in compounds of structure A-3 with a suitable halide of structure BB-3 wherein X represents chlorine or bromine, R$^2$ represents a mono- or di-substituted phenyl or 5- or 6-membered heteroaryl and R$^3$ represents hydrogen, (C$_{1-3}$)alkyl or (C$_{1-3}$)alkoxy-carbonyl, in the presence of a suitable base such as NaH or K$_2$CO$_3$ and in solvents such as THF, DMF or a mixture of both at temperatures between 0° C. and 50° C. may afford compounds of structure A-4 (Scheme A, step d).

Cleavage of the Boc protecting group in compounds of structure A-4 can be performed using a suitable acid such as HCl or TFA in the presence of a suitable solvent such as dioxane, MeOH or DCM at temperatures around RT (Scheme A, step e).

Compounds of structure Ia wherein R$^1$ represents a mono-, di- or tri-substituted phenyl or 5- or 6-membered heteroaryl can be prepared by Buchwald-Hartwig cross coupling of halides of structure R$^1$—X (BB-4) wherein X represents iodine, bromine or chloride and R$^1$ represents a mono-, di- or tri-substituted phenyl or 5- or 6-membered heteroaryl with an amine of structure A-5 in the presence of a suitable palladium catalyst such as Pd$_2$(dba)$_3$ and a ligand such as BINAP, in the presence of a suitable base such as sodium tert-butoxide and heating in a suitable solvent such as toluene at temperatures between 70° C. and 110° C. (Scheme A, step f).

Compounds of structure Ib wherein R$^1$ represents a mono-, di- or tri-substituted 5-membered heteroaryl can be prepared following a four-step procedure: (i) aromatic nucleophilic substitution of amines of structure A-5 on activated halides of structure R$^1$—X (BB-4) wherein X represents fluorine or chlorine and R$^1$ represents a suitable mono-, di- or tri-substituted 5-membered heteroaryl which is substituted for instance by one formyl group in ortho position of the halogen atom X in the presence of a suitable base such as CsF or K$_2$CO$_3$ and heating in a suitable solvent such as DMSO under microwave irradiation at temperatures between 60° C. and 150° C. and (ii) consecutive decarbonylation by treatment with a suitable acid such as toluene-4-sulfonic acid and in the presence of a suitable solvent such as MeOH under possible microwave irradiation at temperatures around 120° C. and (iii) consecutive chlorination by treatment with a chlorinating reagent such as NCS in the presence of a suitable solvent such as THF at temperatures around RT and (iv) possible consecutive Suzuki cross coupling with a (C$_1$-C$_4$)-alkyl boronic acid or boroxine in the presence of a suitable palladium catalyst such as PEPPSI-IPr, in the presence of a suitable base such as K$_2$CO$_3$ and heating in a suitable solvent such as dioxane at temperatures around 115° C. Alternatively, compounds of structure Ib wherein R$^1$ represents a mono-, di- or tri-substituted phenyl or 5- or 6-membered heteroaryl can be prepared by aromatic nucleophilic substitution of amines of structure A-5 on activated halides of structure R$^1$—X (BB-4) wherein X represents fluorine or chlorine and R$^1$ represents a suitable mono-, di- or tri-substituted phenyl or 5- or 6-membered heteroaryl which is substituted for instance by one cyano group in ortho position of the halogen atom X in the presence of a suitable base such as CsF or K$_2$CO$_3$ and heating in a suitable solvent such as DMSO under possible microwave irradiation at temperatures between 60° C. and 150° C. (Scheme A, step f).

Compounds of structure A-6 can be prepared by cleavage of the Boc protecting group in compounds of structure A-3 using a suitable acid such as HCl or TFA in the presence of a suitable solvent such as dioxane, MeOH or DCM at temperatures around RT (Scheme A, step g).

Compounds of structure A-7 wherein R$^1$ represents a mono-, di- or tri-substituted phenyl or 5- or 6-membered heteroaryl can be prepared by aromatic nucleophilic substitution of amines of structure A-6 on activated halides of structure R$^1$—X (BB-4) wherein X represents fluorine or chlorine and R$^1$ represents a suitable mono-, di- or tri-substituted phenyl or 5- or 6-membered heteroaryl in the presence of a suitable base such as K$_2$CO$_3$ and heating in a suitable solvent such as DMSO at temperatures between 60° C. and 110° C. (Scheme A, step h).

Alternatively, compounds of structure A-7 wherein R$^1$ represents a mono-, di- or tri-substituted phenyl which is substituted by at least one methyl group at the ortho position of the connecting nitrogen can be prepared following a four-step procedure: (i) aromatic nucleophilic substitution of amines of structure A-6 on halides of structure R$^1$—X (BB-4) wherein X represents fluorine or chlorine and R$^1$ represents a suitable mono-, di- or tri-substituted phenyl which is substituted by at least one formyl group at the ortho position of the halogen atom X in the presence of a suitable base such as K$_2$CO$_3$ and heating in a suitable solvent such as DMSO at temperatures between 60° C. and 110° C. and (ii) consecutive reduction of the benzaldehyde derivative by treatment with a suitable reducing reagent such as NaBH$_4$ in the presence of a suitable solvent such as MeOH at temperatures between 0° C. and RT and (iii) consecutive acetylation of the resulting benzyl alcohol by treatment with acetyl chloride in the presence of a suitable base such as TEA and in a suitable solvent such as DCM at temperatures between 0° C. and RT and (iv) final catalytic hydrogenation of the resulting benzyl ester with a suitable catalyst such as Pd/C in the presence of a suitable solvent such as EtOAc, MeOH or a mixture thereof at temperatures around RT (Scheme A, step h).

Compounds of structure Ia wherein R$^1$ represents a mono-, di- or tri-substituted phenyl or 5- or 6-membered heteroaryl can be prepared by alkylation of the nitrogen atom having a free valency in compounds of structure A-7 with a suitable halide of structure BB-3 wherein X represents chlorine or bromine, R$^2$ represents a mono- or di-substituted phenyl or 5- or 6-membered heteroaryl and R$^3$ represents hydrogen, (C$_{1-3}$)alkyl or (C$_{1-3}$)alkoxy-carbonyl, in the presence of a suitable base such as NaH or K$_2$CO$_3$ and in solvents such as THF, DMF or a mixture of both at temperatures between 0° C. and 50° C. Alternatively, alkylation of the nitrogen atom having a free valency in compounds of structure A-7 can be achieved using Mitsunobu conditions by treatment with a suitable alcohol of structure BB-3 wherein X represents hydroxy and for instance a (cyanomethylene)trialkylphosphorane reagent in the presence of a suitable solvent such as toluene at temperatures around 110° C. (Scheme A, step i).

Alkylation of the free hydroxyl group in compounds of structure Ia wherein $R^2$ represents a mono-, di- or tri-substituted phenyl or 5- or 6-membered heteroaryl which is substituted by one hydroxyl group with a suitable $(C_1-C_4)$-alkyl halide, $(C_{1-3})$alkyl-carbonyloxy-$(C_{2-3})$alkyl halide, cyano-$(C_1-C_2)$alkyl halide, $(C_{3-6})$cycloalkyl halide or $(C_{3-6})$cycloalkyl-$(C_{1-3})$alkyl halide wherein the $(C_{3-6})$cycloalkyl independently contains one optional ring oxygen, or $R^{21a}R^{21b}N$—$(C_2-C_3)$alkyl halide wherein $R^{21a}$ and $R^{21b}$ independently represent hydrogen or $(C_{1-4})$alkyl, in the presence of a suitable base such as NaH or $K_2CO_3$ and in solvents such as THF, DMF or a mixture thereof at temperatures between 0° C. and 100° C. may afford compounds of structure Ic wherein $R^2$ represents a mono-, di- or tri-substituted phenyl or 5- or 6-membered heteroaryl which is substituted by one $(C_{1-4})$alkoxy, $(C_{1-3})$alkyl-carbonyloxy-$(C_{2-3})$alkoxy, cyano-$(C_1-C_2)$alkoxy, $(C_{3-6})$cycloalkoxy or $(C_{3-6})$cycloalkyl-$(C_{1-3})$alkylenoxy wherein the $(C_{3-6})$cycloalkyl independently contains one optional ring oxygen, or $R^{21a}R^{21b}N$—$(C_2-C_3)$alkylenoxy wherein $R^{21a}$ and $R^{21b}$ independently represent hydrogen or $(C_{1-4})$alkyl. Alternatively, Mitsunobu conditions can be used by treatment for instance with a (cyanomethylene)trialkylphosphorane reagent in the presence of a suitable solvent such as toluene at temperatures around 110° C. (Scheme A, step j).

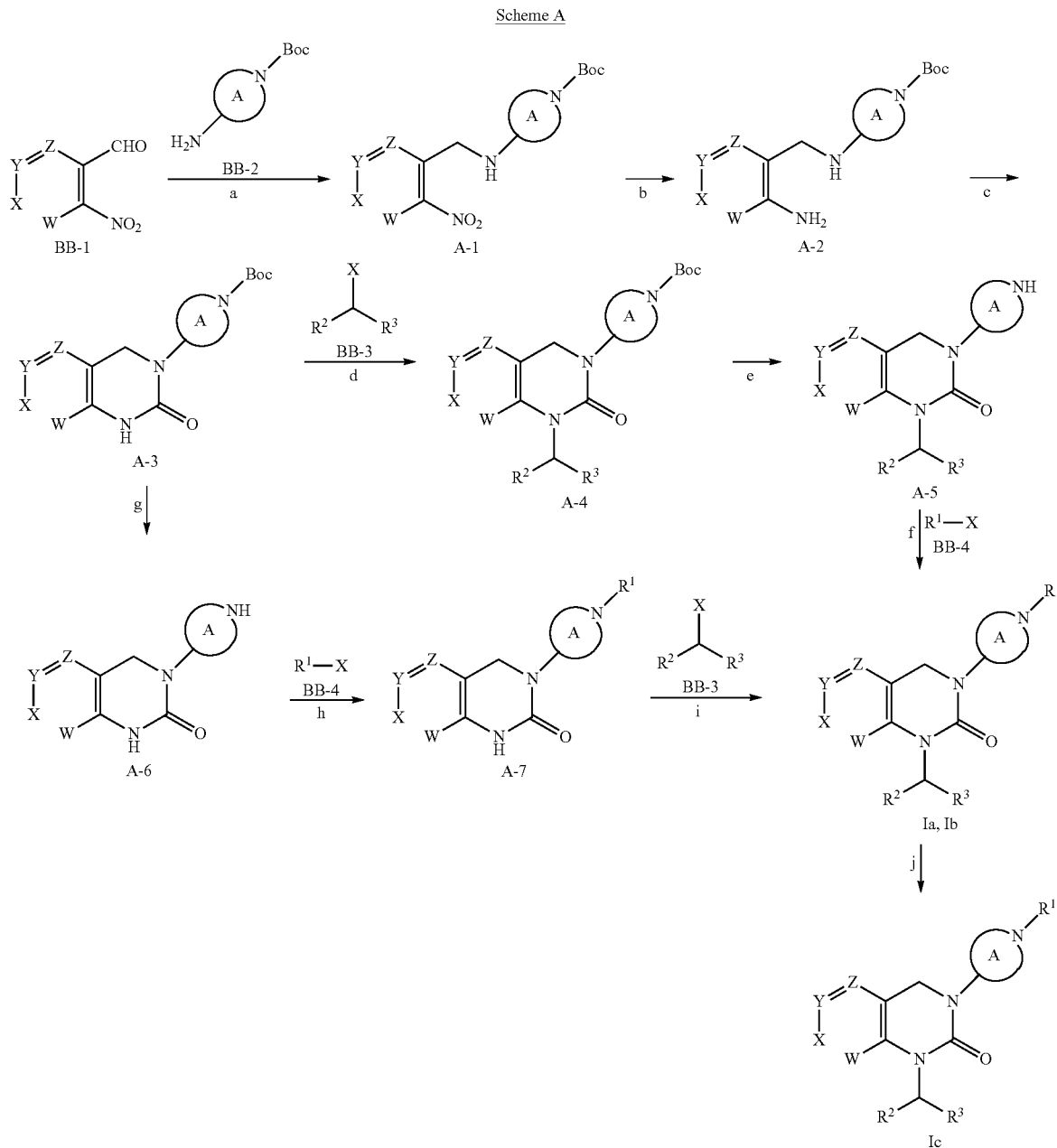

Scheme A

Catalytic deuteriation of compounds of structure Ia wherein $R^2$ represents a mono-, di- or tri-substituted phenyl or 5- or 6-membered heteroaryl which is substituted by one or more bromine with a suitable catalyst such as Pd/C in the presence of a suitable solvent such as EtOAc, MeOH or a mixture thereof at temperatures around RT may afford compounds of structure Ic wherein $R^2$ represents a mono-, di- or tri-substituted phenyl or 5- or 6-membered heteroaryl which is substituted by one or more deuterium (Scheme A, step j).

Compounds of structure Ic wherein $R^2$ represents a mono- or di-substituted phenyl or 5- or 6-membered heteroaryl which is substituted by one $(C_{1-3})$alkyl-carbonyloxy-$(C_{2-3})$alkoxy group can be additionally transformed to compounds of structure Ic wherein $R^2$ represents a mono-, di- or tri-substituted phenyl or 5- or 6-membered heteroaryl which is substituted by one hydroxy-$(C_{2-3})$alkoxy group by hydrolysis with a suitable base such as LiOH, NaOH or KOH in the presence of water and a suitable solvent such as THF, MeOH or EtOH or a mixture thereof at temperatures between RT and 50° C.

Compounds of structure Id can be prepared according to the synthetic route given in scheme B below.

Compounds of structure B-1 can be prepared by aromatic nucleophilic substitution of amines of structure BB-6 on chlorides of structure BB-5 by heating in a suitable solvent such as EtOH at temperatures around 70° C. (Scheme B, step a).

Reduction of the nitrile group in compounds of structure B-1 can be achieved for instance by treatment with a suitable reducing agent such as LiAlH$_4$ in the presence of a suitable solvent such as THF at temperatures around −60° C. (Scheme B, step b).

Compounds of structure B-3 can be prepared by reductive amination of ketones of structure BB-7 wherein $R^1$ represents a mono-, di- or tri-substituted phenyl or 5- or 6-membered heteroaryl with amines of structure B-2 using standard conditions such as treatment with NaBH(OAc)$_3$ in the presence of AcOH and a suitable solvent such as DCM or THF at temperatures around RT (Scheme B, step c).

Cyclisation of diamines of structure B-3 by treatment with a suitable carbonyl transfer agent such as CDI in the presence of a suitable aprotic solvent such as MeCN at temperatures between RT and 80° C. may afford compounds of structure Id (Scheme B, step d).

Scheme B

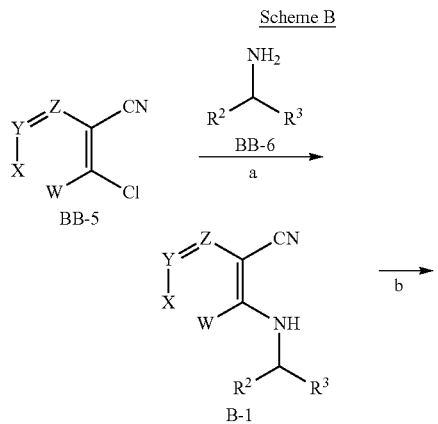

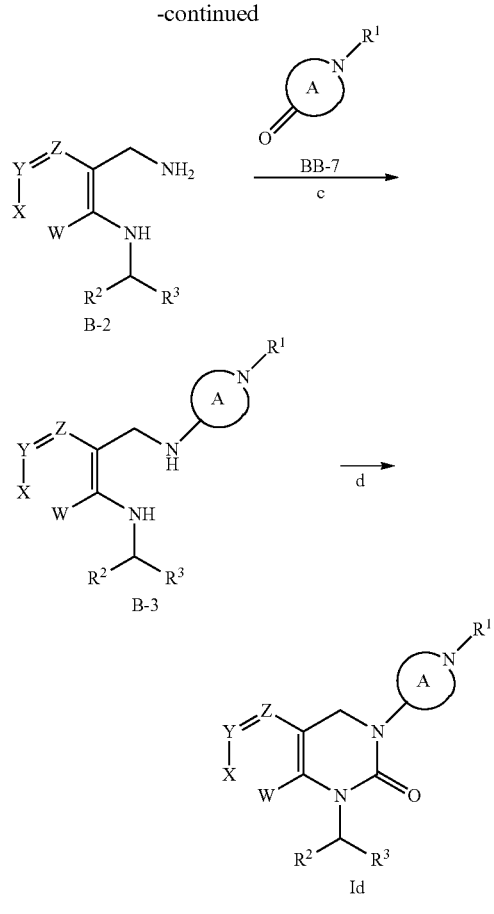

Compounds of structure Ie can be prepared according to the synthetic route given in scheme C below.

Compounds of structure C-1 can be prepared by esterification of carboxylic acids of structure BB-8 by treatment with a strong acid such as H$_2$SO$_4$ and heating in a suitable alcohol such as EtOH at temperatures around 80° C. (Scheme C, step a).

Reduction of carboxylic esters of structure C-1 can be achieved for instance by treatment with a suitable reducing reagent such as CaBH$_4$ (formed in situ from NaBH$_4$ and CaCl$_2$) in the presence of a suitable solvent such as EtOH at temperatures between −10° C. and RT to give alcohol of structure C-2 (Scheme C, step b).

Oxidation of primary alcohol of structure C-2 by treatment with a suitable oxidizing reagent such as MnO$_2$ in the presence of a suitable solvent such as DCM at temperatures between RT and 70° C. can afford aldehydes of structure C-3 (Scheme C, step c).

Compounds of structure C-4 can be prepared by reductive amination of aldehydes of structure C-3 with amines of structure BB-9 wherein $R^1$ represents a mono-, di- or tri-substituted phenyl or 5- or 6-membered heteroaryl using standard conditions such as treatment with NaBH(OAc)$_3$ in the presence of AcOH (or NaBH$_4$ respectively) and a suitable solvent such as DCM, MeOH, THF or a mixture thereof (or TFE respectively) at temperatures between RT and 40° C. (Scheme C, step d).

Cyclisation of diamines of structure C-4 by treatment with a suitable carbonyl transfer agent such as CDI in the presence of a suitable aprotic solvent such as MeCN or THF at temperatures between RT and 80° C. may afford compounds of structure C-5. The optional presence of a base such as NaH may allow the reaction to proceed (Scheme C, step e).

Compounds of structure Ie can be prepared by alkylation of the nitrogen atom having a free valency in compounds of structure C-5 with a suitable halide of structure BB-3 wherein X represents chlorine or bromine and $R^2$ represents a mono- or di-substituted phenyl or 5- or 6-membered heteroaryl and $R^3$ represents hydrogen, $(C_{1-3})$alkyl or $(C_{1-3})$alkoxy-carbonyl, in the presence of a suitable base such as NaH or $K_2CO_3$ and in solvents such as THF, DMF or a mixture of both at temperatures between 0° C. and 60° C. Alternatively, alkylation of the nitrogen atom having a free valency in compounds of structure C-5 can be achieved using Mitsunobu conditions by treatment with a suitable alcohol of structure BB-3 wherein X represents hydroxy and $R^2$ represents a mono- or di-substituted phenyl or 5- or 6-membered heteroaryl and $R^3$ represents hydrogen, $(C_{1-3})$alkyl or $(C_{1-3})$alkoxy-carbonyl and for instance a (cyanomethylene)trialkylphosphorane reagent in the presence of a suitable solvent such as toluene at temperatures around 110° C. (Scheme C, step f).

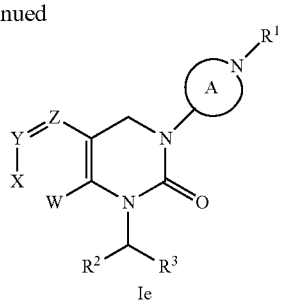

Compounds of structure If and Ig can be prepared according to the synthetic route given in scheme D below.

Compounds of structure D-1 wherein $R^4$ represents $(C_1-C_4)$alkyl can be prepared by reductive amination of ketones of structure BB-7 wherein $R^1$ represents a mono-, di- or tri-substituted phenyl or 5- or 6-membered heteroaryl with amines of structure BB-10 using standard conditions such as treatment with $NaBH(OAc)_3$ in the presence of AcOH and a suitable solvent such as DCM or THF at temperatures around RT (Scheme D, step a).

Cyclisation of diamines of structure D-1 by treatment with a suitable carbonyl transfer agent such as CDI in the presence of a suitable aprotic solvent such as MeCN at temperatures between RT and 80° C. may afford compounds of structure D-2 (Scheme D, step b).

Compounds of structure If can be prepared by alkylation of the nitrogen atom having a free valency in compounds of structure D-2 with suitable halides of structure BB-3 wherein X represents chlorine or bromine and $R^2$ represents a mono- or di-substituted phenyl or 5- or 6-membered heteroaryl and $R^3$ represents hydrogen, $(C_{1-3})$alkyl or $(C_{1-3})$alkoxy-carbonyl, in the presence of a suitable base such as NaH or $K_2CO_3$ and in solvents such as THF, DMF or a mixture thereof at temperatures between 0° C. and 60° C. Alternatively, alkylation of the nitrogen atom having a free valency in compounds of structure D-2 can be achieved using Mitsunobu conditions by treatment with a suitable alcohol of structure BB-3 wherein X represents hydroxy and for instance a (cyanomethylene)trialkylphosphorane reagent in the presence of a suitable solvent such as toluene at temperatures around 110° C. (Scheme D, step c). Chiral separation on racemates of formula If may afford pure enantiomers of structure Ig.

Scheme C

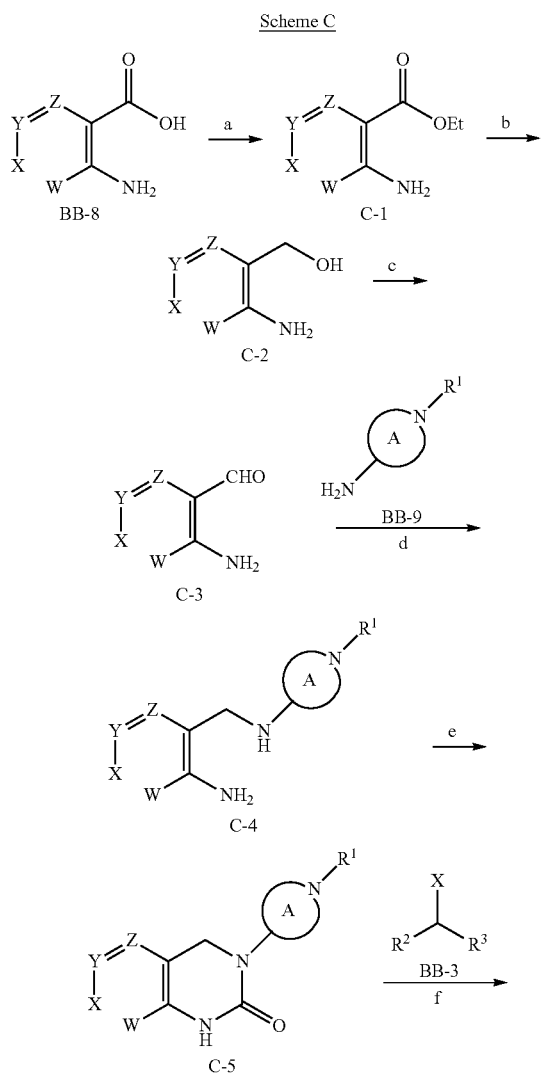

Scheme D

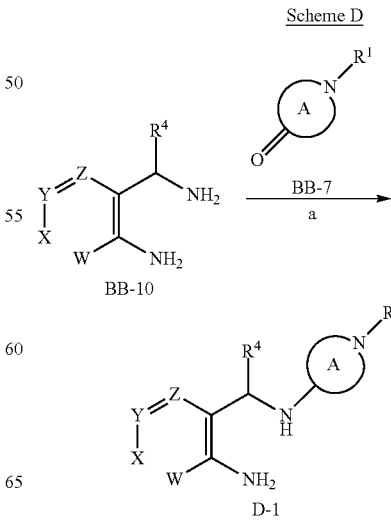

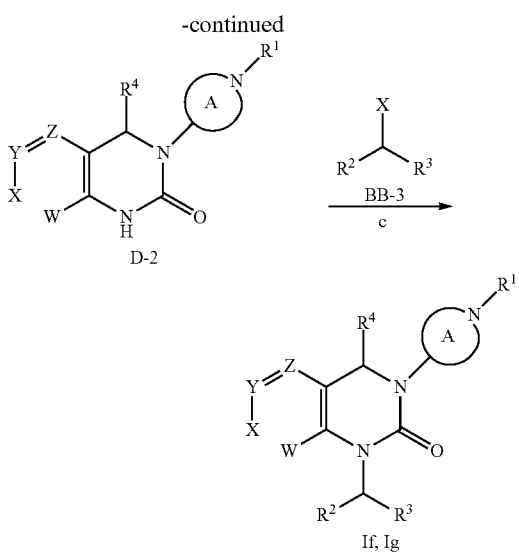

Compounds of structure Ih can be prepared according to the synthetic route given in scheme E below.

Compounds of structure E-1 can be prepared by mono-alkylation of the amino group in amines of structure BB-11 with a suitable halide of structure BB-3 wherein X represents chlorine or bromine and $R^2$ represents a mono- or di-substituted phenyl or 5- or 6-membered heteroaryl and $R^3$ represents hydrogen, $(C_{1-3})$alkyl or $(C_{1-3})$alkoxy-carbonyl, in the presence of a suitable base such as DIPEA and in solvents such as MeCN at temperatures around 70° C. (Scheme E, step a).

Cleavage of the Boc protecting group in compounds of structure E-1 can be performed using a suitable acid such as HCl or TFA in the presence of a suitable solvent such as dioxane, MeOH or DCM at temperatures between RT and 40° C. to afford diamines of structure E-2 (Scheme E, step b).

Cyclisation of diamines of structure E-2 by treatment with a suitable carbonyl transfer agent such as CDI in the presence of a suitable aprotic solvent such as MeCN at temperatures between RT and 40° C. may afford compounds of structure E-3 (Scheme E, step c).

Compounds of structure E-4 wherein P represents Boc can be prepared by alkylation of the nitrogen atom having a free valency in compounds of structure E-3 using Mitsunobu conditions by treatment with a suitable alcohol of structure BB-12 and for instance a (cyanomethylene)trialkylphosphorane reagent in the presence of a suitable solvent such as toluene at temperatures around 110° C. (Scheme E, step d).

Compounds of structure E-6 can be prepared by reductive amination of a suitable ketone of structure BB-14 with amines of structure BB-13 using standard conditions such as treatment with $NaBH(OAc)_3$ in the presence of AcOH and a suitable solvent such as DCM, MeOH, THF or a mixture thereof at temperatures around RT (Scheme E, step e).

Cleavage of the Boc protecting group in compounds of structure E-6 can be performed using a suitable acid such as HCl or TFA in the presence of a suitable solvent such as dioxane, MeOH or DCM at temperatures around RT to afford amines of structure E-7 (Scheme E, step f).

Scheme E

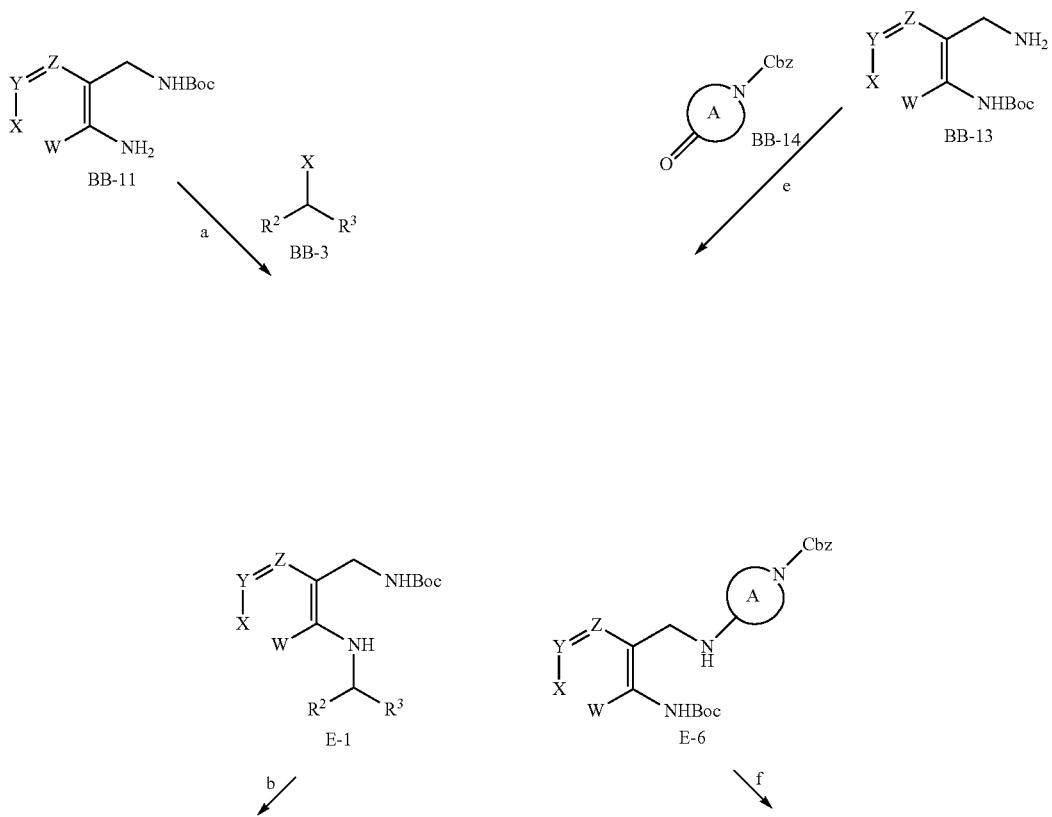

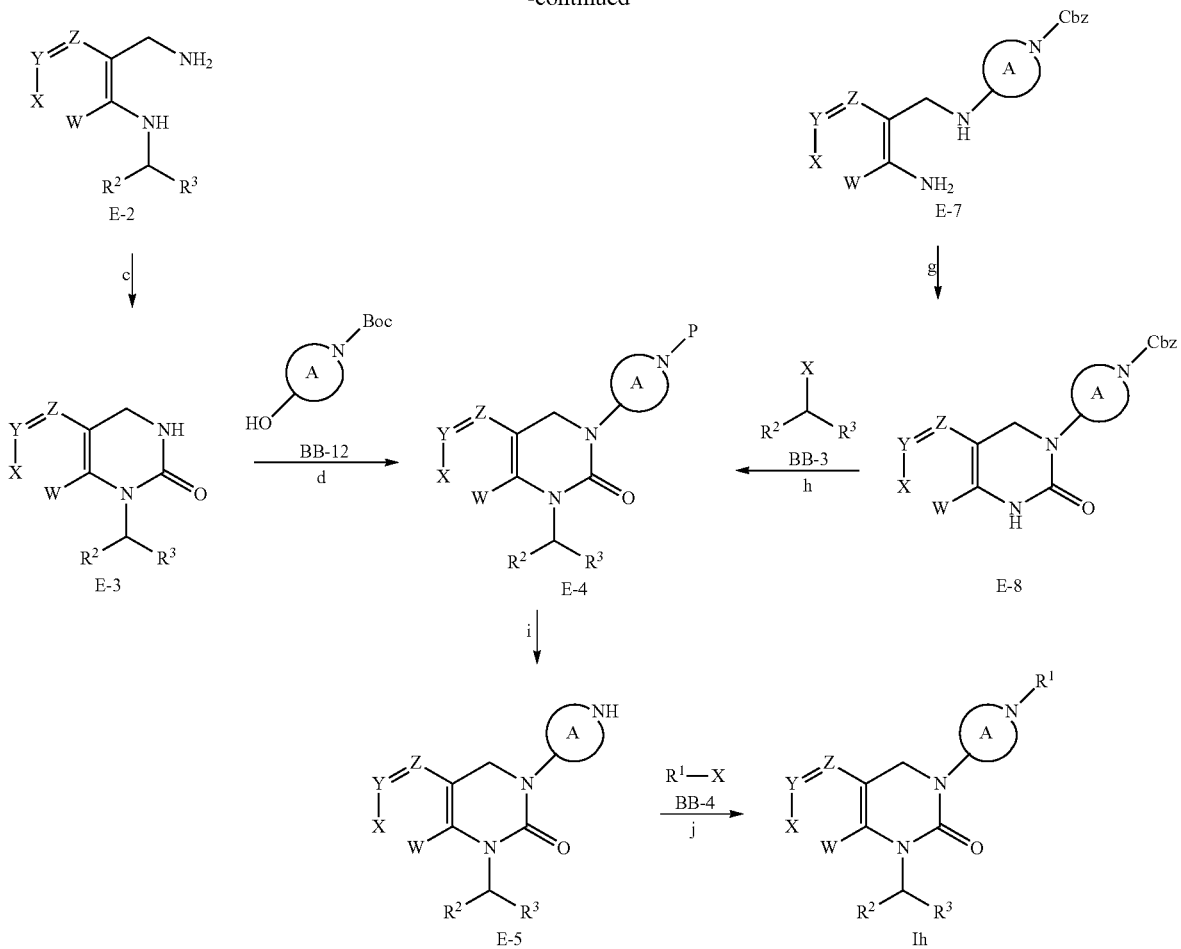

Cyclisation of diamines of structure E-7 by treatment with a suitable carbonyl transfer agent such as CDI in the presence of a suitable aprotic solvent such as MeCN at temperatures around RT may afford compounds of structure E-8 (Scheme E, step g).

Compounds of structure E-4 wherein P represents CBz can be prepared by alkylation of the nitrogen atom having a free valency in compounds of structure E-8 with a suitable halide of structure BB-3 wherein X represents chlorine or bromine, in the presence of a suitable base such as NaH or $K_2CO_3$ and in solvents such as THF, DMF or a mixture of both at temperatures between 0° C. and 50° C. may afford (Scheme E, step h).

Cleavage of the Boc protecting group in compounds of structure E-4 wherein P represents Boc can be performed using a suitable acid such as HCl or TFA in the presence of a suitable solvent such as dioxane, MeOH or DCM at temperatures around RT to afford amines of structure E-5. Alternatively, cleavage of the Cbz protecting group in compounds of structure E-4 wherein P represents Cbz can be performed by catalytic hydrogenation with a suitable catalyst such as Pd/C in the presence of a suitable solvent such as EtOAc, EtOH or a mixture thereof at temperatures around RT (Scheme E, step i).

Compounds of structure Ih wherein $R^1$ represents a mono-, di- or tri-substituted phenyl or 5- or 6-membered heteroaryl can be prepared by Buchwald-Hartwig cross coupling of halides BB-4 of structure $R^1$—X wherein X represents iodine, bromine or chloride and $R^1$ represents a mono-, di- or tri-substituted phenyl or 5- or 6-membered heteroaryl with an amine of structure E-5 in the presence of a suitable palladium catalyst such as $Pd_2(dba)_3$ and a ligand such as BINAP, in the presence of a suitable base such as sodium tert-butoxide and heating in a suitable solvent such as toluene at temperatures between 100° C. and 110° C. (Scheme E, step j).

If not commercially available, ketones of structure BB-7 and amines of structure BB-9 can be prepared according to the synthetic route given in scheme F below.

Compounds of structure F-2 wherein $R^1$ represents a mono-, di- or tri-substituted phenyl or 5- or 6-membered heteroaryl can be prepared by Buchwald-Hartwig cross coupling of halides of structure $R^1$—X wherein X represents iodine, bromine or chloride and $R^1$ represents a mono-, di- or tri-substituted phenyl or 5- or 6-membered heteroaryl with an amine of structure F-1 in the presence of a suitable palladium catalyst such as $Pd_2(dba)_3$ and a ligand such as BINAP, in the presence of a suitable base such as sodium tert-butoxide and heating in a suitable solvent such as toluene at temperatures between 100° C. and 110° C. (Scheme F, step a).

Alternatively, compounds of structure F-2 wherein $R^1$ represents a mono-, di- or tri-substituted phenyl or 5- or 6-membered heteroaryl can be prepared by aromatic nucleophilic substitution of amines of structure F-1 on activated halides of structure $R^1$—X wherein X represents fluorine or chlorine and R¹ represents a suitable mono-, di- or tri-substituted phenyl or 5- or 6-membered heteroaryl in the presence of a suitable base such as K₂CO₃ and heating in a suitable solvent such as DMSO at temperatures between 60° C. and 110° C. (Scheme F, step a).

Cleavage of the ketal protecting group in compounds of structure F-2 by acidic hydrolysis in the presence of a suitable acid such as aq. HCl and heating in a suitable solvent such as THF at temperatures around 70° C. may afford ketones of structure BB-7 (Scheme F, step b).

Compounds of structure F-4 wherein R¹ represents a mono-, di- or tri-substituted phenyl or 5- or 6-membered heteroaryl can be prepared by aromatic nucleophilic substitution of amines of structure F-3 on activated halides of structure R¹—X wherein X represents fluorine or chlorine and R¹ represents a suitable mono-, di- or tri-substituted phenyl or 5- or 6-membered heteroaryl in the presence of a suitable base such as K₂CO₃ and heating in a suitable solvent such as DMSO at temperatures between 60° C. and 110° C. (Scheme F, step c).

Compounds of structure F-4 wherein R¹ represents a mono-, di- or tri-substituted phenyl which is substituted by one methyl group at the ortho position of the connecting nitrogen can be prepared following a four-step procedure: (i) aromatic nucleophilic substitution of amines of structure F-3 on halides of structure R¹—X wherein X represents fluorine or chlorine and R¹ represents a suitable mono-, di- or tri-substituted phenyl which is substituted by one formyl group at the ortho position of the halogen atom X in the presence of a suitable base such as K₂CO₃ and heating in a suitable solvent such as DMSO at temperatures between 60° C. and 110° C. and (ii) consecutive reduction of the benzaldehyde derivative by treatment with a suitable reducing reagent such as NaBH₄ in the presence of a suitable solvent such as MeOH at temperatures between 0° C. and RT and (iii) consecutive acetylation of the resulting benzyl alcohol by treatment with acetyl chloride in the presence of a suitable base such as TEA and in a suitable solvent such as DCM at temperatures between 0° C. and RT and (iv) final catalytic hydrogenation of the resulting benzyl ester with a suitable catalyst such as Pd/C in the presence of a suitable solvent such as EtOAc, MeOH or a mixture thereof at temperatures around RT (Scheme F, step c).

Cleavage of the Boc protecting group in compounds of structure F-4 can be performed using a suitable acid such as HCl or TFA in the presence of a suitable solvent such as dioxane, MeOH or DCM at temperatures around RT to afford amines of structure BB-9 (Scheme F, step d).

Transformation of ketones of structure BB-7 to amines of structure BB-9 can be achieved by reductive amination with for instance aq. ammonia under catalytic hydrogenation conditions using a suitable catalyst such as Pd/C in the presence of a suitable solvent such as dioxane at temperatures around RT (Scheme F, step e).

Scheme F

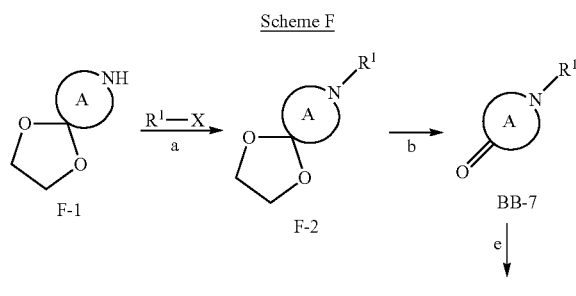

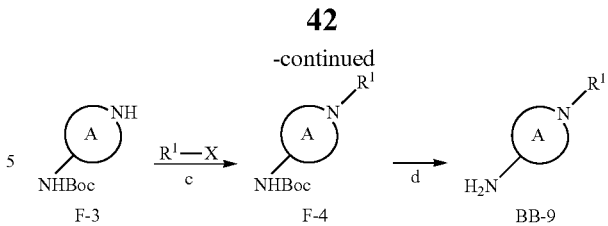

EXPERIMENTAL PART

I. Chemistry

All temperatures are stated in ° C. Commercially available starting materials were used as received without further purification. When an example compound or intermediate is obtained as a racemic mixture of two enantiomers, the corresponding example compound's name or precursor's name is preceded with the mention rac.

Characterization of Compounds

Compounds described in the invention are characterized by LC-MS data (retention time $t_R$ is given in min) and/or NMR using the conditions described below.

Analytical LC-MS:

LC-MS (Method I): Dionex Ultimate 3000 system with Dionex HPG-3200RS binary pump, Thermo MSQ Plus MS detector and Dionex DAD-3000RS PDA detector.

Eluents (acidic conditions): A: H₂O+0.04% TFA; B: MeCN; gradient: 5% B→95% B; runtime: 1.5 min; flow: 4.5 mL/min; detection: UV/Vis+MS Column Agilent Zorbax SB-aq, 4.6×50 mm, 3.5 μm LC-MS (Method II): Waters Acquity UPLC i-Class system with Waters i-Class BSM binary pump, Thermo MSQ Plus MS detector and Waters Acquity PDA detector.

Eluents (acidic conditions): A: H₂O+0.04% TFA; B: MeCN; gradient: 5% B→95% B; runtime: 1.2 min; flow: 0.8 mL/min; detection: UV/Vis+MS Column Agilent Zorbax RRHD SB-aq, 2.1×50 mm, 1.8 μm.

LC-MS (Method III): Dionex Ultimate 3000 system with Dionex HPG-3200SD binary pump, Thermo MSQ Plus MS detector and Dionex DAD-3000RS PDA detector.

Eluents (basic conditions): A: H₂O+13 mmol/L NH₄OH; B: MeCN; gradient: 5% B→95% B; runtime: 1.9 min; flow: 1.6 mL/min; detection: UV/Vis+MS Column Waters BEH C₁₈, 3.0×50 mm, 2.5 μm NMR spectroscopy:

Bruker Avance HD spectrometer equipped with a 500 MHz Ultrashield™ Magnet and a 5 mm DCH cryoprobe or Bruker Avance II spectrometer equipped with a 400 MHz Ultrashield™ Magnet and a BBO 5 mm probehead. Chemical shifts (δ) are reported in parts per million (ppm) relative to proton resonances resulting from incomplete deuteration of the NMR solvent, e.g. for dimethylsulfoxide δ(H) 2.49 ppm, for chloroform δ(H) 7.24 ppm. The abbreviations s, d, t, q and m refer to singlet, doublet, triplet, quartet, multiplet, respectively and br to broad. Coupling constants J are reported in Hz.

Purification of Compounds

The compounds were purified by either column chromatography on silica-gel and/or prep. LC-MS using the conditions described below.

Column Chromatography

Column chromatography (CC) was performed using pre-packed cartridges (SNAP Ultra™, SNAP KP-SIL™, SNAP KP-NH™, Isolute™ Silica II or Isolute™ NH₂) from Biotage.

Preparative LC-MS:

Gilson 333/334 Prep-Scale HPLC pump equipped with Gilson LH215 autosampler, Dionex SRD-3200 degasser, Dionex ISO-3100A make-up pump, Dionex DAD-3000 DAD detector and Thermo MSQ Plus Single Quadrupole MS detector. Flow: 75 mL/min. Detection: UV/Vis and/or MS.

Additional informations for the purification are summerized in the table below using following explanations:

XBridge: column Waters XBridge C18, 10 μm, 30×75 mm

Acidic: eluant: A=H$_2$O with 0.5% HCOOH, B=MeCN
Basic: eluant: A=H$_2$O with 0.125% NH$_4$OH, B=MeCN
Very lipophilic gradient: 50% B→95% B over 4 min then 95% B over 2 min
Lipophilic gradient: 30% B→95% B over 4 min then 95% B over 2 min
Normal gradient: 20% B→95% B over 4 min then 95% B over 2 min
Polar gradient: 10% B→95% B over 4 min then 95% B over 2 min
Very polar gradient: 5% B→50% B over 3 min then 50% B→95% B over 1 min and finally 95% B over 2 min

|  | XBridge | |
| --- | --- | --- |
|  | acidic | basic |
| Very lipophilic gradient | Method 2 |  |
| Lipophilic gradient | Method 3 | Method 1 |
| Normal gradient | Method 4 |  |
| Polar gradient | Method 5 |  |

ABBREVIATIONS (AS USED HEREINBEFORE OR HEREINAFTER)

Ac acetyl
AcOH acetic acid
AIBN azobisisobutyronitrile
aq. aqueous
BINAP racemic 2,2'-bis(diphenylphosphino)-1,1'-binaphthyl
Boc tert.-butyloxycarbonyl
Cbz benzyloxycarbonyl
CC column chromatography
CDI carbonyl diimidazole
CPhos 2-dicyclohexylphosphino-2',6'-bis(N,N-dimethylamino)biphenyl
DCM dichloromethane
dioxane 1,4-dioxane
DIPEA diisopropylethylamine
DMF dimethylformamide
DMSO dimethylsulfoxide
eq equivalent(s)
EtOAc ethyl acetate
EtOH ethanol
Et$_2$O diethylether
g gram(s)
h hour(s)
Hept heptane
HPLC high performance liquid chromatography
LC-MS liquid chromatography-mass spectrometry
MeCN acetonitrile
MeOH methanol
mg milligram(s)
min minute(s)
mL milliliter(s)
mmol millimole(s)
MS mass spectroscopy
NaBH(OAc)$_3$ sodium triacetoxyborohydride
NBS N-bromosuccinimide
NCS N-chlorosuccinimide
NMR nuclear magnetic resonance spectroscopy
OAc acetate
org. organic
ON overnight
PEPPSI-IPr [1,3-bis(2,6-Diisopropylphenyl)imidazol-2-ylidene](3-chloropyridyl)palladium(II) dichloride
Pd$_2$(dba)$_3$ tris(dibenzylideneacetone)dipalladium(0)
prep. preparative
rac racemic
RT room temperature
rxn reaction
sat. saturated
soln. solution
TEA triethylamine
TFA trifluoroacetic acid
TFE trifluoroethanol
THF tetrahydrofuran
t$_R$ retention time When not commercially available, the building blocks were prepared according to the procedures described below.

Synthesis of Building Blocks BB-3

Synthesis of 2-bromomethyl-3-trifluoromethyl-pyrazine (BB-3-1)

A suspension of methyl-heteroarene (1 eq) in chlorobenzene (4 mL/mmol) was heated to 50° C. and NBS (1.3 eq) was added portionwise at 50° C. (see Table 1). The flask was purged with argon and AIBN (0.1 eq) was added in one portion. The rxn mixture was heated to 80° C. and stirred for 6 h. After cooling to RT, the mixture was diluted with Et$_2$O and washed with a 1M aq. soln. of HCl (3×). The org. phase was washed with brine, dried over MgSO$_4$ and concentrated in vacuo. The crude was purified by CC using Hept/EtOAc.

TABLE 1

| BB-3 | Name | Methyl-heteroarene | t$_R$ [min] (LC/MS method) | $^1$H NMR (400 MHz, DMSO-d6) δ: |
| --- | --- | --- | --- | --- |
| BB-3-1 | 2-Bromomethyl-3-trifluoromethyl-pyrazine | 2-Methyl-3-trifluoromethyl pyrazine | 0.76 (I) | 9.03(d, J = 2.2 Hz, 1 H), 8.84(d, J = 2.3 Hz, 1 H), 4.84(d, J = 0.9 Hz, 2 H) |

Synthesis of building blocks BB-3-2, BB-3-3, BB-3-4, BB-3-5, BB-3-6

Step A: Esterification

To a soln. of carboxylic acid (1 eq) in anh. MeOH (4 mL/mmol) was added AcCl (3 eq) and the rxn mixture was stirred for 2.5 h at 80° C. (see Table 2). MeOH was evaporated off and the residue was partitioned between a sat. soln. of NaHCO$_3$ and EtOAc. The org. phase was washed with a 10% aq. soln. of Na$_2$CO$_3$ (1×) and with brine (1×), dried over MgSO$_4$ and concentrated in vacuo.

TABLE 2

| BB-3A | Name | Carboxylic acid reactant | $t_R$ [min] (LC/MS method) | MS-data m/z $[M + H]^+$ |
|---|---|---|---|---|
| BB-3-2A | 3-Isopropoxy-pyrazine-2-carboxylic acid methyl ester | 3-Isopropoxy-pyrazine-2-carboxylic acid | 0.70 (I) | 197.17 |
| BB-3-3A | 3-Isopropoxy-pyridine-2-carboxylic acid methyl ester | 3-Isopropoxy-pyridine-2-carboxylic acid | 0.64 (I) | 196.21 |

Step A (Negishi): synthesis of 3-isopropyl-pyrazine-2-carboxylic acid ethyl ester (BB-3-5A)

An oven dried flask was charged with 3-chloropyrazine-2-carboxylic acid ethyl ester (500 mg, 2.63 mmol), PEPPSI-IPr (18 mg, 0.026 mmol) and CPhos (12 mg, 0.026 mmol). The flask was evacuated and refilled with argon (3×) and toluene (5 mL) was added. The rxn mixture was cooled to 0° C. and a 0.5M soln. of 2-propyl zinc bromide in THF (6.83 mL, 3.41 mmol) was added dropwise. The rxn mixture was stirred for 72 h at RT and partitioned between half sat. brine and DCM. The org. phase was dried over $MgSO_4$ and concentrated in vacuo. The crude was purified by CC using Hept/EtOAc.

LC-MS (I): $t_R$=0.74 min, $[M+H]^+$: 195.18

Final Step: Methyl/Ethyl Ester Reduction Using $CaCl_2$/$NaBH_4$

To a soln. of methyl or ethyl ester BB-3A (1 eq) in anh. EtOH (15 mL/mmol) was added $CaBH_2$ (0.3 eq) and the rxn mixture was cooled to −10° C. $NaBH_4$ (2.5 eq) was added portionwise and the mixture was stirred for 30 min at −10° C. and for a given time at a given temperature (see Table 3). It was quenched at 0° C. with water and EtOH was evaporated off. The residue was partitioned between EtOAc and water and the aq. phase was further extracted with EtOAc (2×). The combined org. phases were washed with brine (1×), dried over $MgSO_4$ and concentrated in vacuo. When necessary the crude was purified by CC using DCM/MeOH.

Step B: 4-Isopropoxy-pyridazine-3-carboxylic acid isopropyl ester

To a soln. of 6-chloro-4-isopropoxy-pyridazine-3-carboxylic acid isopropyl ester (239 mg, 0.92 mmol) in EtOH (3 mL) was added ammonium formate (119 mg, 1.83 mmol) and the rxn mixture was flushed with nitrogen. Wet Pd/C (49 mg, 0.05 eq) was added and after inertising with nitrogen the rxn mixture was heated to 60° C. and stirred for 1 h. It was filtered over a pad of Celite, the cake was washed with MeOH and the filtrate was concentrated in vacuo. The crude was purified by CC using Hept/EtOAc.

LC-MS (II): $t_R$=0.74 min, $[M+H]^+$: 225.16

Final step: (4-Isopropoxy-pyridazin-3-yl)-methanol (BB-3-7)

To a soln. of 4-isopropoxy-pyridazine-3-carboxylic acid isopropyl ester (139 mg, 0.62 mmol) in anh. EtOH (9.3 mL) was added $CaCl_2$ (21 mg, 0.19 mmol) and the rxn mixture was cooled to −10° C. $NaBH_4$ (59 mg, 1.55 mmol) was added portionwise and the mixture was stirred for 30 min at −10° C. and for 5 h at RT. It was quenched at 0° C. with water and EtOH was evaporated off. The residue was partitioned between EtOAc and water and the aq. phase was further extracted with EtOAc (2×). The combined org. phases were washed with brine (1×), dried over $MgSO_4$ and concentrated in vacuo.

LC-MS (II): $t_R$=0.33 min, $[M+H]^+$: 169.04

TABLE 3

| BB-3 | Name | Methyl/ethyl ester reactant | T [° C.] time [h] | $t_R$ [min] (LC/MS method) | MS-data m/z $[M + H]^+$ |
|---|---|---|---|---|---|
| BB-3-2 | (3-Isopropoxy-pyrazin-2-yl)-methanol | BB-3-2A | RT 0.5 | 0.58 (I) | 169.11 |
| BB-3-3 | (3-Isopropoxy-pyridin-2-yl)-methanol | BB-3-3A | RT 24 | 0.40 (I) | 168.47 |
| BB-3-4 | (4-Isopropyl-pyridin-3-yl)-methanol | 4-(1-Methylethyl) pyridine-3-carboxylic acid ethyl ester | RT 48 | 0.34 (I) | 152.45 |
| BB-3-5 | (3-Isopropyl-pyrazin-2-yl)-methanol | BB-3-5A | 0 2.5 | 0.48 (I) | 153.45 |
| BB-3-6 | (4-Isopropyl-pyrimidin-5-yl)-methanol | 4-Isopropyl pyrimidine-5-carboxylic acid ethyl ester | 70 1 | 0.46 (I) | 153.47 |

Synthesis of (4-isopropoxy-pyridazin-3-yl)-methanol (BB-3-7)

Step A: 6-Chloro-4-isopropoxy-pyridazine-3-carboxylic acid isopropyl ester

To a soln. of 4,6-dichloropyridazine-3-carboxylic acid methyl ester (1000 mg, 4.83 mmol) in anh. THF (24 mL) was added dropwise at 0° C. a 2M soln. of lithium isopropoxide in THF (2.54 mL, 5.07 mmol). The rxn mixture was stirred for 1 h at 0° C. and poured into a 1M aq. soln. of HCl. The aq. soln. was neutralized with a sat. aq. soln. of $NaHCO_3$ and extracted with EtOAc (3×). The combined org. phases were washed with brine, dried over $MgSO_4$ and concentrated in vacuo. The crude was purified by CC using Hept/EtOAc.

LC-MS (II): $t_R$=0.88 min, $[M+H]^+$: 259.03

Synthesis of Building Blocks BB-7

Step A: Buchwald Hartwig

To a mixture of the appropriate amine F-1 (1 eq), the appropriate halide (1.2 eq) and sodium tert-butoxide (2 eq) in toluene (3 mL/mmol) under N2, was added BINAP (0.2 eq) and $Pd_2(dba)_3$ (0.1 eq) (see Table 4). The rxn mixture was flushed with N2, heated to 100° C. in a sealed vial and stirred for 24 h. It was partitioned between water and EtOAc and the org. phase was washed with brine, dried over $MgSO_4$ and concentrated in vacuo. The crude was purified by CC using Hept/EtOAc.

TABLE 4

| F-2 | Name | Reactant F-1 | Reactant haloarene | $t_R$ [min] (LC/MS method) | MS-data m/z [M + H]$^+$ |
|---|---|---|---|---|---|
| F-2-1 | 8-(2-Fluoro-6-methyl-phenyl)-1,4-dioxa-8-aza-spiro[4.5]decane | 1,4-Dioxa-8-azaspiro[4.5]decane | 2-Bromo-3-fluorotoluene | 0.92 (I) | 252.07 |

Final Step: Ketal Cleavage

To a soln. of ketal intermediate F-2 (1 eq) in anh. THF (3 mL/mmol) was added a 1M aq. soln. of HCl (2 mL/mmol) at RT (see Table 5). The rxn mixture was heated to 70° C. and stirred for 24 h. It was quenched with a sat. aq. soln. of NaHCO$_3$ and extracted with EtOAc (3×). The combined org. phases were washed with brine, dried over MgSO$_4$ and concentrated in vacuo. The crude was purified by CC using Hept/EtOAc.

TABLE 5

| BB-7 | Name | Reactant F-2 | $t_R$ [min] (LC/MS method) | MS-data m/z [M + H]$^+$ |
|---|---|---|---|---|
| BB-7-1 | 1-(2-Fluoro-6-methyl-phenyl)-piperidin-4-one | F-2-1 | 0.86 (I) | 208.11 |

Synthesis of Building Blocks BB-9

Step A: Aromatic Nucleophilic Substitution

To a soln. of the appropriate amine F-3 (1 eq) and the appropriate fluoroarene (1.1 eq) in DMSO (0.9 mL/mmol) was added K$_2$CO$_3$ (2 eq) and the mixture was heated to 105° C. and stirred for 18 h (see Table 6). It was quenched with water and extracted with DCM. The org. phase was washed with water (5×) and brine (1×), dried over MgSO$_4$ and concentrated in vacuo. The crude was purified by CC using DCM/MeOH.

TABLE 6

| BB-9A | Name | Reactant F-3 | Reactant fluoroarene | $t_R$ [min] (LC/MS method) | MS-data m/z [M + H]$^+$ |
|---|---|---|---|---|---|
| BB-9-1A | [1-(2-Fluoro-6-formyl-phenyl)-piperidin-4-yl]-carbamic acid tert-butyl ester | 4-(N-Boc-amino)piperidine | 2,3-Difluoro benzaldehyde | 0.93 (I) | 323.20 |

Step B: Reduction

A suspension of intermediate BB-9A (1 eq) in anh. MeOH (2 mL/mmol) was cooled to 0° C. and NaBH$_4$ (1.3 eq) was added portionwise at 0° C. (see Table 7). The rxn mixture was stirred for 1 h at 0° C. to reach completion. It was carefully quenched by dropwise addition of water at 0° C. and extracted with EtOAc. The org. phase was washed with water and brine, dried over MgSO$_4$ and concentrated in vacuo.

TABLE 7

| BB-9B | Name | Reactant BB-9A | $t_R$ [min] (LC/MS method) | MS-data m/z [M + H]$^+$ |
|---|---|---|---|---|
| BB-9-1B | [1-(2-Fluoro-6-hydroxymethyl-phenyl)-piperidin-4-yl]-carbamic acid tert-butyl ester | BB-9-1A | 0.82 (I) | 325.24 |

Step C: Acetylation

A soln. of intermediate BB-9B (1 eq) and TEA (1.5 eq) in DCM (0.5 mL/mmol) was cooled to 0° C. and AcCl (1.5 eq) was added dropwise at 0° C. (see Table 8). The rxn mixture was stirred for 1 h at 0° C. to reach completion. It was diluted with DCM and washed with a 10% aq. soln. of citric acid (2×), with a sat. aq. soln. of NaHCO$_3$ (2×) and with brine (1×). The org. phase was dried over MgSO$_4$ and concentrated in vacuo. The crude was purified by CC using Hept/EtOAc.

TABLE 8

| BB-9C | Name | Reactant BB-9B | $t_R$ [min] (LC/MS method) | MS-data m/z [M + H]$^+$ |
|---|---|---|---|---|
| BB-9-1C | Acetic acid 2-(4-tert-butoxycarbonylamino-piperidin-1-yl)-3-fluoro-benzyl ester | BB-9-1B | 0.97 (I) | 367.25 |

Step D: Hydrogenation

Intermediate BB-9C (1 eq) was dissolved in a mixture of MeOH (6 mL/mmol) and EtOAc (2 mL/mmol) and the flask was evacuated three times and refilled with nitrogen (see Table 9). Wet Pd/C (0.08 eq) was added and the flask was evacuated three times and refilled with hydrogen. The suspension was hydrogenated under atmospheric pressure for 3 h and filtered over a pad of Celite. The cake was washed with EtOAc and MeOH and the filtrate was concentrated in vacuo. The crude was purified by CC using Hept/EtOAc.

TABLE 9

| F-4 | Name | Reactant BB-9C | $t_R$ [min] (LC/MS method) | MS-data m/z [M + H]$^+$ |
|---|---|---|---|---|
| F-4-1 | [1-(2-Fluoro-6-methyl-phenyl)-piperidin-4-yl]-carbamic acid tert-butyl ester | BB-9-1C | 1.00 (I) | 309.16 |

Final Step: Boc Cleavage

To a soln. of intermediate F-4 (1 eq) in DCM (4 mL/mmol) was added dropwise TFA (1 mL/mmol) and the rxn mixture was stirred for 1 h to 18 h at RT (see Table 10). It was basified with a 1M aq. soln. of NaOH until pH 12-13 and extracted with DCM (3×). The combined org. phases were dried over MgSO$_4$ and concentrated in vacuo.

TABLE 10

| BB-9 | Name | Reactant F-4 | $t_R$ [min] (LC/MS method) | MS-data m/z [M + H]$^+$ |
|---|---|---|---|---|
| BB-9-1 | 1-(2-Fluoro-6-methyl-phenyl)-piperidin-4-ylamine | F-4-1 | 0.60 (I) | 209.28 |

Synthesis of Intermediates of Formula A-1

A soln. of BB-1 (1 eq) and BB-2 (1 eq) in anh. MeOH (2 mL/mmol) was heated to 60° C. and stirred for 4 h (see Table 11). The rxn mixture was cooled to 0° C. and NaBH$_4$ (1 eq) was added. It was stirred for 2 to 18 h until completion allowing temperature to slowly reach RT. It was quenched with a sat. aq. soln. of NaHCO$_3$ and extracted with DCM (3×). The combined org. phases were dried over MgSO$_4$ and concentrated in vacuo. The crude was purified by CC using Hept/EtOAc.

TABLE 11

| A-1 | Name | Reactant BB-1 | Reactant BB-2 | $t_R$ [min] (LC/MS method) | MS-data m/z [M + H]$^+$ |
|---|---|---|---|---|---|
| A-1-2 | 4-(3-Methoxy-2-nitro-benzylamino)-piperidine-1-carboxylic acid tert-butyl ester | 3-Methoxy-2-nitrobenzaldehyde | 1-N-BOC-4-aminopiperidine | 0.66 (I) | 366.00 |
| A-1-3 | (R)-3-(3-Methoxy-2-nitro-benzylamino)-pyrrolidine-1-carboxylic acid tert-butyl ester | 3-Methoxy-2-nitrobenzaldehyde | (R)-(+)-1-BOC-3-aminopyrrolidine | 0.64 (I) | 352.04 |

Synthesis of Intermediates of Formula A-2

To a soln. of intermediate A-1 (1 eq) in EtOAc (3 mL/mmol) was added 10% Pd/C moistened with ~50% water (0.01 to 0.05 eq) and the rxn mixture was hydrogenated under atmospheric pressure for a given time (see Table 12). It was filtered over a pad of celite and the filtrate was concentrated in vacuo.

TABLE 12

| A-2 | Name | Reactant A-1 | time [h] | $t_R$ [min] (LC/MS method) | MS-data m/z [M + H]$^+$ |
|---|---|---|---|---|---|
| A-2-2 | 4-(2-Amino-3-methoxy-benzylamino)-piperidine-1-carboxylic acid tert-butyl ester | A-1-2 | 3 | 0.63 (I) | 336.08 |
| A-2-3 | (R)-3-(2-Amino-3-methoxy-benzylamino)-pyrrolidine-1-carboxylic acid tert-butyl ester | A-1-3 | 18 | 0.61 (I) | 321.98 |

Synthesis of Intermediates of Formula A-3

To a soln. of intermediate A-2 (1 eq) in MeCN (3.7 mL/mmol) was added CDI (1.1 eq) and the rxn mixture was stirred at RT for a given time (see Table 13). The solvent was evaporated off and the residue was partitioned between DCM and water. The org. phase was washed with brine, dried over MgSO$_4$ and concentrated in vacuo. The crude was purified by CC using Hept/EtOAc.

TABLE 13

| A-3 | Name | Reactant A-2 | time [h] | $t_R$ [min] (LC/MS method) | MS-data m/z [M + H]$^+$ |
|---|---|---|---|---|---|
| A-3-2 | 4-(8-Methoxy-2-oxo-1,4-dihydro-2H-quinazolin-3-yl)-piperidine-1-carboxylic acid tert-butyl ester | A-2-2 | 1 | 0.87 (I) | 362.19 |
| A-3-3 | (R)-3-(8-Methoxy-2-oxo-1,4-dihydro-2H-quinazolin-3-yl)-pyrrolidine-1-carboxylic acid tert-butyl ester | A-2-3 | 3 | 0.84 (I) | 348.06 |

Synthesis of Intermediates of Formula A-4

To a soln. of intermediate A-3 (1 eq) in anh. THF (3 mL/mmol) was added NaH (2 to 5 eq, as a 60% dispersion in mineral oil) at RT followed by BB-3 (1.2 eq). When necessary in terms of solubility, anh. DMF (0.1 to 2 mL/mmol) could be added. The rxn mixture was stirred at a given temperature for a given time (see Table 14), quenched with a sat. aq. soln. of NaHCO$_3$ and extracted with EtOAc (3×). The combined org. phases were washed with brine, dried over MgSO$_4$ and concentrated in vacuo. The crude was purified by CC using Hept/EtOAc.

TABLE 14

| A-4 | Name | Reactant A-3 | Reactant BB-3 | T [° C.] time [h] | $t_R$ [min] (LC/MS-Method) | MS-data m/z [M + H]+ |
|---|---|---|---|---|---|---|
| A-4-1 | 4-[2-Oxo-1-(2-trifluoromethyl-benzyl)-1,4-dihydro-2H-quinazolin-3-yl]-piperidine-1-carboxylic acid tert-butyl ester | tert-Butyl 4-(2-oxo-1,2,3,4-tetrahydroquinazolin-3-yl)piperidine-1-carboxylate | 2-(Trifluoromethyl) benzyl bromide | RT 24 | 1.04 (I) | 489.98 |
| A-4-2 | 4-[8-Methoxy-2-oxo-1-(2-trifluoromethyl-benzyl)-1,4-dihydro-2H-quinazolin-3-yl]-piperidine-1-carboxylic acid tert-butyl ester | A-3-2 | 2-(Trifluoromethyl) benzyl bromide | RT 24 | 1.04 (I) | 519.89 |
| A-4-3 | (R)-3-[8-Methoxy-2-oxo-1-(2-trifluoromethyl-benzyl)-1,4-dihydro-2H-quinazolin-3-yl]-pyrrolidine-1-carboxylic acid tert-butyl ester | A-3-3 | 2-(Trifluoromethyl) benzyl bromide | RT 72 | 1.03 (I) | 505.94 |
| A-4-4 | (S)-3-[2-Oxo-1-(2-trifluoromethyl-benzyl)-1,4-dihydro-2H-quinazolin-3-yl]-pyrrolidine-1-carboxylic acid tert-butyl ester | tert-Butyl (3S)-3-(2-oxo-1,2,3,4-tetrahydroquinazolin-3-yl)pyrrolidine-1-carboxylate | 2-(Trifluoromethyl) benzyl bromide | RT 72 | 1.02 (I) | 476.09 |
| A-4-5 | (R)-3[2-Oxo-1-(2-trifluoromethyl-benzyl)-1,4-dihydro-2H-quinazolin-3-yl]-pyrrolidine-1-carboxylic acid tert-butyl ester | tert-Butyl (3R)-3-(2-oxo-1,2,3,4-tetrahydroquinazolin-3-yl)pyrrolidine-1-carboxylate | 2-(Trifluoromethyl) benzyl bromide | RT 72 | 1.02 (I) | 476.09 |
| A-4-6 | (R)-3-[1-(2-Methoxy-benzyl)-2-oxo-1,4-dihydro-2H-quinazolin-3-yl]-pyrrolidine-1-carboxylic acid tert-butyl ester | tert-Butyl (3R)-3-(2-oxo-1,2,3,4-tetrahydroquinazolin-3-yl)pyrrolidine-1-carboxylate | 2-Methoxy benzyl chloride | RT 30 | 0.98 (I) | 438.23 |
| A-4-7 | 4-[1-(2-Methoxy-benzyl)-2-oxo-1,4-dihydro-2H-quinazolin-3-yl]-piperidine-1-carboxylic acid tert-butyl ester | tert-Butyl 4-(2-oxo-1,2,3,4-tetrahydroquinazolin-3-yl)piperidine-1-carboxylate | 2-Methoxy benzyl chloride | RT 48 | 1.00 (I) | 452.19 |

Synthesis of Intermediates of Formula A-5

To a soln. of intermediate A-4 (1 eq) in DCM (2 to 10 mL/mmol) was added TFA (0.75 to 2 mL/mmol) at 0° C. and the rxn mixture was stirred at RT for a given time (see Table 15). It was cooled to 0° C. and quenched with a 1M aq. soln. of NaOH until pH reached 12 to 13 and extracted with DCM (3×). The combined org. phases were washed with brine, dried over MgSO$_4$ and concentrated in vacuo. The crude was purified by CC using DCM/MeOH or by prep. LC-MS using method 1.

Synthesis of Intermediates of Formula A-7

Method A (SN$_{Ar}$ Alone)

To a soln. of the appropriate amine A-6 (1 eq) (when using an amine as HCl salt TEA (1 eq) was added) and the appropriate fluoroarene BB-4 (1.2 eq) in DMSO (1.5 mL/mmol) was added K$_2$CO$_3$ (2 eq) and the mixture was heated to 100° C. and stirred for a given time (see Table 16). It was partitioned between DCM and H$_2$O and the org. phase was washed with water (5×) and brine (1×), dried over

TABLE 15

| A-5 | Name | Reactant A-4 | time [h] | $t_R$ [min] (LC/MS-method) | MS-data m/z [M + H]+ |
|---|---|---|---|---|---|
| A-5-1 | 3-Piperidin-4-yl-1-(2-trifluoromethyl-benzyl)-3,4-dihydro-1H-quinazolin-2-one | A-4-1 | 2.5 | 0.70 (I) | 389.95 |
| A-5-2 | 8-Methoxy-3-piperidin-4-yl-1-(2-trifluoromethyl-benzyl)-3,4-dihydro-1H-quinazolin-2-one | A-4-2 | 2.5 | 0.73 (I) | 420.11 |
| A-5-3 | 8-Methoxy-3-(R)-pyrrolidin-3-yl-1-(2-trifluoromethyl-benzyl)-3,4-dihydro-1H-quinazolin-2-one | A-4-3 | 2 | 0.74 (I) | 406.13 |
| A-5-4 | 3-(S)-Pyrrolidin-3-yl-1-(2-trifluoromethyl-benzyl)-3,4-dihydro-1H-quinazolin-2-one | A-4-4 | 1 | 0.73 (I) | 375.99 |
| A-5-5 | 3-(R)-Pyrrolidin-3-yl-1-(2-trifluoromethyl-benzyl)-3,4-dihydro-1H-quinazolin-2-one | A-4-5 | 1 | 0.73 (I) | 375.99 |
| A-5-6 | 1-(R)-(2-methoxybenzyl)-3-(pyrrolidin-3-yl)-3,4-dihydro-1H-quinazolin-2-one | A-4-6 | 1 | 0.68 (I) | 338.06 |
| A-5-7 | 1-(2-Methoxy-benzyl)-3-piperidin-4-yl-3,4-dihydro-1H-quinazolin-2-one | A-4-7 | 0.2 | 0.67 (I) | 352.18 |

MgSO$_4$ and concentrated in vacuo. The crude was triturated in a mixture of Et$_2$O (3.4 mL/mmol) and MeCN (0.5 mL/mmol) and filtered.

TABLE 16

| A-7 | Name | Reactant A-6 | Reactant BB-4 | time [h] | $t_R$ [min] (LC/MS method) | MS-data m/z [M+H]$^+$ |
|---|---|---|---|---|---|---|
| A-7-1 | 3-Fluoro-2-[4-(2-oxo-1,4-dihydro-2H-quinazolin-3-yl)-piperidin-1-yl]-benzonitrile | 3,4-Dihydro-3-(4-piperidinyl)-2(1H)-quinazolinone hydrochloride | 2,3-Difluoro benzonitrile | 2 | 0.91 (I) | 351.17 |

Method B (Multistep)
Step A: Aromatic Nucleophilic Substitution

To a soln. of the appropriate amine A-6 (1 eq) (when using an amine as HCl salt TEA (1 eq) was added) and the appropriate fluoroarene BB-4 (1.2 eq) in DMSO (1.5 mL/mmol) was added K$_2$CO$_3$ (2 eq) and the rxn mixture was heated to 100° C. and stirred for a given time (see Table 17). It was quenched with water and extracted with DCM. The org. phase was washed with water (5×) and brine (1×), dried over MgSO$_4$ and concentrated in vacuo. The crude was triturated in a mixture of Et$_2$O (3.4 mL/mmol) and MeCN (0.5 mL/mmol) and the solid was filtered.

TABLE 17

| A-7A | Name | Reactant A-6 | Reactant BB-4 | Method time [h] | $t_R$ [min] (LC/MS-Method) | MS-data m/z [M + H]$^+$ |
|---|---|---|---|---|---|---|
| A-7-2A | 3-Fluoro-2-[4-(2-oxo-1,4-dihydro-2H-quinazolin-3-yl)-piperidin-1-yl]-benzaldehyde | 3,4-Dihydro-3-(4-piperidinyl)-2(1H)-quinazolinone hydrochloride | 2,3-Difluoro-benzaldehyde | 18 | 0.90 (I) | 354.19 |

Step B: Reduction

A suspension of intermediate A-7A (1 eq) in anh. MeOH (2 mL/mmol) was cooled to 0° C. and NaBH$_4$ (1.3 eq) was added portionwise at 0° C. The rxn mixture was allowed to reach RT and stirred for a given time (see Table 18). When necessary an additional amount of NaBH$_4$ (1.3 to 2.5 eq) can be added to reach completion. The rxn mixture was carefully quenched by dropwise addition of water at 0° C., the volatiles were evaporated and the residue was extracted with EtOAc. The org. phase was washed with water and brine, dried over MgSO$_4$ and concentrated in vacuo. The crude was purified by CC using Hept/EtOAc.

TABLE 18

| A-7B | Name | Reactant A-7A | time [h] | $t_R$ [min] (LC/MS method) | MS-data m/z [M + H]$^+$ |
|---|---|---|---|---|---|
| A-7-2B | 3-[1-(2-Fluoro-6-hydroxymethyl-phenyl)-piperidin-4-yl]-3,4-dihydro-1H-quinazolin-2-one | A-7-2A | 24 | 0.80 (I) | 356.16 |

Step C: Acetylation

A soln. of intermediate A-7B (1 eq) and TEA (1.5 eq) in DCM (0.5 mL/mmol) was cooled to 0° C. and AcCl (1.5 eq) was added dropwise at 0° C. The rxn mixture was allowed to slowly reach RT and stirred for a given time (see Table 19). It was diluted with DCM and washed with a 10% aq. soln. of citric acid (2×), with a sat. aq. soln. of NaHCO$_3$ (2×) and with brine (1×). The org. phase was dried over MgSO$_4$ and concentrated in vacuo. The crude was purified by CC using DCM/MeOH.

TABLE 19

| A-7C | Name | Reactant A-7B | time [h] | $t_R$ [min] (LC/MS method) | MS-data m/z [M + H]$^+$ |
|---|---|---|---|---|---|
| A-7-2C | Acetic acid 3-fluoro-2-[4-(2-oxo-1,4-dihydro-2H-quinazolin-3-yl)-piperidin-1-yl]-benzyl ester | A-7-2B | 2 | 0.93 (I) | 398.19 |

Final Step: Hydrogenation

Intermediate A-7C (1 eq) was dissolved in a mixture of MeOH (36 mL/mmol) and EtOAc (12 mL/mmol) and the flask was evacuated three times and refilled with nitrogen. Wet Pd/C (0.1 eq) was added and the flask was evacuated and refilled three times with hydrogen. The suspension was hydrogenated under atmospheric pressure for a given time (see Table 20) and filtered over a pad of Celite. The cake was washed with EtOAc and MeOH and the filtrate was concentrated in vacuo. The crude was purified by CC using DCM/MeOH.

TABLE 20

| A-7 | Name | Reactant | time [h] | $t_R$ [min] (LC/MS method) | MS-data m/z [M + H]$^+$ |
|---|---|---|---|---|---|
| A-7-2 | 3-[1-(2-Fluoro-6-methyl-phenyl)-piperidin-4-yl]-3,4-dihydro-1H-quinazolin-2-one | A-7-2C | 72 | 0.97 (I) | 340.05 |

Synthesis of Compounds of Formula Ia

Method A (Buchwald-Hartwig): from compounds of formula A-5

To a mixture of A-5 (1 eq), BB-4 (1.3 eq) and sodium tert-butoxide (2 eq) in toluene (3 to 10 mL/mmol) under N2, was added BINAP (0.2 eq) and Pd$_2$(dba)$_3$ (0.1 eq). The rxn mixture was flushed with N$_2$, heated at a given temperature and stirred for a given time (see Table 21). It was partitioned between water and EtOAc and the org. phase was washed with brine, dried over MgSO₄ and concentrated in vacuo. The crude was purified by CC using Hept/EtOAc. When necessary, an additional purification by prep. LC-MS using method 1, 2, 3 or 4 was performed Method B (N-Alkylation): From Compounds of Formula A-7

To a suspension of intermediate A-7 (1 eq) in anh. THF (3 to 5 mL/mmol) was added NaH (5 eq, as a 60% dispersion in mineral oil) at 0° C. The rxn mixture was stirred for 10 min and BB-3 (1.2 to 1.5 eq) was added at 0° C. When necessary in terms of solubility, anh. DMF (0.1 to 2 mL/mmol) could be added. The rxn mixture was stirred at a given temperature for a given time (see Table 21), quenched with a sat. aq. soln. of NaHCO₃ and extracted with EtOAc (3×). The combined org. phases were washed with brine, dried over MgSO₄ and concentrated in vacuo. The crude was purified by CC using Hept/EtOAc or DCM/MeOH. When necessary, an additional purification by prep. LC-MS using method 3 was performed.

Method C (Mitsunobu): From Compounds of Formula A-7

To a soln. of intermediate A-7 (1 eq) and BB-3 (1.8 eq) in toluene (7 mL/mmol) was added a 1M soln. of (tributylphosphoranylidene)acetonitrile in toluene (2 eq) under argon. The rxn mixture was heated to 110° C. and stirred for a given time (see Table 21). It was quenched with water and extracted with EtOAc (3×). The combined org. phases were washed with brine, dried over MgSO₄ and concentrated in vacuo. The crude was purified by CC using Hept/EtOAc or DCM/MeOH. When necessary, an additional purification by prep. LC-MS using method 3 can be performed.

TABLE 21

| Ia | Name | Reactant A-5 (method A) or A-7 (method B and C) | Reactant BB-4 (method A) or BB-3 (method B and C) | Method T [° C.] time [h] | $t_R$ [min] (LC/MS-method) | MS-data m/z [M + H]⁺ |
|---|---|---|---|---|---|---|
| Ia-1 | 3-[1-(2,6-Dimethyl-phenyl)-piperidin-4-yl]-1-(2-trifluoromethyl-benzyl)-3,4-dihydro-1H-quinazolin-2-one (Example 1) | A-5-1 | 2-Bromo-1,3-dimethyl benzene | A 110 24 | 1.14 (I) | 494.14 |
| Ia-2 | 3-[1-(2,6-Difluoro-phenyl)-piperidin-4-yl]-1-(2-trifluoromethyl-benzyl)-3,4-dihydro-1H-quinazolin-2-one (Example 2) | A-5-1 | 2,6-Difluoro bromobenzene | A 100 24 | 1.11 (I) | 501.95 |
| Ia-3 | 3-[1-(2,6-Dimethyl-phenyl)-piperidin-4-yl]-8-methoxy-1-(2-trifluoromethyl-benzyl)-3,4-dihydro-1H-quinazolin-2-one (Example 3) | A-5-2 | 2-Bromo-1,3-dimethyl benzene | A 100 24 | 1.14 (I) | 523.99 |
| Ia-4 | 8-Methoxy-3-[1-(2-methoxy-phenyl)-piperidin-4-yl]-1-(2-trifluoromethyl-benzyl)-3,4-dihydro-1H-quinazolin-2-one (Example 4) | A-5-2 | 2-Bromoanisole | A 100 18 | 0.83 (I) | 525.96 |
| Ia-5 | 3-[1-(2-Fluoro-6-methoxy-phenyl)-piperidin-4-yl]-8-methoxy-1-(2-trifluoromethyl-benzyl)-3,4-dihydro-1H-quinazolin-2-one (Example 5) | A-5-2 | 2-Bromo-3-fluoroanisole | A 100 24 | 1.02 (I) | 544.12 |
| Ia-6 | 3-[1-(2-Methoxy-phenyl)-piperidin-4-yl]-1-(2-trifluoromethyl-benzyl)-3,4-dihydro-1H-quinazolin-2-one (Example 6) | A-5-1 | 2-Bromoanisole | A 100 18 | 0.84 (I) | 495.93 |
| Ia-7 | 3-[1-(2-Fluoro-6-methoxy-phenyl)-piperidin-4-yl]-1-(2-trifluoromethyl-benzyl)-3,4-dihydro-1H-quinazolin-2-one (Example 7) | A-5-1 | 2-Bromo-3-fluoroanisole | A 100 24 | 1.02 (I) | 513.85 |
| Ia-8 | 3-[(R)-1-(2,6-Difluoro-phenyl)-pyrrolidin-3-yl]-8-methoxy-1-(2-trifluoromethyl-benzyl)-3,4-dihydro-1H-quinazolin-2-one (Example 8) | A-5-3 | 2,6-Difluoro bromobenzene | A 100 24 | 1.09 (I) | 517.93 |
| Ia-9 | 3-[(R)-1-(2,6-Dimethyl-phenyl)-pyrrolidin-3-yl]-8-methoxy-1-(2-trifluoromethyl-benzyl)-3,4-dihydro-1H-quinazolin-2-one (Example 9) | A-5-3 | 2-Bromo-1,3-dimethyl benzene | A 100 24 | 0.94 (I) | 509.96 |
| Ia-10 | 8-Methoxy-3-[(R)-1-(2-methoxy-phenyl)-pyrrolidin-3-yl]-1-(2-trifluoromethyl-benzyl)-3,4-dihydro-1H-quinazolin-2-one (Example 10) | A-5-3 | 2-Bromoanisole | A 100 24 | 0.88 (I) | 512.09 |
| Ia-11 | 3-[(R)-1-(2-Fluoro-6-methoxy-phenyl)-pyrrolidin-3-yl]-8- | A-5-3 | 2-Bromo-3-fluoroanisole | A 100 | 0.91 (I) | 529.79 |

TABLE 21-continued

| Ia | Name | Reactant A-5 (method A) or A-7 (method B and C) | Reactant BB-4 (method A) or BB-3 (method B and C) | Method T [° C.] time [h] | $t_R$ [min] (LC/MS-method) | MS-data m/z [M + H]+ |
|---|---|---|---|---|---|---|
|  | methoxy-1-(2-trifluoromethyl-benzyl)-3,4-dihydro-1H-quinazolin-2-one (Example 11) |  |  | 24 |  |  |
| Ia-12 | 3-[1-(2-Fluoro-6-methyl-phenyl)-piperidin-4-yl]-1-(2-trifluoromethyl-benzyl)-3,4-dihydro-1H-quinazolin-2-one (Example 13) | A-5-1 | 2-Bromo-3-fluorotoluene | A 100 18 | 1.13 (I) | 498.03 |
| Ia-13 | 3-[(S)-1-(2,6-Dimethyl-phenyl)-pyrrolidin-3-yl]-1-(2-trifluoromethyl-benzyl)-3,4-dihydro-1H-quinazolin-2-one (Example 14) | A-5-4 | 2-Bromo-1,3-dimethyl benzene | A 100 24 | 0.94 (I) | 479.99 |
| Ia-14 | 3-[(S)-1-(2,6-Difluoro-phenyl)-pyrrolidin-3-yl]-1-(2-trifluoromethyl-benzyl)-3,4-dihydro-1H-quinazolin-2-one (Example 15) | A-5-4 | 2,6-Difluoro bromobenzene | A 100 24 | 1.09 (I) | 487.93 |
| Ia-15 | 3-[(S)-1-(2-Methoxy-phenyl)-pyrrolidin-3-yl]-1-(2-trifluoromethyl-benzyl)-3,4-dihydro-1H-quinazolin-2-one (Example 16) | A-5-4 | 2-Bromoanisole | A 100 24 | 0.88 (I) | 481.99 |
| Ia-16 | 3-[(S)-1-(2-Fluoro-6-methoxy-phenyl)-pyrrolidin-3-yl]-1-(2-trifluoromethyl-benzyl)-3,4-dihydro-1H-quinazolin-2-one (Example 17) | A-5-4 | 2-Bromo-3-fluoroanisole | A 100 24 | 0.92 (I) | 500.08 |
| Ia-17 | 3-[(R)-1-(2,6-Dimethyl-phenyl)-pyrrolidin-3-yl]-1-(2-trifluoromethyl-benzyl)-3,4-dihydro-1H-quinazolin-2-one (Example 18) | A-5-5 | 2-Bromo-1,3-dimethyl benzene | A 100 24 | 0.93 (I) | 480.00 |
| Ia-18 | 3-[(R)-1-(2,6-Difluoro-phenyl)-pyrrolidin-3-yl]-1-(2-trifluoromethyl-benzyl)-3,4-dihydro-1H-quinazolin-2-one (Example 19) | A-5-5 | 2,6-Difluoro bromobenzene | A 100 24 | 1.09 (I) | 488.06 |
| Ia-19 | 3-[(R)-1-(2-Methoxy-phenyl)-pyrrolidin-3-yl]-1-(2-trifluoromethyl-benzyl)-3,4-dihydro-1H-quinazolin-2-one (Example 20) | A-5-5 | 2-Bromoanisole | A 100 24 | 0.87 (I) | 481.85 |
| Ia-20 | 3-[(R)-1-(2-Fluoro-6-methoxy-phenyl)-pyrrolidin-3-yl]-1-(2-trifluoromethyl-benzyl)-3,4-dihydro-1H-quinazolin-2-one (Example 21) | A-5-5 | 2-Bromo-3-fluoroanisole | A 100 24 | 0.92 (I) | 500.09 |
| Ia-21 | 8-Methoxy-3-[(R)-1-(2-methoxy-6-methyl-phenyl)-pyrrolidin-3-yl]-1-(2-trifluoromethyl-benzyl)-3,4-dihydro-1H-quinazolin-2-one (Example 22) | A-5-3 | 2-Bromo-1-methoxy-3-methylbenzene | A 100 24 | 0.89 (I) | 526.10 |
| Ia-22 | 3-[1-(2-Methoxy-6-methyl-phenyl)-piperidin-4-yl]-1-(2-trifluoromethyl-benzyl)-3,4-dihydro-1H-quinazolin-2-one (Example 23) | A-5-1 | 2-Bromo-1-methoxy-3-methylbenzene | A 100 24 | 0.99 (I) | 510.12 |
| Ia-23 | 3-[(R)-1-(2,6-Dimethoxy-phenyl)-pyrrolidin-3-yl]-8-methoxy-1-(2-trifluoromethyl-benzyl)-3,4-dihydro-1H-quinazolin-2-one (Example 24) | A-5-3 | 2-Bromo-1,3-dimethoxy benzene | A 100 24 | 0.88 (I) | 542.12 |
| Ia-24 | 8-Methoxy-3-[1-(2-methoxy-6-methyl-phenyl)-piperidin-4-yl]-1-(2-trifluoromethyl-benzyl)-3,4-dihydro-1H-quinazolin-2-one (Example 25) | A-5-2 | 2-Bromo-1-methoxy-3-methylbenzene | A 100 24 | 1.00 (I) | 540.03 |
| Ia-25 | 3-[(R)-1-(2-Fluoro-6-methyl-phenyl)-pyrrolidin-3-yl]-1-(2- | A-5-5 | 2-Bromo-3-fluorotoluene | A 100 | 1.05 (1) | 484.15 |

TABLE 21-continued

| Ia | Name | Reactant A-5 (method A) or A-7 (method B and C) | Reactant BB-4 (method A) or BB-3 (method B and C) | Method T [° C.] time [h] | $t_R$ [min] (LC/MS-method) | MS-data m/z $[M + H]^+$ |
|---|---|---|---|---|---|---|
| | trifluoromethyl-benzyl)-3,4-dihydro-1H-quinazolin-2-one (Example 26) | | | 24 | | |
| Ia-26 | 3-[(R)-1-(2-Methoxy-6-methyl-phenyl)-pyrrolidin-3-yl]-1-(2-trifluoromethyl-benzyl)-3,4-dihydro-1H-quinazolin-2-one (Example 27) | A-5-5 | 2-Bromo-1-methoxy-3-methylbenzene | A 100 24 | 0.88 (I) | 496.24 |
| Ia-27 | 3-(2',4'-Dimethyl-3,4,5,6-tetrahydro-2H-[1,3']bipyridinyl-4-yl)-1-(2-trifluoromethyl-benzyl)-3,4-dihydro-1H-quinazolin-2-one (Example 28) | A-5-1 | 3-Bromo-2,4-dimethylpyridine | A 100 24 | 0.82 (1) | 495.15 |
| Ia-28 | 3-(2'-Methoxy-4'-methyl-3,4,5,6-tetrahydro-2H-[1,3']bipyridinyl-4-yl)-1-(2-trifluoromethyl-benzyl)-3,4-dihydro-1H-quinazolin-2-one (Example 29) | A-5-1 | 3-Bromo-2-methoxy-4-methylpyridine | A 100 24 | 1.10 (l) | 511.17 |
| Ia-29 | 3-(2'-Fluoro-4'-methyl-3,4,5,6-tetrahydro-2H-[1,3']bipyridinyl-4-yl)-1-(2-trifluoromethyl-benzyl)-3,4-dihydro-1H-quinazolin-2-one (Example 30) | A-5-1 | 3-Bromo-2-fluoro-4-methyl pyridine | A 100 24 | 1.08 (I) | 499.16 |
| Ia-30 | 3-[(R)-1-(2-Methoxy-4-methyl-pyridin-3-yl)-pyrrolidin-3-yl]-1-(2-trifluoromethyl-benzyl)-3,4-dihydro-1H-quinazolin-2-one (Example 31) | A-5-5 | 3-Bromo-2-methoxy-4-methylpyridine | A 100 24 | 0.94 (I) | 497.06 |
| Ia-31 | 3-[(R)-1-(2,4-Dimethyl-pyridin-3-yl)-pyrrolidin-3-yl]-1-(2-trifluoromethyl-benzyl)-3,4-dihydro-1H-quinazolin-2-one (Example 32) | A-5-5 | 3-Bromo-2,4-dimethylpyridine | A 100 24 | 0.81 (I) | 481.17 |
| Ia-32 | 3-[(R)-1-(2-Fluoro-4-methyl-pyridin-3-yl)-pyrrolidin-3-yl]-1-(2-trifluoromethyl-benzyl)-3,4-dihydro-1H-quinazolin-2-one (Example 33) | A-5-5 | 3-Bromo-2-fluoro-4-methylpyridine | A 100 24 | 1.06 (I) | 485.15 |
| Ia-33 | 3-[(R)-1-(2,6-Dimethyl-phenyl)-pyrrolidin-3-yl]-1-(2-methoxy-benzyl)-3,4-dihydro-1H-quinazolin-2-one (Example 34) | A-5-6 | 2-Bromo-1,3-dimethyl benzene | A 100 24 | 0.90 (I) | 442.26 |
| Ia-34 | 3-[(R)-1-(2-Fluoro-6-methyl-phenyl)-pyrrolidin-3-yl]-1-(2-methoxy-benzyl)-3,4-dihydro-1H-quinazolin-2-one (Example 35) | A-5-6 | 2-Bromo-3-fluorotoluene | A 100 24 | 0.99 (I) | 446.19 |
| Ia-35 | 3-[1-(2,6-Dimethyl-phenyl)-piperidin-4-yl]-1-(2-methoxy-benzyl)-3,4-dihydro-1H-quinazolin-2-one (Example 36) | A-5-7 | 2-Bromo-1,3-dimethyl benzene | A 100 24 | 1.10 (I) | 456.23 |
| Ia-36 | 3-[1-(2-Fluoro-6-methyl-phenyl)-piperidin-4-yl]-1-(2-methoxy-benzyl)-3,4-dihydro-1H-quinazolin-2-one (Example 37) | A-5-7 | 2-Bromo-3-fluorotoluene | A 100 24 | 1.10 (I) | 460.17 |
| Ia-37 | 3-Fluoro-2-{4-[2-oxo-1-(3-trifluoromethyl-pyrazin-2-ylmethyl)-1,4-dihydro-2H-quinazolin-3-yl]-piperidin-1-yl}-benzonitrile (Example 38) | A-7-1 | BB-3-1 | B RT 96 | 1.02 (I) | 511.70 |
| Ia-38 | 3-Fluoro-2-{4-[1-(3-methoxy-pyrazin-2-ylmethyl)-2-oxo-1,4-dihydro-2H-quinazolin-3-yl]-piperidin-1-yl}-benzonitrile (Example 39) | A-7-1 | 2-(Bromomethyl)-3-methoxy pyrazine | B RT 24 | 0.99 (I) | 473.12 |

TABLE 21-continued

| Ia | Name | Reactant A-5 (method A) or A-7 (method B and C) | Reactant BB-4 (method A) or BB-3 (method B and C) | Method T [° C.] time [h] | $t_R$ [min] (LC/MS-method) | MS-data m/z $[M + H]^+$ |
|---|---|---|---|---|---|---|
| Ia-39 | 3-[1-(2-Fluoro-6-methyl-phenyl)-piperidin-4-yl]-1-[1-(2-methoxy-phenyl)-ethyl]-3,4-dihydro-1H-quinazolin-2-one (Example 40) | A-7-2 | 1-(1-Chloroethyl)-2-methoxy benzene | B 70 72 | 1.10 (I) | 474.23 |
| Ia-40 | 3-[1-(2-Fluoro-6-methyl-phenyl)-piperidin-4-yl]-1-(3-trifluoromethyl-pyrazin-2-ylmethyl)-3,4-dihydro-1H-quinazolin-2-one (Example 42) | A-7-2 | BB-3-1 | B RT 24 | 1.07 (I) | 500.11 |
| Ia-41 | 3-[1-(2-Fluoro-6-methyl-phenyl)-piperidin-4-yl]-1-(3-methoxy-pyrazin-2-ylmethyl)-3,4-dihydro-1H-quinazolin-2-one (Example 43) | A-7-2 | 2-(Bromomethyl)-3-methoxy pyrazine | B RT 24 | 1.04 (I) | 462.12 |
| Ia-42 | 3-[1-(2-Fluoro-6-methyl-phenyl)-piperidin-4-yl]-1-(2-hydroxy-benzyl)-3,4-dihydro-1H-quinazolin-2-one | A-7-2 | 2-(Chloromethyl) phenyl acetate | B RT 24 | 1.04 (I) | 446.14 |
| Ia-43 | 3-[1-(2-Fluoro-6-methyl-phenyl)-piperidin-4-yl]-1-[1-(2-trifluoromethyl-phenyl)-ethyl]-3,4-dihydro-1H-quinazolin-2-one (Example 45) | A-7-2 | 1-(2-(trifluoromethyl) phenyl)ethan-1-ol | C 110 2 | 1.12 (I) | 512.12 |
| Ia-44 | {3-[1-(2-Fluoro-6-methyl-phenyl)-piperidin-4-yl]-2-oxo-3,4-dihydro-2H-quinazolin-1-yl}-(2-methoxy-phenyl)-acetic acid methyl ester (Example 49) | A-7-2 | Methyl 2-bromo-2-(2-methoxy phenyl)acetate | B 50 24 | 1.07 (l) | 518.14 |
| Ia-45 | 1-(2-Cyclopropyl-benzyl)-3-[1-(2-fluoro-6-methyl-phenyl)-piperidin-4-yl]-3,4-dihydro-1H-quinazolin-2-one (Example 56) | A-7-2 | (2-Cyclopropyl phenyl)methanol | C 110 2 | 1.13 (I) | 470.15 |
| Ia-46 | 3-[1-(2-Fluoro-6-methyl-phenyl)-piperidin-4-yl]-1-(2-isopropyl-benzyl)-3,4-dihydro-1H-quinazolin-2-one (Example 57) | A-7-2 | 1-(Bromomethyl)-2-isopropyl benzene | B RT 24 | 1.13 (I) | 472.17 |
| Ia-47 | 3-[1-(2-Fluoro-6-methyl-phenylpiperidin-4-yl]-1-(3-isopropoxy-pyrazin-2-ylmethyl)-3,4-dihydro-1H-quinazolin-2-one (Example 59) | A-7-2 | BB-3-2 | C 110 24 | 1.09 (I) | 490.15 |
| Ia-48 | 3-[1-(2-Fluoro-6-methyl-phenyl)-piperidin-4-yl]-1-(3-isopropoxy-pyridin-2-ylmethyl)-3,4-dihydro-1H-quinazolin-2-one (Example 60) | A-7-2 | BB-3-3 | C 110 3 | 0.94 (I) | 489.16 |
| Ia-49 | 3-[1-(2-Fluoro-6-methyl-phenyl)-piperidin-4-yl]-1-(4-isopropyl-pyridin-3-ylmethyl)-3,4-dihydro-1H-quinazolin-2-one (Example 61) | A-7-2 | BB-3-4 | C 110 3.5 | 0.88 (I) | 473.19 |
| Ia-50 | 3-[1-(2-Fluoro-6-methyl-phenylpiperidin-4-yl]-1-(3-isopropyl-pyrazin-2-ylmethyl)-3,4-dihydro-1H-quinazolin-2-one (Example 62) | A-7-2 | BB-3-5 | C 110 1.5 | 1.07 (I) | 474.22 |
| Ia-51 | 3-[1-(2-Fluoro-6-methyl-phenyl)-piperidin-4-yl]-1-(4- | A-7-2 | BB-3-6 | C 110 | 1.13 (I) | 474.21 |

TABLE 21-continued

| Ia | Name | Reactant A-5 (method A) or A-7 (method B and C) | Reactant BB-4 (method A) or BB-3 (method B and C) | Method T [° C.] time [h] | $t_R$ [min] (LC/MS-method) | MS-data m/z $[M + H]^+$ |
|---|---|---|---|---|---|---|
| | isopropyl-pyrimidin-5-ylmethyl)-3,4-dihydro-1H-quinazolin-2-one (Example 63) | | | 2 | | |
| Ia-52 | 3-[1-(2-Fluoro-6-methyl-phenyl)-piperidin-4-yl]-1-(2-trifluoromethyl-pyridin-3-ylmethyl)-3,4-dihydro-1H-quinazolin-2-one (Example 65) | A-7-2 | (2-(Trifluoromethyl) pyridin-3-yl) methanol | C 110 24 | 1.09 (I) | 499.12 |
| Ia-53 | 3-[1-(2-Fluoro-6-methyl-phenyl)-piperidin-4-yl]-1-(4-trifluoromethyl-pyridin-3-ylmethyl)-3,4-dihydro-1H-quinazolin-2-one (Example 67) | A-7-2 | (4-Trifluoromethyl-pyridin-3-yl)-methanol | C 110 24 | 1.12 (I) | 499.10 |
| Ia-54 | 1-(2-Cyclopropoxy-benzyl)-3-[1-(2-fluoro-6-methyl-phenyl)-piperidin-4-yl]-3,4-dihydro-1H-quinazolin-2-one (Example 68) | A-7-2 | 1-(Bromomethyl)-2-cyclopropyloxy benzene | B RT 24 | 1.12 (1) | 486.14 |
| Ia-55 | 3-[1-(2-Fluoro-6-methyl-phenyl)-piperidin-4-yl]-1-(3-trifluoromethyl-pyridin-2-ylmethyl)-3,4-dihydro-1H-quinazolin-2-one (Example 69) | A-7-2 | 2-(Chloromethyl)-3-(trifluoromethyl) pyridine | B RT 48 | 1.08 (I) | 499.07 |
| Ia-56 | 3-[1-(2-Fluoro-6-methyl-phenyl)-piperidin-4-yl]-1-(2-trifluoromethoxy-benzyl)-3,4-dihydro-1H-quinazolin-2-one (Example 74) | A-7-2 | 2-(Trifluoro methoxy) benzyl bromide | B RT 3 | 1.30 (II) | 513.99 |
| Ia-57 | 1-(2-Chloro-benzyl)-3-[1-(2-fluoro-6-methyl-phenyl)-piperidin-4-yl]-3,4-dihydro-1H-quinazolin-2-one (Example 75) | A-7-2 | 2-Chloro-benzyl bromide | B RT 17 | 1.28 (II) | 464.10 |
| Ia-58 | 3-[1-(2-Fluoro-6-trifluoromethyl-phenyl)-piperidin-4-yl]-1-(2-trifluoromethyl-benzyl)-3,4-dihydro-1H-quinazolin-2-one (Example 76) | A-5-1 | 2-Bromo-3-fluorobenzo trifluoride | A 100 27 | 1.31 (II) | 552.08 |
| Ia-59 | 3-[1-(2-Fluoro-6-trifluoromethoxy-phenyl)-piperidin-4-yl]-1-(2-trifluoromethyl-benzyl)-3,4-dihydro-1H-quinazolin-2-one (Example 78) | A-5-1 | 2-Bromo-1-fluoro-3-(trifluoro methoxy)benzene | A 100 25 | 1.31 (II) | 568.04 |
| Ia-60 | 3-[1-(2-Chloro-6-methyl-phenyl)-piperidin-4-yl]-1-(2-trifluoromethyl-benzyl)-3,4-dihydro-1H-quinazolin-2-one (Example 79) | A-5-1 | 2-Bromo-3-chlorotoluene | A 100 24 | 1.32 (II) | 513.96 |
| Ia-61 | 3-[1-(2-Fluoro-6-methyl-phenyl)-piperidin-4-yl]-1-(4-isopropoxy-pyridazin-3-ylmethyl)-3,4-dihydro-1H-quinazolin-2-one (Example 80) | A-7-2 | BB-3-7 | C 110 23 | 0.96 (II) | 490.13 |
| Ia-62 | 1-(2-Bromo-6-trifluoromethyl-benzyl)-3-[1-(2-fluoro-6-methyl-phenyl)-piperidin-4-yl]-3,4-dihydro-1H-quinazolin-2-one | A-7-2 | 2-Bromo-6-(trifluoromethyl) benzyl bromide | B RT 18 | 1.31 (II) | 575.93 |
| Ia-63 | 3-[1-(2-Fluoro-6-methyl-phenyl)-piperidin-4-yl]-1-(2-methyl-4-trifluoromethyl-thiazol-5-ylmethyl)-3,4-dihydro-1H-quinazolin-2-one (Example 83) | A-7-2 | 5-(Bromomethyl)-2-methyl-4-(trifluoromethyl)-1,3-thiazole | B RT 4 | 1.24 (II) | 519.25 |

Synthesis of Compounds of Formula Ib

Method I (multistep)
Step A: Aromatic Nucleophilic Substitution

To a soln. of A-5 (1 eq) and BB-4 (1 to 2 eq) in DMSO (3 mL/mmol) was added CsF (2 eq). The rxn mixture was heated at a given temperature for a given time (see Table 22) and was partitioned between EtOAc and water. The org. phase was washed with water (3×) and brine (1×), dried over $MgSO_4$ and concentrated in vacuo. The crude was purified by CC using Hept/EtOAc.

TABLE 22

| Ib-A | Name | Reactant A-5 | Reactant BB-4 | T [° C.] time [h] | $t_R$ [min] (LC/MS method) | MS-data m/z $[M+H]^+$ |
|---|---|---|---|---|---|---|
| Ib-1A | 3-Cyclopropyl-1-methyl-5-{4-[2-oxo-1-(2-trifluoromethyl-benzyl)-1,4-dihydro-2H-quinazolin-3-yl]-piperidin-1-yl}1H-pyrazole-4-carbaldehyde | A-5-1 | 5-Chloro-3-cyclopropyl-1-methyl-1H-pyrazole-4-carbaldehyde | 100 48 | 1.03 (I) | 537.98 |
| Ib-3A | 1,3-Dimethyl-5-{4-[2-oxo-1-(2-trifluoromethyl-benzyl)-1,4-dihydro-2H-quinazolin-3-yl]-piperidin-1-yl}-1H-pyrazole-4-carbaldehyde | A-5-1 | 5-Chloro-1,3-dimethyl-1H-pyrazole-4-carbaldehyde | 150 2 (under microwave irradiation) | 1.14 (I) | 512.06 |

Step B: Decarbonylation

To a soln. of Ib-A (1 eq) in MeOH (8 mL/mmol) was added toluene-4-sulfonic acid monohydrate (0.2 eq) and the rxn mixture was heated at 120° C. under microwave condition for a given time (see Table 23). It was concentrated in vacuo and partitioned between EtOAc and a sat. aq. soln. of $NaHCO_3$. The org. phase was washed with brine, dried over $MgSO_4$ and concentrated in vacuo. The crude was purified by CC using Hept/EtOAc.

TABLE 23

| Ib-B | Name | Reactant Ib-A | time [h] | $t_R$ [min] (LC/MS-method) | MS-data m/z [M + H]$^+$ |
|---|---|---|---|---|---|
| Ib-1B | 3-[1-(5-Cyclopropyl-2-methyl-2H-pyrazol-3-yl)-piperidin-4-yl]-1-(2-trifluoromethyl-benzyl)-3,4-dihydro-1H-quinazolin-2-one | Ib-1A | 0.35 | 0.94 (I) | 509.98 |
| Ib-3B | 3-[1-(2,5-Dimethyl-2H-pyrazol-3-yl)-piperidin-4-yl]-1-(2-trifluoromethyl-benzyl)-3,4-dihydro-1H-quinazolin-2-one | Ib-3A | 1.5 | 0.98 (II) | 484.02 |

Step C: Chlorination

To a soln. of Ib-B (1 eq) in THF (4.5 mL/mmol) was added NCS (1.4 eq) and the rxn mixture was stirred at RT for a given time (see Table 24). It was partitioned between EtOAc and water and the org. phase was washed with brine, dried over $MgSO_4$ and concentrated in vacuo. The crude was purified by CC using Hept/EtOAc.

TABLE 24

| Ib | Name | Reactant Ib-B | time [h] | $t_R$ [min] (LC/MS method) | MS-data m/z [M + H]$^+$ |
|---|---|---|---|---|---|
| Ib-1 | 3-[1-(4-Chloro-5-cyclopropyl-2-methyl-2H-pyrazol-3-yl)-piperidin-4-yl]-1-(2-trifluoromethyl-benzyl)-3,4-dihydro-1H-quinazolin-2-one (Example 12) | Ib-1B | 0.75 | 1.10 (I) | 544.09 |
| Ib-3 | 3-[1-(4-Chloro-2,5-dimethyl-2H-pyrazol-3-yl)-piperidin-4-yl]-1-(2-trifluoromethyl-benzyl)-3,4-dihydro-1H-quinazolin-2-one (Example 73) | Ib-3B | 0.5 | 1.22 (II) | 518.06 |

Method II (SN$_{Ar}$ Alone)

To a soln. of A-5 (1 eq) and BB-4 (2 eq) in DMSO (4 mL/mmol) was added CsF (2 eq). The rxn mixture was heated at 130° C. under microwave irradiation for a given time (see Table 25) and was partitioned between EtOAc and water. The org. phase was washed with water (3×) and brine (1×), dried over MgSO$_4$ and concentrated in vacuo. The crude was purified by CC using Hept/EtOAc.

TABLE 25

| Ib | Name | Reactant A-5 | Reactant BB-4 | time [h] | $t_R$ [min] (LC/MS method) | MS-data m/z [M+H]$^+$ |
|---|---|---|---|---|---|---|
| Ib-2 | 1,3-Dimethyl-5-{4-[2-oxo-1-(2-trifluoromethyl-benzyl)-1,4-dihydro-2H-quinazolin-3-yl]-piperidin-1-yl}-1H-pyrazole-4-carbonitrile (Example 72) | A-5-1 | 5-Chloro-1,3-dimethyl-1H-pyrazole-4-carbonitrile | 2.5 | 1.15 (II) | 509.07 |

Synthesis of Compounds of Formula Ic

Method A (K$_2$CO$_3$/DMF)

To a stirred soln. of compounds of formula Ia (1 eq) in DMF (6 mL/mmol) was added K$_2$CO$_3$ (2 eq) followed by the appropriate halide (1.5 eq). The rxn mixture was stirred at a given temperature for a given time (see Table 26). It was partitioned between EtOAc and H$_2$O. The org. phase was washed with water (2×) and brine (1×), dried over MgSO$_4$ and concentrated in vacuo. The crude was purified by CC using Hept/EtOAc and/or DCM/MeOH.

Method B (NaH/THF)

To a soln. of compounds of formula Ia (1 eq) in anh. THF (3 mL/mmol) was added NaH (5 eq, as a 60% dispersion in mineral oil) at 0° C. The rxn mixture was stirred for 10 min and a soln. of the appropriate halide (4 eq) in anh. THF (3 mL/mmol) was added at 0° C. (when using a halide as HCl salt TEA (4 eq) was additionally added). The rxn mixture was stirred for 10 min at 0° C. and for a given time at a given temperature (see Table 26). It was quenched with a 0.1M aq. soln. of HCl and extracted with EtOAc (3×). The combined org. phases were washed with brine, dried over MgSO$_4$ and concentrated in vacuo. The crude was purified by CC using Hept/EtOAc and/or DCM/MeOH.

Method C (Mitsunobu)

To a soln. of intermediate Ia (1 eq) and of the appropriate alcohol (1.8 eq) in toluene (7 mL/mmol) was added a 1M soln. of (tributylphosphoranylidene)acetonitrile in toluene (2 eq) under argon. The rxn mixture was heated to a given temperature and stirred for a given time (see Table 26). It was quenched with water and extracted with EtOAc (3×). The combined org. phases were washed with brine, dried over MgSO$_4$ and concentrated in vacuo. The crude was purified by CC using Hept/EtOAc and/or DCM/MeOH.

Method D (Saponification)

To a soln. of carboxylic ester Ic (1 eq) in THF (15 mL/mmol) was added a 2M aq. soln. of NaOH (10 eq) and the rxn mixture was stirred at a given temperature for a given time (see Table 26). It was acidified with a 1M aq. soln. of HCl until pH~3-4 and extracted with EtOAc (3×). The combined org. phases were washed with brine, dried over MgSO$_4$ and concentrated in vacuo.

Method E (Hydrogenation)

Intermediate Ia (1 eq) was dissolved in EtOAc (19 mL/mmol) and Et$_3$N (3 eq) was added at RT. The flask was evacuated three times and refilled with nitrogen. Wet Pd/C (0.1 eq) was added and the flask was evacuated three times and refilled with deuterium. The suspension was stirred under an atmospheric pressure of deuterium for a given time (see Table 26) and filtered over a pad of Celite. The cake was washed with EtOAc and the filtrate was concentrated in vacuo. The crude was purified by CC using Hept/EtOAc.

TABLE 26

| Ic | Name | Reactant Ia | Reactant halide or alcohol | Method T [° C.] time [h] | $t_R$ [min] (LC/MS method) | MS-data m/z [M+H]$^+$ |
|---|---|---|---|---|---|---|
| Ic-1 | 3-[1-(2-Fluoro-6-methyl-phenyl)-piperidin-4-yl]-1-(2-isopropoxy-benzyl)-3,4-dihydro-1H-quinazolin-2-one (Example 44) | Ia-42 | 2-Bromopropane | A 70 24 | 1.13 (I) | 488.14 |
| Ic-2 | 1-(2-Ethoxy-benzyl)-3-[1-(2-fluoro-6-methyl-phenyl)-piperidin-4-yl]-3,4-dihydro-1H-quinazolin-2-one (Example 46) | Ia-42 | Bromoethane | A 50 24 | 1.11 (I) | 474.16 |
| Ic-3 | 1-[2-(2-Dimethylamino-ethoxy)-benzyl]-3-[1-(2-fluoro-6-methyl-phenyl)-piperidin-4-yl]-3,4-dihydro-1H-quinazolin-2-one (Example 47) | Ia-42 | 2-Chloro-N,N-dimethylethylamine hydrochloride | B 60 24 | 0.88 (I) | 517.13 |
| Ic-4 | Acetic acid 2-(2-{3-[1-(2-fluoro-6-methyl- | Ia-42 | 2-Bromoethyl acetate | B 60 24 | 1.09 (I) | 532.16 |

TABLE 26-continued

| Ic | Name | Reactant Ia | Reactant halide or alcohol | Method T [°C.] time [h] | $t_R$ [min] (LC/MS-method) | MS-data m/z $[M+H]^+$ |
|---|---|---|---|---|---|---|
| | phenyl)-piperidin-4-yl]-2-oxo-3,4-dihydro-2H-quinazolin-1-ylmethyl}-phenoxy)-ethyl ester (Example 48) | | | | | |
| Ic-5 | 3-[1-(2-Fluoro-6-methyl-phenyl)-piperidin-4-yl]-1-[2-(2-hydroxy-ethoxy)-benzyl]-3,4-dihydro-1H-quinazolin-2-one (Example 50) | Ic-4 | — | D 50 18 | 1.03 (I) | 490.12 |
| Ic-6 | 3-[1-(2-Fluoro-6-methyl-phenyl)-piperidin-4-yl]-1-[2-(oxetan-3-yloxy)-benzyl]-3,4-dihydro-1H-quinazolin-2-one (Example 51) | Ia-42 | 3-Bromooxetane | A 100 96 | 1.08 (I) | 502.15 |
| Ic-7 | 1-(2-Cyclobutoxy-benzyl)-3-[1-(2-fluoro-6-methyl-phenyl)-piperidin-4-yl]-3,4-dihydro-1H-quinazolin-2-one (Example 52) | Ia-42 | Cyclobutanol | C 110 1 | 1.14 (I) | 500.19 |
| Ic-8 | 3-[1-(2-Fluoro-6-methyl-phenyl)piperidin-4-yl]-1-[2-(tetrahydro-pyran-4-yloxy)-benzyl]-3,4-dihydro-1H-quinazolin-2-one (Example 53) | Ia-42 | Tetrahydro-4-pyranol | C 110 1 | 1.10(I) | 530.05 |
| Ic-9 | 1-(2-Cyclopropylmethoxy-benzyl)-3-[1-(2-fluoro-6-methyl-phenyl)-piperidin-4-yl]-3,4-dihydro-1H-quinazolin-2-one (Example 54) | Ia-42 | (Bromomethyl)cyclopropane | B RT 24 | 1.13 (I) | 500.11 |
| Ic-10 | (2-{3-[1-(2-Fluoro-6-methyl-phenyl)-piperidin-4-yl]-2-oxo-3,4-dihydro-2H-quinazolin-1-ylmethyl}-phenoxy)-acetonitrile (Example 55) | Ia-42 | Bromoacetonitrile | A RT 24 | 1.07 (I) | 485.16 |
| Ic-11 | 1-(6-trifluoromethyl[2-$^2$H]benzyl)-3-[1-(2-fluoro-6-methyl-phenyl)-piperidin-4-yl]-3,4-dihydro-1H-quinazolin-2-one (Example 82) | Ia-62 | — | E RT 2 | 1.29 (II) | 499.06 |

Synthesis of Intermediates of Formula B-1

A soln. of halide BB-5 (1 eq) and amine BB-6 (2.2 eq) in anh. EtOH was heated to 70° C. and stirred for 24 h at RT (see Table 27). The volatiles were evaporated and the residue was partitioned between a 10% aq. soln. of $Na_2CO_3$ and EtOAc. The aq. phase was extracted with EtOAc (2×) and the combined org. phases were washed with brine, dried over $MgSO_4$ and concentrated in vacuo. The crude was purified by CC using Hept/EtOAc.

TABLE 27

| B-1 | Name | Reactant BB-5 | Reactant BB-6 | $t_R$ [min] (LC/MS method) | MS-data m/z $[M + H]^+$ |
|---|---|---|---|---|---|
| B-1-1 | 3-(2-Trifluoromethyl-benzylamino)-pyridazine-4-carbonitrile | 3-Chloro pyridazine-4-carbonitrile | 2-(Trifluoromethyl) benzylamine | 0.84 (I) | 279.15 |

Synthesis of Intermediates of Formula B-2

A 2.4 M soln. of LiAlH$_4$ in THF (2.2 eq) was diluted with anh. THF (2 mL/mmol) and cooled to −60° C. A soln. of nitrile intermediate B-1 (1 eq) in anh. THF (2 mL/mmol) was added dropwise and the rxn mixture was stirred for 30 min at −60° C. (see Table 28). It was quenched with the successive addition of H$_2$O (0.06 mL/mmol), a 2M aq. soln. of NaOH (0.15 mL/mmol) and H$_2$O (0.18 mL/mmol). The suspension was stirred for 30 min at RT, filtered over a pad of celite and the filtrate was concentrated in vacuo. The crude was purified by prep. LC-MS using method 5.

TABLE 28

| B-2 | Name | Reactant B-1 | $t_R$ [min] (LC/MS method) | MS-data m/z $[M + H]^+$ |
|---|---|---|---|---|
| B-2-1 | (4-Aminomethyl-pyridazin-3-yl)-(2-trifluoromethyl-benzyl)-amine | B-1-1 | 0.49 (I) | 283.12 |

Synthesis of Intermediates of Formula B-3

To a soln. of amine intermediate B-2 (1 eq) and ketone BB-7 (1.4 eq) in THF (4 mL/mmol) were added AcOH (1.5 eq) followed by NaBH(OAc)$_3$ (1.5 eq) portionwise. The rxn mixture was stirred at RT for a given time (see Table 29). It was quenched with a sat. aq. soln. of NaHCO$_3$ and extracted with EtOAc (3×). The combined org. phases were washed with brine, dried over MgSO$_4$ and concentrated in vacuo. The crude was purified by CC using Hept/EtOAc/MeOH.

TABLE 29

| B-3 | Name | Reactant B-2 | Reactant BB-7 | time [h] | $t_R$ [min] (LC/MS method) | MS-data m/z $[M+H]^+$ |
|---|---|---|---|---|---|---|
| B-3-1 | (4-{[1-(2-Fluoro-6-methyl-phenyl)-piperidin-4-ylamino]-methyl}-pyridazin-3-yl)-(2-trifluoromethyl-benzyl)-amine | B-2-1 | BB-7-1 | 2.5 | 0.76 (I) | 474.21 |

Synthesis of Compounds of Formula Id

To a soln. of intermediate B-3 (1 eq) in MeCN (3.7 mL/mmol) was added CDI (2 eq) and the rxn mixture was stirred at a given temperature for a given time (see Table 30). The solvent was evaporated off and the residue was partitioned between EtOAc and water. The org. phase was washed with brine, dried over MgSO$_4$ and concentrated in vacuo. The crude was purified by CC using DCM/MeOH. When necessary an additional purification by prep. LC-MS using method 4 was performed.

TABLE 30

| Id | Name | Reactant | T [° C.] time [h] | $t_R$ [min] (LC/MS method) | MS-data m/z $[M + H]^+$ |
|---|---|---|---|---|---|
| Id-1 | 6-[1-(2-Fluoro-6-methyl-phenyl)-piperidin-4-yl]-8-(2-trifluoromethyl-benzyl)-5,8-dihydro-6H-pyrimido[4,5-c]pyridazin-7-one (Example 41) | B-3-1 | 80 72 | 1.04 (I) | 500.10 |

Synthesis of Intermediates of Formula C-1

To a suspension of carboxylic acid BB-8 (1 eq) in EtOH (1.85 mL/mmol) was added H$_2$SO$_4$ (0.07 mL/mmol) and the rxn mixture was heated to reflux and stirred for 18 h (see Table 31). It was quenched with a sat. aq. soln. of NaHCO$_3$ to reach pH~8 and extracted with EtOAc (3×). The combined org. phases were washed with brine, dried over MgSO$_4$ and concentrated in vacuo.

TABLE 31

| C-1 | Name | Reactant BB-8 | $t_R$ [min] (LC/MS method) | MS-data m/z $[M + H]^+$ |
|---|---|---|---|---|
| C-1-3 | 4-Amino-pyridazine-3-carboxylic acid ethyl ester | 4-Amino-pyridazine-3-carboxylic acid hydrochloride | 0.33 (I) | 168.08 |

Synthesis of Intermediates of Formula C-2

To a soln. of ester intermediate C-1 (1 eq) and CaCl$_2$ (0.3 eq) in EtOH (15 mL/mmol) was added over 10 min at −10° C. a suspension of NaBH$_4$ (2.5 eq) in EtOH (8 mL/mmol). The rxn mixture was allowed to warm to RT and stirred at that temperature for a given time (see Table 32). It was quenched with water at 0° C. and concentrated in vacuo. The solid was triturated in DCM/MeOH 8/2, filtered and the filtrate was concentrated in vacuo.

TABLE 32

| C-2 | Name | Reactant C-1 | time [h] | $t_R$ [min] (LC/MS method) | MS-data m/z $[M + H]^+$ |
|---|---|---|---|---|---|
| C-2-3 | (4-Amino-pyridazin-3-yl)-methanol | C-1-3 | 2.5 | 0.16 (I) | 126.19 |

Synthesis of Intermediates of Formula C-3

To a suspension of alcohol intermediate C-2 (1 eq) in anh. DCM was added at RT MnO$_2$ (9 eq) and the rxn mixture was stirred in a sealed vessel at a given temperature for a given time (see Table 33). It was filtered over a pad of celite and the filtrate was concentrated in vacuo.

TABLE 33

| C-3 | Name | Reactant C-2 | T [° C.] time [h] | $t_R$ [min] (LC/MS method) | MS-data m/z [M + H]$^+$ |
|---|---|---|---|---|---|
| C-3-3 | 4-Amino-pyridazine-3-carbaldehyde | C-2-3 | 70S and RT 12 | 0.30 (III) | 124.17 |

Synthesis of Intermediates of Formula C-4

Method A (NaBH$_4$/TFE)

A soln. of aldehyde C-3 (1 eq) and amine BB-9 (1 eq) in TFE (2 mL/mmol) was heated to 40° C. and stirred for 10 min. NaBH$_4$ (1.2 eq) was added portionwise at RT and the rxn mixture was stirred for a given time at a given temperature (see Table 34). It was filtered and the filtrate was concentrated in vacuo. The crude was purified by CC using Hept/EtOAc.

Method B (NaBH(OAc)$_3$/AcOH/THF)

To a soln. of aldehyde C-3 (1 eq) and amine BB-9 (1 eq) in THF (4 mL/mmol) were added AcOH (2 eq) and the rxn mixture was stirred for 20 min at RT. NaBH(OAc)$_3$ (4 eq) was added portionwise and the rxn mixture was stirred at RT for a given time (see Table 34). When necessary to reach the complete reduction of the intermediate imine, NaBH$_4$ (1.2 eq) can be added at 0° C. and the rxn mixture stirred at RT. It was quenched with a 1M aq. soln. of NaOH and extracted with EtOAc (3×). The combined org. phases were washed with brine, dried over MgSO$_4$ and concentrated in vacuo. The crude was purified by CC using Hept/EtOAc/MeOH.

TABLE 34

| C-4 | Name | Reactant C-3 | Reactant BB-9 | Method T [° C.] time [h] | $t_R$ [min] (LC/MS method) | MS-data m/z [M+H]$^+$ |
|---|---|---|---|---|---|---|
| C-4-1 | 3-{[1-(2-Fluoro-6-methyl-phenyl)-piperidin-4-ylamino]-methyl}-pyrazin-2-ylamine | 3-Amino-pyrazine-2-carbaldehyde | BB-9-1 | A 40 1 | 0.64 (I) | 316.20 |
| C-4-2 | 5-{[1-(2-Fluoro-6-methyl-phenyl)-piperidin-4-ylamino]-methyl}-pyrimidin-4-ylamine | 4-amino-pyrimidine-5-carboxaldehyde | BB-9-1 | B RT 24 | 0.54 (I) | 316.13 |
| C-4-3 | 3-{[1-(2-Fluoro-6-methyl-phenyl)-piperidin-4-ylamino]-methyl}-pyridazin-4-ylamine | C-3-3 | BB-9-1 | B RT 2 | 0.53 (I) | 316.12 |

Synthesis of Intermediates of Formula C-5

Method A (No Base)

To a soln. of intermediate C-4 (1 eq) in a given solvent (3.7 to 5 mL/mmol) was added CDI (1.2 eq) and the rxn mixture was stirred at a given temperature for a given time (see Table 35). The solvent was evaporated off and the residue was partitioned between DCM and water. The org. phase was washed with brine, dried over MgSO$_4$ and concentrated in vacuo. The crude was purified by CC using Hept/EtOAc/MeOH.

Method B (Additional NaH)

To a suspension of intermediate C-4 (1 eq) in anh. THF (7.3 mL/mmol) was added NaH (2.5 eq, as a 60% dispersion in mineral oil) at 0° C. After 30 min of stirring at 0° C., CDI (1.2 eq) was added and the rxn mixture was allowed to reach RT. It was heated to a given temperature and stirred for a given time (see Table 35). It was quenched with a sat. aq. soln. of NaHCO$_3$ and extracted with DCM (3×). The combined org. phases were washed with brine, dried over MgSO$_4$ and concentrated in vacuo. The crude was purified by CC using Hept/EtOAc/MeOH

TABLE 35

| C-5 | Name | Reactant C-4 | Method Solvent | T [° C.] time [h] | $t_R$ [min] (LC/MS method) | MS-data m/z [M+H]$^+$ |
|---|---|---|---|---|---|---|
| C-5-1 | 3-[1-(2-Fluoro-6-methyl-phenyl)-piperidin-4-yl]-3,4-dihydro-1H-pteridin-2-one | C-4-1 | A THF | 80 24 | 0.89 (I) | 342.14 |
| C-5-2 | 3-[1-(2-Fluoro-6-methyl-phenyl)-piperidin-4-yl]-3,4-dihydro-1H-pyrimido[4,5-d]pyrimidin-2-one | C-4-2 | B THF | 70 0.5 | 0.83 (I) | 342.09 |
| C-5-3 | 7-[1-(2-Fluoro-6-methyl-phenyl)-piperidin-4-yl]-7,8-dihydro-5H-pyrimido[5,4-c]pyridazin-6-one | C-4-3 | A MeCN | RT 24 | 0.72 (I) | 342.10 |

Synthesis of Compounds of Formula Ie

To a soln. of intermediate C-5 (1 eq) in anh. DMF (6 mL/mmol) was added K$_2$CO$_3$ (3 eq) at RT followed by BB-3 (1.4 to 1.5 eq) at 0° C. The rxn mixture was allowed to reach RT and stirred at a given temperature for a given time (see Table 36). It was quenched with a half sat. aq. soln. of NaHCO$_3$ and extracted with DCM or EtOAc (3×). The combined org. phases were washed with brine, dried over MgSO$_4$ and concentrated in vacuo. The crude was purified by CC using Hept/EtOAc. When necessary, an additional purification by prep. LC-MS using method 3 can be performed.

TABLE 36

| Ie | Name | Reactant C-5 | Reactant BB-3 | T [° C.] time [h] | $t_R$ [min] (LC/MS method) | MS-data m/z [M+H]$^+$ |
|---|---|---|---|---|---|---|
| Ie-1 | 3-[1-(2-Fluoro-6-methyl-phenyl)-piperidin- | C-5-1 | 2-(Trifluoromethyl)benzyl bromide | 45 24 | 1.10 (I) | 500.22 |

TABLE 36-continued

| Ie | Name | Reactant C-5 | Reactant BB-3 | T [° C.] time [h] | $t_R$ [min] (LC/MS method) | MS-data m/z $[M+H]^+$ |
|---|---|---|---|---|---|---|
| | 4-yl]-1-(2-trifluoromethyl-benzyl)-3,4-dihydro-1H-pteridin-2-one (Example 58) | | | | | |
| Ie-2 | 3-[1-(2-Fluoro-6-methyl-phenyl)-piperidin-4-yl]-1-(2-trifluoromethyl-benzyl)-3,4-dihydro-1H-pyrimido[4,5-d]pyrimidin-2-one (Example 64) | C-5-2 | 2-(Trifluoromethyl) benzyl bromide | 60 4 | 1.10 (I) | 500.16 |
| Ie-3 | 7-[1-(2-Fluoro-6-methyl-phenyl)-piperidin-4-yl]-5-(2-trifluoromethyl-benzyl)-7,8-dihydro-5H-pyrimido[5,4-c]pyridazin-6-one (Example 66) | C-5-3 | 2-(Trifluoromethyl) benzyl bromide | RT 24 | 1.04 (I) | 500.10 |

Synthesis of Intermediates of Formula D-1

A soln. of diamine BB-10 (1 eq) and ketone BB-7 (1.1 eq) in TFE (10 mL/mmol) was stirred for 10 min at RT and cooled to 0° C. NaBH$_4$ (1.5 eq) was added portionwise and the rxn mixture was stirred for a given time at a given temperature (see Table 37). It was quenched with a sat. aq. soln. of NaHCO$_3$ and extracted with EtOAc (3×). The combined org. phases were washed with brine, dried over MgSO$_4$ and concentrated in vacuo. The crude was purified by CC using Hept/EtOAc.

TABLE 37

| D-1 | Name | Reactant BB-10 | Reactant BB-7 | T [° C.] time [h] | $t_R$ [min] (LC/MS method) | MS-data m/z $[M+H]^+$ |
|---|---|---|---|---|---|---|
| D-1-1 | [1-(2-Amino-phenyl)-ethyl]-[1-(2-fluoro-6-methyl-phenyl)-piperidin-4-yl]-amine | 2-(1-Amino ethyl) aniline | BB-7-1 | 70 1 | 0.77 (II) | 328.15 |

Synthesis of Intermediates of Formula D-2

To a soln. of intermediate D-1 (1 eq) in MeCN (10 mL/mmol) was added CDI (1.2 eq) and the rxn mixture was stirred at RT for a given time (see Table 38). The solvent was evaporated off and the residue was partitioned between EtOAc and a 10% aq. soln. of citric acid. The org. phase was washed with brine, dried over MgSO$_4$ and concentrated in vacuo. The crude was purified by CC using Hept/EtOAc.

TABLE 38

| D-2 | Name | Reactant D-1 | time [h] | $t_R$ [min] (LC/MS method) | MS-data m/z $[M+H]^+$ |
|---|---|---|---|---|---|
| D-2-1 | 3-[1-(2-Fluoro-6-methyl-phenyl)-piperidin-4-yl]-4-methyl-3,4-dihydro-1H-quinazolin-2-one | D-1-1 | 0.5 | 1.10 (II) | 354.21 |

Synthesis of Compounds of Formula If

To a suspension of intermediate D-2 (1 eq) in anh. THF (10 mL/mmol) was added NaH (5 eq, as a 60% dispersion in mineral oil) at 0° C. The rxn mixture was stirred for 10 min and BB-3 (1.5 eq) was added at 0° C. When necessary in terms of solubility, anh. DMF (0.1 to 2 mL/mmol) could be added. The rxn mixture was stirred at a given temperature for a given time (see Table 39), quenched with water at 0° C. and extracted with EtOAc (3×). The combined org. phases were washed with brine, dried over MgSO$_4$ and concentrated in vacuo. The crude was purified by CC using Hept/EtOAc or DCM/MeOH. When necessary an additional purification by prep. LC-MS using method 3 was performed.

TABLE 39

| If | Name | Reactant D-2 | Reactant BB-3 | $t_R$ [min] time [h] | T [° C.] | MS-data m/z (LC/MS method)$[M+H]^+$ |
|---|---|---|---|---|---|---|
| If-1 | 3-[1-(2-Fluoro-6-methyl-phenyl)-piperidin-4-yl]-4-methyl-1-(2-trifluoromethyl-benzyl)-3,4-dihydro-1H-quinazolin-2-one (Example 70) | D-2-1 | 2-(Trifluoromethyl) benzyl bromide | RT 18 then 60 7 | | 1.28 (II) 512.09 |

Chiral Separation of Compounds of Formula if

Racemates of formula If were separated into the two enantiomers using preparative chiral SFC (Daicel, Chiralcel OJ-H, 5 µm, 30×250 mm, CO$_2$/(2-propanol+0.1% DEA) 90/10, 100 bars, 40° C., flow: 160 mL/min, detection: UV 210 nm).

Both enantiomers (see Table 40) were characterized by analytical chiral SFC (Daicel, Chiralcel OJ-H, 5 µm, 4.6× 250 mm, CO$_2$/2-propanol 90/10, 150 bars, 40° C., flow: 4 mL/min, detection: UV 210 to 280 nm)

TABLE 40

| Ig | Name | Racemate If | $t_R$ [min] chiral SFC |
|---|---|---|---|
| Ig-1 | (R)- or (S)-3-[1-(2-Fluoro-6-methyl-phenyl)-piperidin-4-yl]-4-methyl-1-(2-trifluoromethyl-benzyl)-3,4-dihydro-1H-quinazolin-2-one (enantiomer A) | If-1 | 1.687 |
| Ig-2 | (S)- or (R)-3-[1-(2-Fluoro-6-methyl-phenyl)-piperidin-4-yl]-4-methyl-1-(2-trifluoromethyl-benzyl)-3,4-dihydro-1H-quinazolin-2-one (enantiomer B) (Example 71) | If-1 | 2.022 |

Synthesis of Intermediates of Formula E-1

To a soln. of aniline BB-11 and bromide or chloride BB-3 (1.2 eq) in MeCN (7 mL/mmol) was added DIPEA (2.5 eq) and the rxn mixture was stirred at 70° C. for a given time (see Table 41). The volatiles were evaporated and the crude was purified by CC using Hept/EtOAc.

TABLE 41

| E-1 | Name | Reactant BB-11 | Reactant BB-3 | time [h] | $t_R$ [min] (LC/MS method) | MS-data m/z $[M+H]^+$ |
|---|---|---|---|---|---|---|
| E-1-1 | [2-(2-Trifluoromethyl-benzylamino)-benzyl]-carbamic acid tert-butyl ester | tert-Butyl 2-aminobenzyl carbamate | 2-(Trifluoromethyl) benzyl bromide | 18 | 1.14 (II) | 381.10 |

Synthesis of Intermediates of Formula E-2

To a soln. of intermediate E-1 (1 eq) in DCM (10 mL/mmol) was added TFA (1.7 mL/mmol) at 0° C. and the rxn mixture was stirred at 40° C. for a given time (see Table 42). It was cooled to 0° C. and quenched with a 32% aq. soln. of NaOH until pH reached 12 to 13 and extracted with DCM (3×). The combined org. phases were washed with brine, dried over MgSO$_4$ and concentrated in vacuo.

TABLE 42

| E-2 | Name | Reactant E-1 | time [h] | $t_R$ [min] (LC/MS method) | MS-data m/z $[M + H]^+$ |
|---|---|---|---|---|---|
| E-2-1 | (2-Aminomethyl-phenyl)-(2-trifluoromethyl-benzyl)-amine | E-1-1 | 1 | 0.72 (II) | 281.05 |

Synthesis of Intermediates of Formula E-3

To a soln. of intermediate E-2 (1 eq) in MeCN (3.7 mL/mmol) was added CDI (2 eq) and the rxn mixture was stirred at a given temperature for a given time (see Table 43). The solvent was evaporated off and the residue was partitioned between EtOAc and water. The org. phase was washed with brine, dried over MgSO$_4$ and concentrated in vacuo. The crude was purified by CC using Hept/EtOAc.

TABLE 43

| E-3 | Name | Reactant | T [° C.] time [h] | $t_R$ [min] (LC/MS method) | MS-data m/z $[M + H]^+$ |
|---|---|---|---|---|---|
| E-3-1 | 1-(2-Trifluoromethyl-benzyl)-3,4-dihydro-1H-quinazolin-2-one | E-2-1 | 40 1.5 | 0.96 (II) | 307.01 |

Synthesis of Intermediates of Formula E-4

Method a (Mitsunobu): From Compounds of Formula E-3

To a soln. of intermediate E-3 (1 eq) and BB-12 (1.5 eq) in toluene (7 mL/mmol) was added a 1M soln. of (tributylphosphoranylidene)acetonitrile in toluene (2 eq) under argon. The rxn mixture was heated to 110° C. and stirred for a given time (see Table 44). It was quenched with water and extracted with EtOAc (3×). The combined org. phases were washed with brine, dried over MgSO$_4$ and concentrated in vacuo. The crude was purified by CC using Hept/EtOAc.

Method B (N-Alkylation): From Compounds of Formula E-8

To a soln. of intermediate E-8 (1 eq) in anh. THF (4.9 mL/mmol) was added NaH (5 eq, as a 60% dispersion in mineral oil) at RT followed by BB-3 (1.2 eq). When necessary in terms of solubility, anh. DMF (0.2 mL/mmol) could be added. The rxn mixture was stirred at a given temperature for a given time (see Table 44), quenched with water at 0° C. and extracted with EtOAc (3×). The combined org. phases were washed with brine, dried over MgSO$_4$ and concentrated in vacuo. The crude was purified by CC using Hept/EtOAc.

TABLE 44

| E-4 | Name | Reactant E-3 (method A) E-8 (method B) | Reactant BB-12 (method A) BB-3 (method B) | Method T [° C.] time [h] | $t_R$ [min] (LC/MS method) | MS-data m/z $[M+H]^+$ |
|---|---|---|---|---|---|---|
| E-4-1 | 4-[2-Oxo-1-(2-trifluoromethyl-benzyl)-1,4-dihydro-2H-quinazolin-3-yl]-azepane-1-carboxylic acid tert-butyl ester | E-3-1 | tert-Butyl 4-hydroxyazepane-1-carboxylate | A 110 18 | 1.19 (II) | 504.13 |
| E-4-2 | 3-[2-Oxo-1-(2-trifluoromethyl-benzyl)-1,4-dihydro-2H-quinazolin-3-yl]-azetidine-1-carboxylic acid benzyl ester | E-8-1 | 2-(trifluoromethyl) benzyl bromide | B RT 10 | 1.14 (II) | 496.24 |

Synthesis of Intermediates of Formula E-5

Method a (Boc Cleavage)

To a soln. of intermediate E-4 (1 eq) in DCM (10 mL/mmol) was added TFA (1.5 mL/mmol) at 0° C. and the rxn mixture was stirred at RT for a given time (see Table 45). It was cooled to 0° C. and quenched with a 32% aq. soln. of NaOH until pH reached 12 to 13 and extracted with DCM (3×). The combined org. phases were washed with brine, dried over MgSO$_4$ and concentrated in vacuo.

Method B (Cbz Cleavage)

Intermediate E-4 (1 eq) was dissolved in EtOH (6.5 mL/mmol) and the flask was evacuated three times and refilled with nitrogen. Wet Pd/C (0.04 eq) was added and the flask was evacuated and refilled three times with hydrogen. The suspension was hydrogenated under atmospheric pressure for a given time (see Table 45) and filtered over a pad of Celite. The cake was washed with EtOAc and MeOH and the filtrate was concentrated in vacuo. The crude was purified by CC using DCM/MeOH.

TABLE 45

| E-5 | Name | Reactant E-4 | Method | $t_R$ [min] (LC/MS method) | MS-data m/z [M + H]$^+$ |
|---|---|---|---|---|---|
| E-5-1 | 3-Azepan-4-yl-1-(2-trifluoromethyl-benzyl)-3,4-dihydro-1H-quinazolin-2-one | E-4-1 | A1 | 0.77 (II) | 404.08 |
| E-5-2 | 3-Azetidin-3-yl-1-(2-trifluoromethyl-benzyl)-3,4-dihydro-1H-quinazolin-2-one | E-4-2 | B1 | 0.76 (II) | 362.26 |

Synthesis of Intermediates of Formula E-6

To a soln. of amine BB-13 (1 eq) and ketone BB-14 (1.05 eq) in THF (4 mL/mmol) were added AcOH (1.5 eq) followed by NaBH(OAc)$_3$ (1.5 eq) portionwise. The rxn mixture was stirred at RT for a given time (see Table 46). It was quenched with a sat. aq. soln. of NaHCO$_3$ and extracted with EtOAc (3×). The combined org. phases were washed with brine, dried over MgSO$_4$ and concentrated in vacuo. The crude was purified by CC using Hept/EtOAc.

TABLE 46

| E-6 | Name | Reactant BB-13 | Reactant BB-14 | time [h] | $t_R$ [min] (LC/MS method) | MS-data m/z [M+H]$^+$ |
|---|---|---|---|---|---|---|
| E-6-1 | 3-(2-tert-Butoxy-carbonyl amino-benzyl-amino)-azetidine-1-carboxylic acid benzyl ester | tert-Butyl 2-(aminomethyl) phenylcarbamate | Benzyl 3-oxoazetidine-1-carboxylate | 18 | 0.76 (II) | 412.22 |

Synthesis of Intermediates of Formula E-7

To a soln. of intermediate E-6 (1 eq) in DCM (10 mL/mmol) was added TFA (4.5 mL/mmol) at 0° C. and the rxn mixture was stirred at RT for a given time (see Table 47). It was cooled to 0° C. and quenched with a 1M aq. soln. of NaOH until pH reached 12 to 13 and extracted with DCM (3×). The combined org. phases were washed with brine, dried over MgSO$_4$ and concentrated in vacuo.

TABLE 47

| E-7 | Name | Reactant E-6 | time [h] | $t_R$ [min] (LC/MS method) | MS-data m/z [M + H]$^+$ |
|---|---|---|---|---|---|
| E-7-1 | 3-(2-Amino-benzyl-amino)-azetidine-1-carboxyli cacid benzyl ester | E-6-1 | 3 | 0.64 (II) | 312.13 |

Synthesis of Intermediates of Formula E-8

To a soln. of intermediate E-7 (1 eq) in MeCN (3.7 mL/mmol) was added CDI (2 eq) and the rxn mixture was stirred at RT for a given time (see Table 48). The solvent was evaporated off and the residue was partitioned between EtOAc and water. The org. phase was washed with brine, dried over MgSO$_4$ and concentrated in vacuo. The crude was purified by CC using Hept/EtOAc.

TABLE 48

| E-8 | Name | Reactant E-7 | time [h] | $t_R$ [min] (LC/MS method) | MS-data m/z [M + H]$^+$ |
|---|---|---|---|---|---|
| E-8-1 | 3-(2-Oxo-1,4-dihydro-2H-quinazolin-3-yl)-azetidine-1-carboxylic acid benzyl ester | E-7-1 | 18 | 0.89 (II) | 337.99 |

Synthesis of Compounds of Formula Ih

To a mixture of E-5 (1 eq), BB-4 (1.5 eq) and sodium tert-butoxide (2 eq) in toluene (3.5 mL/mmol) under N2, was added BINAP (0.2 eq) and Pd$_2$(dba)$_3$ (0.1 eq). The rxn mixture was flushed with N2, heated at a given temperature and stirred for a given time (see Table 49). It was partitioned between water and EtOAc and the org. phase was washed with brine, dried over MgSO$_4$ and concentrated in vacuo. The crude was purified by CC using Hept/EtOAc.

TABLE 49

| Ih | Name | Reactant E-5 | Reactant BB-4 | T [° C.] | time [h] | $t_R$ [min] (LC/MS method) | MS-data m/z [M+H]$^+$ |
|---|---|---|---|---|---|---|---|
| Ih-1 | 3-[1-(2-Fluoro-6-methyl-phenyl)-azepan-4-yl]-1-(2-trifluoromethyl-benzyl)-3,4-dihydro-1H-quinazolin-2-one (Example 77) | E-5-1 | 2-Bromo-3-fluoro-toluene | 110 | 18 | 1.31 (II) | 512.12 |
| Ih-2 | 3-[1-(2-Fluoro-6-methyl-phenyl)-azetidin-3-yl]-1-(2-trifluoromethyl-benzyl)-3,4-dihydro-1H-quinazolin-2-one (Example 81) | E-5-2 | 2-Bromo-3-fluoro-toluene | 100 | 18 | 1.20 (II) | 470.21 |

II. Biological Assays
In Vitro Assay

Adherent cells (CHO-K1 C5AR1 beta-arrestin cell line, DiscoverX, CA USA) are washed with PBS, detached by incubation with Dissociation Buffer (Gibco Cat #13151-014, 2 ml per 165 cm2 dish) for 3 minutes, then washed with 10 ml PBS (without Mg++ and Ca++) and counted. 7'500 cells/384-well are seeded out in 384-well plates (Cell culture plate MTP384 white Polystyrene, Corning, Cat #3570) in 20 µl/well Cell plating medium (F12 HAMs/10% FCS/1% P/S) and incubated at 37° C./5% CO2/24 h.

5 µl Antagonist at 6-fold end concentration or DMSO control is added to assay medium and subsequently 5 µl 1-10 nM C5a agonist at 6 fold end concentration. Cells are centrifuged for 1 min at 1000 rpm and incubated for 1.5 hour in at 37° C. Plates are equilibrated at room temperature for several minutes before adding 12 µl/well Detection Reagent (PathHunter Detection Kit, DiscoverX, Cat #93-0001).

Plates are centrifuged for 1 min at 1000 rpm and incubated for 45 minutes at RT before being measured on a Fluostar Optima, BMG Labtech. $IC_{50}$ values are calculated from a serial dilution range of antagonist using inhouse software and given in nmol/l.

The calculated $IC_{50}$ values may fluctuate depending on the daily cellular assay performance. Fluctuations of this kind are known to those skilled in the art. Average $IC_{50}$ values from several measurements are given as geometric mean values.

Antagonistic activities of exemplified compounds are displayed in Table 50.

TABLE 50 list of examples and their antagonistic activities

| Example Number | Compound N° | C5aR IC$_{50}$ (nM) | Example Number | Compound N° | C5aR IC$_{50}$ (nM) | Example Number | Compound N° | C5aR IC$_{50}$ (nM) |
| --- | --- | --- | --- | --- | --- | --- | --- | --- |
| 1 | Ia-1 | 17 | 29 | Ia-28 | 35 | 57 | Ia-46 | 24 |
| 2 | Ia-2 | 46 | 30 | Ia-29 | 45 | 58 | Ie-1 | 21 |
| 3 | Ia-3 | 199 | 31 | Ia-30 | 37 | 59 | Ia-47 | 38 |
| 4 | Ia-4 | 944 | 32 | Ia-31 | 280 | 60 | Ia-48 | 28 |
| 5 | Ia-5 | 300 | 33 | Ia-32 | 43 | 61 | Ia-49 | 36 |
| 6 | Ia-6 | 245 | 34 | Ia-33 | 116 | 62 | Ia-50 | 38 |
| 7 | Ia-7 | 58 | 35 | Ia-34 | 43 | 63 | Ia-51 | 61 |
| 8 | Ia-8 | 104 | 36 | Ia-35 | 199 | 64 | Ie-2 | 782 |
| 9 | Ia-9 | 25 | 37 | Ia-36 | 138 | 65 | Ia-52 | 67 |
| 10 | Ia-10 | 1871 | 38 | Ia-37 | 211 | 66 | Ie-3 | 1918 |
| 11 | Ia-11 | 219 | 39 | Ia-38 | 1047 | 67 | Ia-53 | 46 |
| 12 | Ib-1 | 679 | 40 | Ia-39 | 135 | 68 | Ia-54 | 66 |
| 13 | Ia-12 | 32 | 41 | Id-1 | 109 | 69 | Ia-55 | 13 |
| 14 | Ia-13 | 627 | 42 | Ia-40 | 63 | 70 | If-1 | 205 |
| 15 | Ia-14 | 847 | 43 | Ia-41 | 299 | 71 | Ig-2 | 59 |
| 16 | Ia-15 | 635 | 44 | Ic-1 | 33 | 72 | Ib-2 | 2656 |
| 17 | Ia-16 | 437 | 45 | Ia-43 | 191 | 73 | Ib-3 | 1335 |
| 18 | Ia-17 | 28 | 46 | Ic-2 | 35 | 74 | Ia-56 | 17 |
| 19 | Ia-18 | 53 | 47 | Ic-3 | 1658 | 75 | Ia-57 | 55 |
| 20 | Ia-19 | 181 | 48 | Ic-4 | 298 | 76 | Ia-58 | 50 |
| 21 | Ia-20 | 37 | 49 | Ia-44 | 102 | 77 | Ih-1 | 175 |
| 22 | Ia-21 | 52 | 50 | Ic-5 | 2558 | 78 | Ia-59 | 80 |
| 23 | Ia-22 | 32 | 51 | Ic-6 | 113 | 79 | Ia-60 | 57 |
| 24 | Ia-23 | 383 | 52 | Ic-7 | 69 | 80 | Ia-61 | 1792 |
| 25 | Ia-24 | 497 | 53 | Ic-8 | 32 | 81 | Ih-2 | 1284 |
| 26 | Ia-25 | 35 | 54 | Ic-9 | 66 | 82 | Ic-11 | 24 |
| 27 | Ia-26 | 37 | 55 | Ic-10 | 512 | 83 | Ia-63 | 1316 |
| 28 | Ia-27 | 287 | 56 | Ia-45 | 28 | | | |

The invention claimed is:

1. A compound of formula (I)

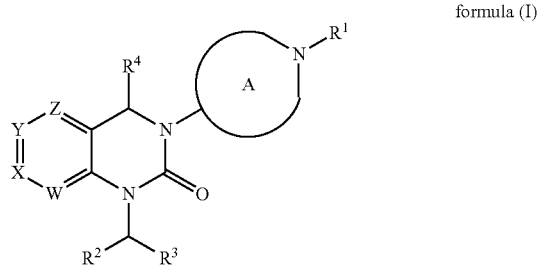

formula (I)

wherein

W represents N, or $CR^5$ wherein $R^5$ represents hydrogen or $(C_{1-3})$alkoxy; and X, Y and Z independently represent CH or N;

ring A represents an unsubstituted, saturated 4- to 7-membered mono-cyclic carbocyclic ring containing the ring nitrogen atom to which $R^1$ is attached;

$R^1$ represents phenyl; 5-membered heteroaryl; or 6-membered heteroaryl;

wherein said phenyl, 5-membered heteroaryl or 6-membered heteroaryl independently is mono-, di- or tri-substituted, wherein the substituents are independently selected from $(C_{1-4})$alkyl;
$(C_{1-4})$alkoxy;
$(C_{1-3})$fluoroalkyl;
$(C_{1-3})$fluoroalkoxy;
halogen;
cyano;
$(C_{3-6})$cycloalkyl;

$R^2$ represents phenyl; 5-membered heteroaryl; or 6-membered heteroaryl;

wherein said phenyl, 5-membered heteroaryl, or 6-membered heteroaryl independently is mono-, or di-substituted, wherein the substituents are independently selected from $(C_{1-4})$alkyl;
$(C_{1-4})$alkoxy;
$(C_{1-3})$fluoroalkyl;
$(C_{1-3})$fluoroalkoxy;
halogen;
hydroxy-$(C_{2-3})$alkoxy;
$(C_{1-3})$alkyl-carbonyl-oxy-$(C_{2-3})$alkoxy;
cyano-$(C_{1-2})$alkoxy;
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl independently contains one optional ring oxygen atom; or
$R^{21a}R^{21b}N$—$(C_{2-3})$alkylene-O—, wherein $R^{21a}$ and $R^{21b}$ independently represent hydrogen or $(C_{1-4})$alkyl;

$R^3$ represents hydrogen, $(C_{1-3})$alkyl, or $(C_{1-3})$alkoxy-carbonyl; and $R^4$ represents hydrogen, or $(C_{1-4})$alkyl;

or a pharmaceutically acceptable salt thereof.

2. The compound according to claim 1; wherein ring (A) represents a saturated 4- to 7-membered mono-cyclic carbocyclic ring containing the ring nitrogen atom to which $R^1$ is attached, wherein said ring is selected from azetidin-1,3-diyl, pyrrolidin-1,3-diyl, piperidin-1,4-diyl, and azepan-1,4-diyl, or a pharmaceutically acceptable salt thereof.

3. The compound according to claim 1; wherein ring A represents pyrrolidin-1,3-diyl, or piperidin-1,4-diyl;

or a pharmaceutically acceptable salt thereof.

4. The compound according to claim 1; wherein

W, X, Y and Z all represent CH;

W represents $CR^5$ wherein $R^5$ represents $(C_{1-3})$alkoxy; and X, Y and Z all represent CH;

W represents $CR^5$ wherein $R^5$ represents hydrogen or $(C_{1-3})$alkoxy; one of X, Y and Z represents N, and the remaining of X, Y and Z represent CH;

W represents N; and X, Y and Z all represent CH;

two of W, X, Y and Z represent N, and the remaining of W, X, Y and Z represent CH;

or a pharmaceutically acceptable salt thereof.

5. The compound according to claim 1; wherein

W, X, Y and Z all represent CH;

W represents $CR^5$ wherein $R^5$ represents $(C_{1-3})$alkoxy; and X, Y and Z all represent CH;

two of W, X, Y and Z represent N, and the remaining of W, X, Y and Z represent CH;

or a pharmaceutically acceptable salt thereof.

6. The compound according to claim 1; wherein
R$^1$ represents
- phenyl which is mono-, or di- or tri-substituted, wherein the substituents are independently selected from:
  - (C$_{1-4}$)alkyl;
  - (C$_{1-4}$)alkoxy;
  - (C$_{1-3}$)fluoroalkyl;
  - (C$_{1-3}$)fluoroalkoxy;
  - halogen;
  - cyano; and
  - (C$_{3-6}$)cycloalkyl; or
- pyrazolyl which is mono-, or di- or tri-substituted, wherein the substituents are independently selected from:
  - (C$_{1-4}$)alkyl;
  - halogen;
  - cyano; and
  - (C$_{3-6}$)cycloalkyl; or
- pyridinyl which is mono-, or di- or tri-substituted, wherein the substituents are independently selected from:
  - (C$_{1-4}$)alkyl;
  - (C$_{1-4}$)alkoxy;
  - halogen;
  - cyano; and
  - (C$_{3-6}$)cycloalkyl;

or a pharmaceutically acceptable salt thereof.

7. The compound according to claim 1; wherein
R$^1$ represents
- phenyl which is mono- or di-substituted, wherein at least one substituent is attached in ortho position with regard to the point of attachment of the rest of the molecule, wherein the substituents are independently selected from:
  - (C$_{1-4}$)alkyl;
  - (C$_{1-4}$)alkoxy;
  - (C$_{1-3}$)fluoroalkyl;
  - (C$_{1-3}$)fluoroalkoxy;
  - halogen;
  - cyano; and
  - (C$_{3-6}$)cycloalkyl;
- pyrazolyl which is tri-substituted, wherein two of said substituents are independently selected from:
  - (C$_{1-4}$)alkyl; and
  - (C$_{3-6}$)cycloalkyl;

and the remaining of said substituents is independently halogen or cyano; or
- pyridinyl which is di-substituted, wherein at least one substituent is attached in ortho position with regard to the point of attachment of the rest of the molecule, wherein the substituents are independently selected from:
  - (C$_{1-4}$)alkyl;
  - (C$_{1-4}$)alkoxy; and
  - halogen;

or a pharmaceutically acceptable salt thereof.

8. The compound according to claim 1; wherein
R$^1$ represents
- phenyl which is mono- or di-substituted, wherein at least one substituent is attached in ortho position with regard to the point of attachment of the rest of the molecule, wherein the substituents are independently selected from:
  - (C$_{1-4}$)alkyl;
  - (C$_{1-4}$)alkoxy;
  - (C$_{1-3}$)fluoroalkyl;
  - (C$_{1-3}$)fluoroalkoxy;
  - halogen;
  - cyano; and
  - (C$_{3-6}$)cycloalkyl; or
- pyridinyl which is di-substituted, wherein at least one substituent is attached in ortho position with regard to the point of attachment of the rest of the molecule, wherein the substituents are independently selected from:
  - (C$_{1-4}$)alkyl;
  - (C$_{1-4}$)alkoxy; and
  - halogen;

or a pharmaceutically acceptable salt thereof.

9. The compound according to claim 1; wherein
R$^2$ represents phenyl; wherein said phenyl is mono-, or di-substituted, wherein the substituents are independently selected from
- (C$_{1-4}$)alkyl;
- (C$_{1-4}$)alkoxy;
- (C$_{1-3}$)fluoroalkyl;
- (C$_{1-3}$)fluoroalkoxy;
- halogen;
- hydroxy-(C$_{2-3}$)alkoxy;
- (C$_{1-3}$)alkyl-carbonyl-oxy-(C$_{2-3}$)alkoxy;
- cyano-(C$_{1-2}$)alkoxy;
- (C$_{3-6}$)cycloalkyl-X$^{21}$—, wherein X$^{21}$ represents a direct bond, —O—, or —(C$_{1-3}$)alkylene-O—, and wherein the (C$_{3-6}$)cycloalkyl independently contains one optional ring oxygen atom; and
- R$^{21a}$R$^{21b}$N—(C$_{2-3}$)alkylene-O—, wherein R$^{21a}$ and R$^{21b}$ independently represent hydrogen or (C$_{1-4}$)alkyl;

or R$^2$ represents thiazolyl; wherein said thiazolyl is mono-, or di-substituted, wherein the substituents are independently selected from
- (C$_{1-4}$)alkyl;
- (C$_{1-3}$)fluoroalkyl; and
- (C$_{3-6}$)cycloalkyl;

or R$^2$ represents 6-membered heteroaryl; wherein said 6-membered heteroaryl independently is mono-, or di-substituted, wherein the substituents are independently selected from
- (C$_{1-4}$)alkyl;
- (C$_{1-4}$)alkoxy; and
- (C$_{1-3}$)fluoroalkyl;

or a pharmaceutically acceptable salt thereof.

10. The compound according to claim 1; wherein
R$^2$ represents phenyl; wherein said phenyl is mono-, or di-substituted, wherein the substituents are independently selected from
- (C$_{1-4}$)alkyl;
- (C$_{1-4}$)alkoxy;
- (C$_{1-3}$)fluoroalkyl;
- (C$_{1-3}$)fluoroalkoxy;
- halogen;
- hydroxy-(C$_{2-3}$)alkoxy;
- (C$_{1-3}$)alkyl-carbonyl-oxy-(C$_{2-3}$)alkoxy;
- cyano-(C$_{1-2}$)alkoxy;
- (C$_{3-6}$)cycloalkyl-X$^{21}$—, wherein X$^{21}$ represents a direct bond, —O—, or —(C$_{1-3}$)alkylene-O—, and wherein the (C$_{3-6}$)cycloalkyl independently contains one optional ring oxygen atom; and
- R$^{21a}$R$^{21b}$N—(C$_{2-3}$)alkylene-O—, wherein R$^{21a}$ and R$^{21b}$ independently represent hydrogen or (C$_{1-4}$)alkyl;

or R² represents 6-membered heteroaryl; wherein said 6-membered heteroaryl independently is mono-, or di-substituted, wherein the substituents are independently selected from
($C_{1-4}$)alkyl;
($C_{1-4}$)alkoxy; and
($C_{1-3}$)fluoroalkyl;
or a pharmaceutically acceptable salt thereof.

11. The compound according to claim 1 selected from:
3-[1-(2,6-Dimethyl-phenyl)-piperidin-4-yl]-1-(2-trifluoromethyl-benzyl)-3,4-dihydro-1H-quinazolin-2-one;
3-[1-(2,6-Difluoro-phenyl)-piperidin-4-yl]-1-(2-trifluoromethyl-benzyl)-3,4-dihydro-1H-quinazolin-2-one;
3-[1-(2,6-Dimethyl-phenyl)-piperidin-4-yl]-8-methoxy-1-(2-trifluoromethyl-benzyl)-3,4-dihydro-1H-quinazolin-2-one;
8-Methoxy-3-[1-(2-methoxy-phenyl)-piperidin-4-yl]-1-(2-trifluoromethyl-benzyl)-3,4-dihydro-1H-quinazolin-2-one;
3-[1-(2-Fluoro-6-methoxy-phenyl)-piperidin-4-yl]-8-methoxy-1-(2-trifluoromethyl-benzyl)-3,4-dihydro-1H-quinazolin-2-one;
3-[1-(2-Methoxy-phenyl)-piperidin-4-yl]-1-(2-trifluoromethyl-benzyl)-3,4-dihydro-1H-quinazolin-2-one;
3-[1-(2-Fluoro-6-methoxy-phenyl)-piperidin-4-yl]-1-(2-trifluoromethyl-benzyl)-3,4-dihydro-1H-quinazolin-2-one;
3-[(R)-1-(2,6-Difluoro-phenyl)-pyrrolidin-3-yl]-8-methoxy-1-(2-trifluoromethyl-benzyl)-3,4-dihydro-1H-quinazolin-2-one;
3-[(R)-1-(2,6-Dimethyl-phenyl)-pyrrolidin-3-yl]-8-methoxy-1-(2-trifluoromethyl-benzyl)-3,4-dihydro-1H-quinazolin-2-one;
8-Methoxy-3-[(R)-1-(2-methoxy-phenyl)-pyrrolidin-3-yl]-1-(2-trifluoromethyl-benzyl)-3,4-dihydro-1H-quinazolin-2-one;
3-[(R)-1-(2-Fluoro-6-methoxy-phenyl)-pyrrolidin-3-yl]-8-methoxy-1-(2-trifluoromethyl-benzyl)-3,4-dihydro-1H-quinazolin-2-one;
3-[1-(4-Chloro-5-cyclopropyl-2-methyl-2H-pyrazol-3-yl)-piperidin-4-yl]-1-(2-trifluoromethyl-benzyl)-3,4-dihydro-1H-quinazolin-2-one;
3-[1-(2-Fluoro-6-methyl-phenyl)-piperidin-4-yl]-1-(2-trifluoromethyl-benzyl)-3,4-dihydro-1H-quinazolin-2-one;
3-[(S)-1-(2,6-Dimethyl-phenyl)-pyrrolidin-3-yl]-1-(2-trifluoromethyl-benzyl)-3,4-dihydro-1H-quinazolin-2-one;
3-[(S)-1-(2,6-Difluoro-phenyl)-pyrrolidin-3-yl]-1-(2-trifluoromethyl-benzyl)-3,4-dihydro-1H-quinazolin-2-one;
3-[(S)-1-(2-Methoxy-phenyl)-pyrrolidin-3-yl]-1-(2-trifluoromethyl-benzyl)-3,4-dihydro-1H-quinazolin-2-one;
3-[(S)-1-(2-Fluoro-6-methoxy-phenyl)-pyrrolidin-3-yl]-1-(2-trifluoromethyl-benzyl)-3,4-dihydro-1H-quinazolin-2-one;
3-[(R)-1-(2,6-Dimethyl-phenyl)-pyrrolidin-3-yl]-1-(2-trifluoromethyl-benzyl)-3,4-dihydro-1H-quinazolin-2-one;
3-[(R)-1-(2,6-Difluoro-phenyl)-pyrrolidin-3-yl]-1-(2-trifluoromethyl-benzyl)-3,4-dihydro-1H-quinazolin-2-one;
3-[(R)-1-(2-Methoxy-phenyl)-pyrrolidin-3-yl]-1-(2-trifluoromethyl-benzyl)-3,4-dihydro-1H-quinazolin-2-one;
3-[(R)-1-(2-Fluoro-6-methoxy-phenyl)-pyrrolidin-3-yl]-1-(2-trifluoromethyl-benzyl)-3,4-dihydro-1H-quinazolin-2-one;
8-Methoxy-3-[(R)-1-(2-methoxy-6-methyl-phenyl)-pyrrolidin-3-yl]-1-(2-trifluoromethyl-benzyl)-3,4-dihydro-1H-quinazolin-2-one;
3-[1-(2-Methoxy-6-methyl-phenyl)-piperidin-4-yl]-1-(2-trifluoromethyl-benzyl)-3,4-dihydro-1H-quinazolin-2-one;
3-[(R)-1-(2,6-Dimethoxy-phenyl)-pyrrolidin-3-yl]-8-methoxy-1-(2-trifluoromethyl-benzyl)-3,4-dihydro-1H-quinazolin-2-one;
8-Methoxy-3-[1-(2-methoxy-6-methyl-phenyl)-piperidin-4-yl]-1-(2-trifluoromethyl-benzyl)-3,4-dihydro-1H-quinazolin-2-one;
3-[(R)-1-(2-Fluoro-6-methyl-phenyl)-pyrrolidin-3-yl]-1-(2-trifluoromethyl-benzyl)-3,4-dihydro-1H-quinazolin-2-one;
3-[(R)-1-(2-Methoxy-6-methyl-phenyl)-pyrrolidin-3-yl]-1-(2-trifluoromethyl-benzyl)-3,4-dihydro-1H-quinazolin-2-one;
3-(2',4'-Dimethyl-3,4,5,6-tetrahydro-2H-[1,3']bipyridinyl-4-yl)-1-(2-trifluoromethyl-benzyl)-3,4-dihydro-1H-quinazolin-2-one;
3-(2'-Methoxy-4'-methyl-3,4,5,6-tetrahydro-2H-[1,3']bipyridinyl-4-yl)-1-(2-trifluoromethyl-benzyl)-3,4-dihydro-1H-quinazolin-2-one;
3-(2'-Fluoro-4'-methyl-3,4,5,6-tetrahydro-2H-[1,3']bipyridinyl-4-yl)-1-(2-trifluoromethyl-benzyl)-3,4-dihydro-1H-quinazolin-2-one;
3-[(R)-1-(2-Methoxy-4-methyl-pyridin-3-yl)-pyrrolidin-3-yl]-1-(2-trifluoromethyl-benzyl)-3,4-dihydro-1H-quinazolin-2-one;
3-[(R)-1-(2,4-Dimethyl-pyridin-3-yl)-pyrrolidin-3-yl]-1-(2-trifluoromethyl-benzyl)-3,4-dihydro-1H-quinazolin-2-one;
3-[(R)-1-(2-Fluoro-4-methyl-pyridin-3-yl)-pyrrolidin-3-yl]-1-(2-trifluoromethyl-benzyl)-3,4-dihydro-1H-quinazolin-2-one;
3-[(R)-1-(2,6-Dimethyl-phenyl)-pyrrolidin-3-yl]-1-(2-methoxy-benzyl)-3,4-dihydro-1H-quinazolin-2-one;
3-[(R)-1-(2-Fluoro-6-methyl-phenyl)-pyrrolidin-3-yl]-1-(2-methoxy-benzyl)-3,4-dihydro-1H-quinazolin-2-one;
3-[1-(2,6-Dimethyl-phenyl)-piperidin-4-yl]-1-(2-methoxy-benzyl)-3,4-dihydro-1H-quinazolin-2-one;
3-[1-(2-Fluoro-6-methyl-phenyl)-piperidin-4-yl]-1-(2-methoxy-benzyl)-3,4-dihydro-1H-quinazolin-2-one;
3-Fluoro-2-{4-[2-oxo-1-(3-trifluoromethyl-pyrazin-2-ylmethyl)-1,4-dihydro-2H-quinazolin-3-yl]-piperidin-1-yl}-benzonitrile;
3-Fluoro-2-{4-[1-(3-methoxy-pyrazin-2-ylmethyl)-2-oxo-1,4-dihydro-2H-quinazolin-3-yl]-piperidin-1-yl}-benzonitrile;
3-[1-(2-Fluoro-6-methyl-phenyl)-piperidin-4-yl]-1-[1-(2-methoxy-phenyl)-ethyl]-3,4-dihydro-1H-quinazolin-2-one;
6-[1-(2-Fluoro-6-methyl-phenyl)-piperidin-4-yl]-8-(2-trifluoromethyl-benzyl)-5,8-dihydro-6H-pyrimido[4,5-c]pyridazin-7-one;
3-[1-(2-Fluoro-6-methyl-phenyl)-piperidin-4-yl]-1-(3-trifluoromethyl-pyrazin-2-ylmethyl)-3,4-dihydro-1H-quinazolin-2-one;
3-[1-(2-Fluoro-6-methyl-phenyl)-piperidin-4-yl]-1-(3-methoxy-pyrazin-2-ylmethyl)-3,4-dihydro-1H-quinazolin-2-one;

3-[1-(2-Fluoro-6-methyl-phenyl)-piperidin-4-yl]-1-(2-isopropoxy-benzyl)-3,4-dihydro-1H-quinazolin-2-one;

3-[1-(2-Fluoro-6-methyl-phenyl)-piperidin-4-yl]-1-[1-(2-trifluoromethyl-phenyl)-ethyl]-3,4-dihydro-1H-quinazolin-2-one;

1-(2-Ethoxy-benzyl)-3-[1-(2-fluoro-6-methyl-phenyl)-piperidin-4-yl]-3,4-dihydro-1H-quinazolin-2-one;

1-[2-(2-Dimethylamino-ethoxy)-benzyl]-3-[1-(2-fluoro-6-methyl-phenyl)-piperidin-4-yl]-3,4-dihydro-1H-quinazolin-2-one;

Acetic acid 2-(2-{3-[1-(2-fluoro-6-methyl-phenyl)-piperidin-4-yl]-2-oxo-3,4-dihydro-2H-quinazolin-1-ylmethyl}-phenoxy)-ethyl ester;

{3-[1-(2-Fluoro-6-methyl-phenyl)-piperidin-4-yl]-2-oxo-3,4-dihydro-2H-quinazolin-1-yl}-(2-methoxy-phenyl)-acetic acid methyl ester;

3-[1-(2-Fluoro-6-methyl-phenyl)-piperidin-4-yl]-1-[2-(2-hydroxy-ethoxy)-benzyl]-3,4-dihydro-1H-quinazolin-2-one;

3-[1-(2-Fluoro-6-methyl-phenyl)-piperidin-4-yl]-1-[2-(oxetan-3-yloxy)-benzyl]-3,4-dihydro-1H-quinazolin-2-one;

1-(2-Cyclobutoxy-benzyl)-3-[1-(2-fluoro-6-methyl-phenyl)-piperidin-4-yl]-3,4-dihydro-1H-quinazolin-2-one;

3-[1-(2-Fluoro-6-methyl-phenyl)-piperidin-4-yl]-1-[2-(tetrahydro-pyran-4-yloxy)-benzyl]-3,4-dihydro-1H-quinazolin-2-one;

1-(2-Cyclopropylmethoxy-benzyl)-3-[1-(2-fluoro-6-methyl-phenyl)-piperidin-4-yl]-3,4-dihydro-1H-quinazolin-2-one;

(2-{3-[1-(2-Fluoro-6-methyl-phenyl)-piperidin-4-yl]-2-oxo-3,4-dihydro-2H-quinazolin-1-ylmethyl}-phenoxy)-acetonitrile;

1-(2-Cyclopropyl-benzyl)-3-[1-(2-fluoro-6-methyl-phenyl)-piperidin-4-yl]-3,4-dihydro-1H-quinazolin-2-one;

3-[1-(2-Fluoro-6-methyl-phenyl)-piperidin-4-yl]-1-(2-isopropyl-benzyl)-3,4-dihydro-1H-quinazolin-2-one;

3-[1-(2-Fluoro-6-methyl-phenyl)-piperidin-4-yl]-1-(2-trifluoromethyl-benzyl)-3,4-dihydro-1H-pteridin-2-one;

3-[1-(2-Fluoro-6-methyl-phenyl)-piperidin-4-yl]-1-(3-isopropoxy-pyrazin-2-ylmethyl)-3,4-dihydro-1H-quinazolin-2-one;

3-[1-(2-Fluoro-6-methyl-phenyl)-piperidin-4-yl]-1-(3-isopropoxy-pyridin-2-ylmethyl)-3,4-dihydro-1H-quinazolin-2-one;

3-[1-(2-Fluoro-6-methyl-phenyl)-piperidin-4-yl]-1-(4-isopropyl-pyridin-3-ylmethyl)-3,4-dihydro-1H-quinazolin-2-one;

3-[1-(2-Fluoro-6-methyl-phenyl)-piperidin-4-yl]-1-(3-isopropyl-pyrazin-2-ylmethyl)-3,4-dihydro-1H-quinazolin-2-one;

3-[1-(2-Fluoro-6-methyl-phenyl)-piperidin-4-yl]-1-(4-isopropyl-pyrimidin-5-ylmethyl)-3,4-dihydro-1H-quinazolin-2-one;

3-[1-(2-Fluoro-6-methyl-phenyl)-piperidin-4-yl]-1-(2-trifluoromethyl-benzyl)-3,4-dihydro-1H-pyrimido[4,5-d]pyrimidin-2-one;

3-[1-(2-Fluoro-6-methyl-phenyl)-piperidin-4-yl]-1-(2-trifluoromethyl-pyridin-3-ylmethyl)-3,4-dihydro-1H-quinazolin-2-one;

7-[1-(2-Fluoro-6-methyl-phenyl)-piperidin-4-yl]-5-(2-trifluoromethyl-benzyl)-7,8-dihydro-5H-pyrimido[5,4-c]pyridazin-6-one;

3-[1-(2-Fluoro-6-methyl-phenyl)-piperidin-4-yl]-1-(4-trifluoromethyl-pyridin-3-ylmethyl)-3,4-dihydro-1H-quinazolin-2-one;

1-(2-Cyclopropoxy-benzyl)-3-[1-(2-fluoro-6-methyl-phenyl)-piperidin-4-yl]-3,4-dihydro-1H-quinazolin-2-one;

3-[1-(2-Fluoro-6-methyl-phenyl)-piperidin-4-yl]-1-(3-trifluoromethyl-pyridin-2-ylmethyl)-3,4-dihydro-1H-quinazolin-2-one;

3-[1-(2-Fluoro-6-methyl-phenyl)-piperidin-4-yl]-4-methyl-1-(2-trifluoromethyl-benzyl)-3,4-dihydro-1H-quinazolin-2-one;

1,3-Dimethyl-5-{4-[2-oxo-1-(2-trifluoromethyl-benzyl)-1,4-dihydro-2H-quinazolin-3-yl]-piperidin-1-yl}-1H-pyrazole-4-carbonitrile;

3-[1-(4-Chloro-2,5-dimethyl-2H-pyrazol-3-yl)-piperidin-4-yl]-1-(2-trifluoromethyl-benzyl)-3,4-dihydro-1H-quinazolin-2-one;

3-[1-(2-Fluoro-6-methyl-phenyl)-piperidin-4-yl]-1-(2-trifluoromethoxy-benzyl)-3,4-dihydro-1H-quinazolin-2-one;

1-(2-Chloro-benzyl)-3-[1-(2-fluoro-6-methyl-phenyl)-piperidin-4-yl]-3,4-dihydro-1H-quinazolin-2-one;

3-[1-(2-Fluoro-6-trifluoromethyl-phenyl)-piperidin-4-yl]-1-(2-trifluoromethyl-benzyl)-3,4-dihydro-1H-quinazolin-2-one;

3-[1-(2-Fluoro-6-methyl-phenyl)-azepan-4-yl]-1-(2-trifluoromethyl-benzyl)-3,4-dihydro-1H-quinazolin-2-one;

3-[1-(2-Fluoro-6-trifluoromethoxy-phenyl)-piperidin-4-yl]-1-(2-trifluoromethyl-benzyl)-3,4-dihydro-1H-quinazolin-2-one;

3-[1-(2-Chloro-6-methyl-phenyl)-piperidin-4-yl]-1-(2-trifluoromethyl-benzyl)-3,4-dihydro-1H-quinazolin-2-one;

3-[1-(2-Fluoro-6-methyl-phenyl)-piperidin-4-yl]-1-(4-isopropoxy-pyridazin-3-ylmethyl)-3,4-dihydro-1H-quinazolin-2-one;

3-[1-(2-Fluoro-6-methyl-phenyl)-azetidin-3-yl]-1-(2-trifluoromethyl-benzyl)-3,4-dihydro-1H-quinazolin-2-one;

1-(6-trifluoromethyl[2-$^2$H]benzyl)-3-[1-(2-fluoro-6-methyl-phenyl)-piperidin-4-yl]-3,4-dihydro-1H-quinazolin-2-one; or 3-[1-(2-Fluoro-6-methyl-phenyl)-piperidin-4-yl]-1-(2-methyl-4-trifluoromethyl-thiazol-5-ylmethyl)-3,4-dihydro-1H-quinazolin-2-one;

or a pharmaceutically acceptable salt thereof.

12. A pharmaceutical composition comprising, as active principle, a compound according to claim 1, or a pharmaceutically acceptable salt thereof, and at least one therapeutically inert excipient.

13. A medicament comprising the compound according to claim 1, or a pharmaceutically acceptable salt thereof.

14. A method for the treatment in a patient suffering from a disease or disorder comprising administering the compound according to claim 1, or a pharmaceutically acceptable salt thereof, to the patient in need thereof, wherein the disease or disorder is selected from vasculitic diseases or disorders, inflammatory diseases or disorders involving intravascular microvesicle release, immune complex (IC) diseases or disorders, neurodegenerative diseases or disorders, complement related inflammatory diseases or disorders, bullous diseases or disorders, diseases or disorders related to ischemia and/or ischemic reperfusion injury, inflammatory bowel diseases or disorders, autoimmune diseases or disorders, or cancer.

15. A method for administering the compound according to claim 1, or a pharmaceutically acceptable salt thereof, wherein the compound is administered for the treatment of deleterious consequences of contact sensitivity and inflammation caused by contact with artificial surfaces; the treatment of increased leukocyte and platelet activation; the treatment of increased leukocyte and platelet infiltration to tissues; the treatment of pathologic sequelae associated to an intoxication or an injury wherein the injury is trauma, hemorrhage, shock, or surgery; the treatment of pathologic sequelae associated with insulin-dependent diabetes mellitus; the reduction of the risk of myocardial infarction or thrombosis; treatment of edema or increased capillary permeability; or the reduction of coronary endothelial dysfunction induced by cardiopulmonary bypass and/or cardioplegia.

16. A method for the treatment of vasculitic diseases or disorders; inflammatory diseases or disorders involving intravascular microvesicle release, immune complex (IC) diseases or disorders; neurodegenerative diseases or disorders; complement related inflammatory diseases or disorders; bullous diseases or disorders; diseases or disorders related to ischemia and/or ischemic reperfusion injury; inflammatory bowel diseases or disorders; autoimmune diseases or disorders; cancer; deleterious consequences of contact sensitivity and inflammation caused by contact with artificial surfaces; increased leukocyte and platelet activation; increased leukocyte and platelet infiltration to tissues; pathologic sequelae associated to an intoxication or an injury wherein the injury is trauma, hemorrhage, shock, or surgery; pathologic sequelae associated with insulin-dependent diabetes mellitus; the risk of myocardial infarction or thrombosis; edema or increased capillary permeability; or coronary endothelial dysfunction induced by cardiopulmonary bypass and/or cardioplegia, the method comprising administering to a patient an effective amount of a compound of formula (I) as defined in claim 1, or a pharmaceutically acceptable salt thereof.

17. The method of claim 15, wherein the compound is administered for the treatment of pathologic sequelae associated to an intoxication or an injury, wherein the injury is surgery, and the surgery is transplantation surgery.

18. The method of claim 16, wherein the method of treating is a method of treating pathologic sequelae associated to an intoxication or an injury, wherein the injury is surgery, and the surgery is transplantation surgery.

* * * * *